(12) United States Patent
Raaben et al.

(10) Patent No.: US 10,822,597 B2
(45) Date of Patent: *Nov. 3, 2020

(54) CHIMERIC ALKALINE PHOSPHATASE-LIKE PROTEINS

(71) Applicant: AM-Pharma B.V., Utrecht (NL)

(72) Inventors: Willem Raaben, Amersfoort (NL); Luigi Johannes Cornelius Jonk, Utrecht (NL); Erik Jan Van Den Berg, Vught (NL); Andrea Van Elsas, Oss (NL); José Luis Millán, San Diego, CA (US)

(73) Assignee: AM-Pharma B.V., Utrecht (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/891,208

(22) Filed: Feb. 7, 2018

(65) Prior Publication Data

US 2019/0024062 A1  Jan. 24, 2019

Related U.S. Application Data

(63) Continuation of application No. 15/113,696, filed as application No. PCT/NL2015/050048 on Jan. 26, 2015.

(30) Foreign Application Priority Data

Jan. 24, 2014 (EP) .................................. 14152526
Oct. 8, 2014 (EP) .................................. 14188158

(51) Int. Cl.
  *C12N 9/16* (2006.01)
  *A61K 38/46* (2006.01)
  *C12N 15/55* (2006.01)
  *A61K 38/00* (2006.01)

(52) U.S. Cl.
  CPC .............. *C12N 9/16* (2013.01); *A61K 38/465* (2013.01); *C12Y 301/00* (2013.01); *C12Y 301/03001* (2013.01); *A61K 38/00* (2013.01); *C07K 2319/00* (2013.01)

(58) Field of Classification Search
  None
  See application file for complete search history.

(56) References Cited

U.S. PATENT DOCUMENTS

| | | | |
|---|---|---|---|
| 5,567,724 A | 10/1996 | Kelleher et al. | |
| 5,723,441 A | 3/1998 | Higley et al. | |
| 6,290,952 B1 | 9/2001 | Poelstra et al. | |
| 6,406,899 B1 | 6/2002 | Hoelke et al. | |
| 7,157,260 B2 | 1/2007 | Mori et al. | |
| 7,157,261 B2 | 1/2007 | Mayall et al. | |
| 7,786,082 B2 | 8/2010 | Kiss | |
| 7,856,139 B2 | 12/2010 | Chen | |
| 7,973,015 B2 | 7/2011 | Van Ommen et al. | |
| 8,460,654 B2 | 6/2013 | Kiss | |
| 8,557,545 B2 | 10/2013 | Velders et al. | |
| 8,574,863 B2 | 11/2013 | Brands et al. | |
| 8,586,032 B2 | 11/2013 | Pickkers et al. | |
| 8,735,087 B2 | 5/2014 | Brands et al. | |
| 8,784,805 B2 | 7/2014 | Brands | |
| 9,926,544 B2 | 3/2018 | Raaben et al. | |
| 2003/0235845 A1 | 12/2003 | Van Ommen et al. | |
| 2004/0115185 A1 | 6/2004 | Kiss | |
| 2004/0146907 A1* | 7/2004 | Smith ................. C12Q 1/6886 435/6.14 |
| 2006/0099616 A1 | 5/2006 | Van Ommen et al. | |
| 2006/0147952 A1 | 7/2006 | Van Ommen et al. | |
| 2007/0059300 A1 | 3/2007 | Kiss | |
| 2008/0044397 A1 | 2/2008 | Kiss et al. | |
| 2008/0209581 A1 | 8/2008 | Van Ommen et al. | |
| 2009/0010912 A1 | 1/2009 | Brands et al. | |
| 2009/0069244 A1 | 3/2009 | Brouwer et al. | |
| 2009/0228998 A1 | 9/2009 | Van Ommen et al. | |
| 2010/0016313 A1 | 1/2010 | Millan et al. | |
| 2010/0111923 A1 | 5/2010 | Pickkers et al. | |
| 2010/0143323 A1 | 6/2010 | Velders et al. | |
| 2010/0158888 A1 | 6/2010 | Kiss | |
| 2011/0052560 A1 | 3/2011 | Brands | |
| 2011/0142817 A1 | 6/2011 | Brands et al. | |
| 2011/0206654 A1 | 8/2011 | Hodin et al. | |
| 2013/0280232 A1 | 10/2013 | Brands et al. | |
| 2014/0193388 A1 | 7/2014 | Velders et al. | |
| 2014/0219984 A1 | 8/2014 | Arend et al. | |

(Continued)

FOREIGN PATENT DOCUMENTS

CN  1425766 A  6/2003
EP  1132086 A2  9/2001

(Continued)

OTHER PUBLICATIONS

Anderson, H.C., et al., "Impaired Calcification Around Matrix Vesicles of Growth Plate and Bone in Alkaline Phosphatase-deficient Mice," The American Journal of Pathology 164(3):841-847, Elsevier, United States (2004).

(Continued)

*Primary Examiner* — Robert B Mondesi
*Assistant Examiner* — Todd M Epstein
(74) *Attorney, Agent, or Firm* — Sterne, Kessler, Goldstein & Fox P.L.L.C.

(57) ABSTRACT

The invention relates to improved alkaline phosphatases, pharmaceutical compositions comprising improved alkaline phosphatases and the use of improved alkaline phosphatases for preventing, treating or curing diseases.

11 Claims, 30 Drawing Sheets

Specification includes a Sequence Listing.

(56) References Cited

U.S. PATENT DOCUMENTS

| | | |
|---|---|---|
| 2016/0046913 A1 | 2/2016 | Velders et al. |
| 2016/0250299 A1 | 9/2016 | Arend et al. |
| 2017/0009217 A1 | 1/2017 | Jonk et al. |

FOREIGN PATENT DOCUMENTS

| | | |
|---|---|---|
| EP | 1733734 A2 | 12/2006 |
| EP | 1952823 A1 | 8/2008 |
| EP | 1985697 A1 | 10/2008 |
| EP | 2662448 B1 | 12/2016 |
| JP | H04349881 A | 12/1992 |
| JP | H 06284885 A | 10/1994 |
| JP | H0998780 A | 4/1997 |
| JP | H09172962 A | 7/1997 |
| JP | 2000350596 A | 12/2000 |
| JP | 2003146888 A | 5/2003 |
| JP | 2005065564 A | 3/2005 |
| RU | 2006103770 A | 8/2007 |
| WO | WO-9318139 A1 | 9/1993 |
| WO | WO-9505455 A1 | 2/1995 |
| WO | WO-9505456 A1 | 2/1995 |
| WO | WO-9639203 A1 | 12/1996 |
| WO | WO-0037943 A1 | 6/2000 |
| WO | WO-0206214 A1 | 1/2002 |
| WO | WO-02056900 A2 | 7/2002 |
| WO | WO-02057430 A2 | 7/2002 |
| WO | WO-02098433 A1 | 12/2002 |
| WO | WO-03015817 A2 | 2/2003 |
| WO | WO-2004056987 A1 | 7/2004 |
| WO | WO-2005074978 A1 | 8/2005 |
| WO | WO-2006096527 A2 | 9/2006 |
| WO | WO-2008094037 A1 | 8/2008 |
| WO | WO-2008104199 A1 | 9/2008 |
| WO | WO-2008133511 A2 | 11/2008 |
| WO | WO-2010025267 A2 | 3/2010 |
| WO | WO-2012169892 A2 | 12/2012 |
| WO | WO-2015112015 A1 | 7/2015 |

OTHER PUBLICATIONS

Bauerle, J.D. et al., "Adenosine Generation and Signaling During Acute Kidney Injury," Journal of the American Society of Nephrology 22(1):14-20, American Society of Nephrology, United States (2011).

Berger, J., et al., "Cloning and Sequencing of Human Intestinal Alkaline Phosphatase cDNA," Proceedings of the National Academy of Sciences USA 84:695-698, National Academy of Sciences, United States (1987).

Bernstine, E.G., et al., "Alakaline Phosphatase Activity in Mouse Teratoma," Proceedings of the National Academy of Sciences USA 70(12):3899-3903, National Academy of Sciences, United States (1973).

Beumer, C., et al., "Calf Intestinal Alkaline Phosphatase, a Novel Therapeutic Drug for Lipopolysaccharide (LPS)-mediated Diseases, Attenuates LPS Toxicity in Mice and Piglets," Journal of Pharmacology and Experimental Therapeutics 307(2):737-744, American Society for Pharmacology and Experimental Therapeutics, United States (2003).

Bol-Schoenmakers, M., et al., "Intestinal Alkaline Phosphatase Contributes to the Reduction of Severe Intestinal Epithelial Damage," European Journal of Pharmacology 633(1-3):71-77, Elsevier Science, Netherlands (2010).

Bossi, M., et al., "Modifications in a Flexible Surface Loop Modulate the Isozyme-specific Properties of Mammalian Alkaline Phosphatases," Journal of Biological Chemistry 34:25409-25416, American Society for Biochemistry and Molecular Biology, United States (1993).

Boulain, J., et al., Patent Abstracts of Japan, English language Abstract of Japanese Patent Publication No. 09-098780, "Modified Baterium Alkaline Phosphatase and Its Use," Japanese Patent Office, Patent & Utility Model Gazette DB (1997).

Bouxsein, M.L., et al., "Guidelines for Assessment of Bone Microstructure in Rodents Using Micro-computed Tomography," Journal of Bone and Mineral Research 25(7):1468-1486, American Society for Bone and Mineral Research, United States (2010).

Brennan, C.A., et al., "A Molecular Sensor System Based on Genetically Engineered Alkaline Phosphatase," Proceedings of the National Academy of Sciences of the United States of America 92: 5783-5787, National Academy of Sciences, United States (1995).

Chen, K.T., et al., "Identification of Specific Targets for the Gut Mucosal Defense Factor Intestinal Alkaline Phosphatase," American Journal of Physiology. Gastrointestinal and Liver Physiology 299(2):G467-G475, American Physiological Society, United States (2010).

Di Sole, F., "Adenosine and Renal Tubular Function," Current Opinion in Nephrology and Hypertension 17(4):399-407, Lippincott Williams & Wilkins, England (2008).

Eltzschig, H.K., et al., "Purinergic Signaling During Inflammation," The New England Journal of Medicine 367(24):2322-2333, Massachusetts Medical Society, United States (2012).

Engle, M.J., et al., "Two Rat Intestinal Alkaline Phosphatase Isoforms with Different Carboxyl-terminal Peptides are Both Membranebound by a Glycan Phosphatidylinositol Linkage," Journal of Biological Chemistry 20:11935-11940, American Society for Biochemistry and Molecular Biology, United States (1995).

English language Abstract and machine translation of Japanese Patent Publication No. 09-172962 A, Japanese Patent Office, Jul. 8, 1997.

English Language Abstract for CN1425766, Published Jun. 25, 2003.

Eriksson H.J., et al., "Investigations into the Stabilization of Drugs by Sugar Glasses: Delivery of an Insulin-stabilised Alkaline Phosphatase in the Intestinal Lumen Via the Oral Route" International Journal of Pharmaceutics 257:273-281, Elsevier/North-Holland Biomedical Press, Netherlands (2003).

Fedde, K.N., et al., "Alkaline Phosphatase Knock-out Mice Recapitulate the Metabolic and Skeletal Defects of Infantile Hypophosphatasia," Journal of Bone and Mineral Research 14(12):2015-2026, American Society for Bone and Mineral Research, United States (1999).

Foster, B.L., et al., "Central Role of Pyrophosphate in Acellular Cementum Formation," PLoS One 7(6):e38393, Public Library of Science, United States (2012).

Foster, B.L., et al., "Rare Bone Diseases and Their Dental, Oral, and Craniofacial Manifestations," Journal of Dental Research 93(7suppl):7S-19S, Sage, United States (2014).

Foster, B.L., et al., "The Rachitic Tooth," Endocrine Reviews 35(1):1-34, Endocrine Society, United States (2014).

Foster, B.L., et al., "Tooth Root Dentin Mineralization Defects in a Mouse Model of Hypophosphatasia," Journal of Bone and Mineral Research 28(2):271-282, American Society for Bone and Mineral Research, United States (2013).

Gayle, R.B., III., et al., "Identification of Regions in Interleukin-1α Important for Activity," The Journal of Biological Chemistry 268(29):22105-22111, The American Society for Biochemistry and Molecular Biology, Inc., United States (1993).

Greenwood, F.C., et al., "The Preparation of I-131-labelled Human Growth Hormone of High Specific Radioactivity," The Biochemical Journal 89:114-123, Portland Press on behalf of the Biochemical Society, England (1963).

Harms, G., et al., "Immunopathology of Alkaline Phosphatase-induced Granulomatous Hepatitis in Rats," Virchows Archiv. B, Cell Pathology Including Molecular Pathology 62(1):35-43, Springer-Verlag, Germany (1992).

Heemskerk, S., et al., "Alkaline Phosphatase Treatment Improves Renal Function in Severe Sepsis or Septic Shock Patients," Critical Care Medicine 37(2):417-423, Lippincott Williams & Wilkins, United States (2009).

Henthorn, P., et al., "Nucleotide and Amino Acid Sequences of Human Intestinal Alkaline Phosphatase: Close Homology to Placental Alkaline Phosphatase," Proceedings of the National Academy of Sciences USA 84(12):4088, National Academy of Sciences, United States (1987).

(56) References Cited

OTHER PUBLICATIONS

Henthorn, P., et al., "Nucleotide and Amino Acid Sequences of Human Intestinal Alkaline Phosphatase: Close Homology to Placental Alkaline Phosphatase," Proceedings of the National Academy of Sciences USA 84:1234-1238, National Academy of Sciences, United States (1987).

Henthorn, P.S., et al., "Sequence and Characterization of the Human Intestinal Alkaline Phosphatase Gene," The Journal of Biological Chemistry 263:12011-12019, American Society for Biochemistry and Molecular Biology, United States (1988).

Hessle, L., et al., "Tissue-nonspecific Alkaline Phosphatase and Plasma Cell Membrane Glycoprotein-1 Are Central Antagonistic Regulators of Bone Mineralization," Proceedings of the National Academy of Sciences of the USA 99(14):9445-9449, National Academy of Sciences, United States (2002).

Hobson, C.E., et al., "Acute Kidney Injury is Associated with Increased Long-term Mortality after Cardiothoracic Surgery," Circulation 119(18):2444-2453, Lippincott Williams & Wilkins, United States (2009).

Huesa, C., et al., "PHOSPHO1 is Essential for Mechanically Competent Mineralization and the Avoidance of Spontaneous Fractures," Bone 48(5):1066-1074, Elsevier Science, United States (2011).

International Search Report for International Application No. PCT/NL2015/050048, European Patent Office, Netherlands, dated May 11, 2015, 4 pages.

Jacob, S., et al., "Pharmacotherapy of Atrial Fibrillation: A Pathophysiological Perspective and Review," American Journal of Therapeutics 18(3):241-260, Lippincott Williams & Wilkins, United States (2011).

Kats, S., et al., "Anti-inflammatory Effects of Alkaline Phosphatase in Coronary Artery Bypass Surgery with Cardiopulmonary Bypass," Recent Patents on Inflammation & Allergy Drug Discovery 3(3):214-220, Bentham Science Publishers, United Arab Emirates (2009).

Kiffer-Moreira, T., et al., "Catalytic Signature of a Heat-stable, Chimeric Human Alkaline Phosphatase With Therapeutic Potential," PLoS One 9(2):e89374, Public Library of Science, United States (2014).

Kodama, H., et al., "Expression of a Heterodimeric (placental-intestinal) Hybrid Alkaline Phosphatase in KB Cells" Biochimica et Biophysica Acta 1218:163-172, Elsevier Pub. Co., Netherlands (1994).

Koyama, I., et al., "Alkaline Phosphatases Reduce Toxicity of Lipopolysaccharides in Vivo and in Vitro through Dephosphorylation," Clinical Biochemistry 35(6):455-461, Elsevier Science, United States (2002).

Kozlenkov, A., et al., "Function Assignment to Conserved Residues in Mammalian Alkaline Phosphatases," The Journal of Biological Chemistry 277(25):22992-22999, American Society for Biochemistry and Molecular Biology, United States (2002).

Kozlenkov, A., et al., "Residues Determining the Binding Specificity of Uncompetitive Inhibitors to Tissue-nonspecific Alkaline Phosphatase," Journal of Bone and Mineral Research 19(11):1862-1872, American Society for Bone and Mineral Research, United States (2004).

Lameire, N.H., et al., "Acute Kidney Injury: an Increasing Global Concern," Lancet 382(9887):170-179, Elsevier, England (2013).

Le Du, M.H, and Millian, J.L., "Structural Evidence of Functional Divergence in Human Alkaline Phosphatases." Journal of Biological Chemistry 277(51):49808-49814, American Society for Biochemistry and Molecular Biology, United States (2002).

Lee, J.Y., et al., "Erdosteine in Renal Ischemia-reperfusion Injury: an Experimental Study in Pigs," The Journal of Veterinary Medical Science 72(1):127-130, Japanese Society of Veterinary Science, Japan (2010).

Leibovitch, I., et al., "Increased Serum Alkaline Phosphatase Activity: A Possible Indicator of Renal Damage," Journal of Clinical Laboratory Analysis 5(6):406-409, Wiley-Liss, Inc., United States (1991).

Lindner, N.M., et al., "Design and Applications of Biomimetic Anthraquinone Dyes. Purification of Calf Intestinal Alkaline Phosphatase With Immobilised Terminal Ring Analogues of C.I. Reactive Blue 2," Journal of Chromatography 473(1):227-240, Elsevier, Netherlands (1989).

Liu, J., et al., "Tissue-nonspecific Alkaline Phosphatase Deficiency Causes Abnormal Craniofacial Bone Development in the Alpl(−/−) Mouse Model of Infantile Hypophosphatasia," Bone 67:81-94, Elsevier Science, United States (2014).

Lukas, M., et al., "Exogenous Alkaline Phosphatase for the Treatment of Patients With Moderate to Severe Ulcerative Colitis," Inflammatory Bowel Diseases 16(7):1180-1186, Lippincott Williams & Wilkins, United States (2010).

Mandecki, W., et al., Patent Abstracts of Japan, English language Abstract of Japanese Patent Publication No. 04-349881, "Synthesized Alkaline Phosphatase Enzyme Having Improved Specific Activity," Japanese Patent Office, Patent & Utility Model Gazette DB (1992).

Martinez-Moya, P., et al., "Exogenous Alkaline Phosphatase Treatment Complements Endogenous Enzyme Protection in Colonic Inflammation and Reduces Bacterial Translocation in Rats," Pharmacological Research 66(2):144-153, Academic Press, Netherlands (2012).

Mayo Clinic Staff, "Diseases and Conditions Acute kidney failure," accessed at http://www.mayoclinic.org/diseases-conditions/kidney-failure/basics/prevention/con-20024029?p=1 accessed on Jul. 24, 2015, 7 pages (2015).

McKee, M.D., et al., "Enzyme Replacement Therapy Prevents Dental Defects in a Model of Hypophosphatasia," Journal of Dental Research 90(4):470-476, American Dental Assn, United States (2011).

Meganck, J.A., et al., "Beam Hardening Artifacts in Micro-computed Tomography Scanning Can Be Reduced by X-ray Beam Filtration and the Resulting Images Can Be Used to Accurately Measure BMD," Bone 45(6):1104-1116, Elsevier Science, United States (2009).

Millan, J.L., et al., "Enzyme Replacement Therapy for Murine Hypophosphatasia," Journal of Bone and Mineral Research 23(6):777-787, American Society for Bone and Mineral Research, United States (2008).

Millan, Jose Luis, "Alkaline Phosphatases: Structure, Substrate Specificity and Functional Relatedness to Other Members of a Large Superfamily of Enzymes," Purinergic Signaling 2:335-341, Springer, Netherlands (2006).

Mornet, E., et al., "Structural Evidence for a Functional Role of Human Tissue Nonspecific Alkaline Phosphatase in Bone Mineralization," Journal of biological chemistry 26:31171-31178, American Society for Biochemistry and Molecular Biology, United States (2001).

Naber, T.H., et al., "Serum Alkaline Phosphatase Activity During Zinc Deficiency and Long-term Inflammatory Stress," Clinica Chimica Acta 249:109-127, Elsevier, Netherlands (1996).

Narisawa, S., et al., "A Novel Phosphatase Upregulated in Akp3 Knockout Mice," American Journal of Physiology Gastrointestinal and liver physiology 293(5):G1068-G1077, American Physiological Society, United States (2007).

Narisawa, S., et al., "Abnormal Vitamin B6 Metabolism in Alkaline Phosphatase Knock-out Mice Causes Multiple Abnormalities, but Not the Impaired Bone Mineralization," The Journal of Pathology 193(1):125-133, John Wiley and Sons, England (2001).

Narisawa, S., et al., "Inactivation of Two Mouse Alkaline Phosphatase Genes and Establishment of a Model of Infantile Hypophosphatasia," Developmental Dynamics 208(3):432-446, Wiley, United States (1997).

NCBI Acct#NP_001622.2 versus Bossi et al., USPTO in house alignment Feb. 22, 2012.

Nugent, S.G., et al., "Review: Intestinal Luminal pH in Inflammatory Bowel Disease: Possible Determinants and Implications for Therapy with Aminosalicylates and Other Drugs," Gut 48:571-577, British Medical Association, England (2001).

Okamoto, M., et al., Patent Abstracts of Japan, English language Abstract of Japanese Patent Publication No. 2000-350596, "Selec-

(56) References Cited

OTHER PUBLICATIONS tive Assay of Secreted Alkaline Phosphatase Activity," Japanese Patent Office, Patent & Utility Model Gazette DB (2000).
Peters, E., et al., "Alkaline Phosphatase: a Possible Treatment for Sepsis-associated Acute Kidney Injury in Critically ill Patients," American Journal of Kidney Diseases 63(6):1038-1048, W.B. Saunders, United States (2014).
Peters, E., et al., "Alkaline Phosphatase as a Treatment of Sepsis-associated Acute Kidney Injury," The Journal of Pharmacology and Experimental Therapeutics 344(1):2-7, American Society for Pharmacology and Experimental Therapeutics, United States (2013).
Pickkers, P., et al., "Alkaline Phosphatase for Treatment of Sepsis-induced Acute Kidney Injury: a Prospective Randomized Double-blind Placebo-controlled Trial," Critical Care 16(1):R14, BioMed Central Ltd, England (2012).
Poelstra, K., et al., "Dephosphorylation of Endotoxin by Alkaline Phosphatase in Vivo," American Journal of Pathology 151(4):1163-1169, Elsevier, United States (1997).
Ramasamy, S., et al., "Intestinal Alkaline Phosphatase Has Beneficial Effects in Mouse Models of Chronic Colitis," Inflammatory Bowel Diseases 17(2):532-542, Lippincott Williams & Wilkins, United States (2011).
Reinecke, H., et al., "Dilemmas in the Management of Atrial Fibrillation in Chronic Kidney Disease," Journal of the American Society of Nephrology 20(4):705-711, American Society of Nephrology, United States (2009).
Riggle, K.M., et al., "Intestinal Alkaline Phosphatase Prevents the Systemic Inflammatory Response Associated With Necrotizing Enterocolitis," The Journal of Surgical Research 180(1):21-26, Academic Press, United States (2013).
Sanchez De Medina F., et al., "Induction of Alkaline Phosphatase in the Inflamed Intestine: A Novel Pharmacological Target for Inflammatory Bowel Disease," Biochemical Pharmacology, 68:2317-2326, Elsevier Science, England (2004).
Schock-Kusch, D., et al., "Transcutaneous Assessment of Renal Function in Conscious Rats With a Device for Measuring Fitc-sinistrin Disappearance Curves," Kidney International 79(11):1254-1258, Elsevier, United States (2011).
Schock-Kusch, D., et al., "Transcutaneous Measurement of Glomerular Filtration Rate Using FITC-sinistrin in Rats," Nephrology, Dialysis, Transplantation 24(10):2997-3001, Oxford University Press, England (2009).
Shahani, K.M., et al., "Enzymes in Bovine Milk: A Review," Journal of Dairy Science 56(5):531-543, American Dairy Science Association, United States (1973).
Shulka, et al., "Host Cell Protein Clearance During Protein a Chromatography: Development of an Improved Column Wash Step," Biotechnology Progress 24(5):1115-1121, American Institute of Chemical Engineers (2008).
Su, F., et al., "Beneficial Effects of Alkaline Phosphatase in Septic Shock," Critical Care Medicine 34(8):2182-2187, Kolen, United States (2006).
Szuster-Ciesielska, et al., "The Inhibitory Effect of Zinc on Cadmium-induced Cell Apoptosis and Reactive Oxygen Species (ROS) Production in Cell Cultures," Toxicology 145(2-3):159-171, Elsevier, Ireland (2000).
The New York Times, "Chronic Kidney Disease Overview," accessed at http://nytimes.com/health/guides/disease/chronic-renal-failure/overview.html?print=1, accessed on Jul. 24, 2015, 3 pages (2015).
Tuin, A., et al., "Role of Alkaline Phosphatase in Colitis in Man and Rats," Gut 58(3):379-387, British Medical Assn, England (2009).
Tuin, et al., "Oral Administration of Alkaline Phosphatase Ameliorates Colitis." Gastroenterology 132:A231, Abstract #51611 (2007).
Udenfriend, S., et al., "Prediction of Omega Site in Nascent Precursor of Glycosylphophatidylinositol Protein," Methods Enzymology, 250:571-582, Academic Press, United States (1995).

Ueda, Hiroshi, Patent Abstract of Japan, English language Abstract of Japanese Patent Publication No. 2005-065564, "Sensor Protein," Japanese Patent Office, Patent & Utility Model Gazette DB (2005).
Umoh, J.U., et al., "In Vivo Micro-CT Analysis of Bone Remodeling in a Rat Calvarial Defect Model," Physics in Medicine and Biology 54(7):2147-2161, IOP Publishing, England (2009).
Unknown Author, "Chronic Kidney Disease—information Prescription," accessed at http://nhs.uk.Pages/Preview.aspx?site=Kidney-disease-chronic&print=63573354618, accessed on Jul. 24, 2015, 3 pages (2013).
Van Veen, S.Q., et al., "Alkaline Phosphatase Reduces Hepatic and Pulmonary Injury in Liver Ischaemia-reperfusion Combined with Partial Resection," The British Journal of Surgery 93: 448-456, Wiley, England (2006).
Van Veen, S.Q., et al., "Bovine Intestinal Phosphatase Attenuates the Inflammatory Response in Secondary Peritonitis in Mice," Infection and Immunity 73: 4309-4315, American Society for Microbiology, United States (2005).
Verweij, W.R., et al., "Protection Against an *Escherichia coli*-induced Sepsis by Alkaline Phosphatase in Mice," Shock 22(2):174-179, Lippincott Williams & Wilkins, United States (2004).
Wang, E., et al., "Crystal Structure of Alkaline Phosphatase from the Antarctic Bacterium TAB5," Journal of Molecular Biology 366:1318-1331, Elsevier Ltd., England (2007).
Whisstock, et al., "Prediction of Protein Function From Protein Sequence and Structure," Quarterly Reviews of Biophysics 3:307-340 (2003).
Whyte, M.P., et al., "Enzyme Replacement Therapy for Infantile Hypophosphatasia Attempted by Intravenous Infusions of Alkaline Phosphatase-rich Paget Plasma: Results in Three Additional Patients," The Journal of Pediatrics 105(6):926-933, Mosby, United States (1984).
Whyte, M.P., et al., "Enzyme-replacement Therapy in Life-threatening Hypophosphatasia," The New England Journal of piMedicine 366(10):904-913, Massachusetts Medical Society, United States (2012).
Whyte, M.P., et al., "Infantile Hypophosphatasia: Enzyme Replacement Therapy by Intravenous Infusion of Alkaline Phosphatase-rich Plasma From Patients With Paget Bone Disease," The Journal of Pediatrics 101(3):379-386, Mosby, United States (1982).
Wilmer, M.J., et al., "Novel Conditionally Immortalized Human Proximal Tubule Cell Line Expressing Functional Influx and Efflux Transporters," Cell and Tissue Research 339(2):449-457, Springer-Verlag, Germany (2010).
Wray, L., and Harris H., "Demonstration Using Monoclonal Antibodies of Inter-Locus Heteromeric Isozymes of Human Alkaline Phosphatase" Journal of Immunological Methods 55:13-18, Elsevier, Netherlands (1982).
Wuhl, E., et al., "Antihypertensive and Antiproteinuric Efficacy of Ramipril in Children with Chronic Renal Failure," Kidney International 66:768-776, International Society of Nephrology, United States (2004).
Xu, et al., "Directed Evolution of *E. coli* Alkaline Phosphatase Towards Higher Catalytic Activity," Biocatalysis and Biotransformation 21: 41-47, United Kingdom (2003).
Yadav, M.C., et al., "Ablation of Osteopontin Improves the Skeletal Phenotype of Phospho1(−/−) Mice," Journal of Bone and Mineral Research 29(11):2369-2381, American Society for Bone and Mineral Research, United States (2014).
Yadav, M.C., et al., "Dose Response of Bone-targeted Enzyme Replacement for Murine Hypophosphatasia," Bone 49(2):250-256, Elsevier Science, United States (2011).
Yadav, M.C., et al., "Enzyme Replacement Prevents Enamel Defects in Hypophosphatasia Mice," Journal of Bone and Mineral Research 27(8):1722-1734, American Society for Bone and Mineral Research, United States (2012).
Zarbock, A., and Milles, K., "Novel Therapy for Renal Protection," Current Opinion in Anesthesiology 28(4):431-438, Lippincott Williams & Wilkins, United States (2015).

\* cited by examiner

Improved RecAP (LVL-RecAP) Sequence (SEQ ID NO: 1):

1 VIPAEEENPAFWNPQAAEALDAAKKLQPIQKVAKNLILFLGDGLGVPTVTATRILKGQKNGKLGPETPLAMDRFPYLALSKTYNVDRQVPDSAATATAYL
101 CGVKANFQT-GLSAAAARFNQCN-TRGNEVISVMNEAKQAGKSVGVVTTTRVQHASPAGTYAHTVNRNWYSDADMPASARQEGCQDIATQLISNMDIDVIL
201 GGGRKYMFPMCTPDFEYPADASQNGIRLDGKNLVQEWLAKHQCAWYVWNRTELMQASLDQSVTHLMCLFEPGDTKYEILRDPTLDPSLMEMTEAALRLLS
301 RNPRGFYLFVEGGRIDHGHHECVAYQAVTEAVMFDDAIERAGQLTSEEDTLTLVTADHSHVFSFGGYPLRCSSIFGLAPGKARERKAYTVLLYGNGPGYV
401 LKDGARPDVTESESGSPEYRQQSAVPLEEETHGGEDVAVFARGPQAHIVHGVQRQSFVAHVMAFAACLEPYTACDLALPACTTD

RefSEQ hALPI (mature protein sequence of accession number: NM_001631.3) (SEQ ID NO:2):

1 VIPAEEENPAFWNRQAAEALDAAKKLQPIQKVAKNLILFLGDGLGVPTVTATRILKGQKNCKLGPETPLAMDRFPYLALSKTYNVDRQVPDSAATATAYL
101 CGVKANFQT-GLSAAAARFNQCN-TRGNEVISVMNEAKQAGKSVGVVTITRVQHASPAGTYAHTVNRNWYSDADMPASARQEGCQDIATQLISNMDIDVIL
201 GGGRKYMFPMGTPDFEYPADASQNGIRLDGKNLVQEWLAKHQGAWYVWNKTELMQASLDQSVTHLMGLFEPGDIKYEIHRDPTLDPSLMEMTEAALRLLS
301 RNPRGFYLFVEGGRIDHGHHECVAYQALTEAVMFDDAIERAGQLTSEEDTLTLVTADHSHVFSFGGYTLRCSSIFGLAPSKAQDSKAYISILYGNGPGYV
401 FNSQVRPDVNESESCSPDYTQQCAAVPLSSETHCGEDVAFARGPQAHIVHGVQQSFVAHVMAFAACLEPYTACDLAPPACTTD

RefSEQ hALPP (mature protein sequence of accession number: NM_001632.3) (SEQ ID NO: 3):

1 IIPVEEENPDFWNREAAEALGAANKLGAAKLQPAQTAAKNLILFLSDGMGVSTVTAARILKGQKKDKLGPEIPLAMDRFPYVALSKTYNVDKHVPDSGATATAYL
101 CGVKSNFQT-GLSAAARFNQCN-TRGNEVISVMNEAKKAGKSVGVVTITRVQHASPAGTYAHTVNRNWYSDADVPASARQEGCQDIATQLISNMDIDVIL
201 GGGRKYMFRMGTPDFEYPDYSQGGTIRLDGKNLVQEWLAKRQGARYVWNRTELMQASLDPSVTHLMGLFEPGDMKYEIHRDSTLDPSLMEMTEAALRLLS
301 RNFRGFFLFVEGGRIDHGHESRAYRALTETIMFDDAIERAGQLTSEEDTLSLVTADHSHVFSFGGYPLRGSSYPLRCSSIFGLAPGKARDRKAYTVLLYGNGPGYV
401 LKDGARPDVTESESGSPEYRQQSPEYRQQSAVPLEEETHAGHDVAFARGPQAHITPIAHVMAFAACLEPYTACDLAPPACTTD sALPI-ALPP-CD Sequence (SEQ ID NO: 4):

1 VIPAEEENPAFWNKQAAEALDAAKKLQPIQKVAKNLILFLGDGLGVPTVTATRILKGQKNCKLGPETPLAMDRFPYLALSKTYNVDRQVPDSAATATAYL
101 CGVKANFQT-GLSAAAARFNQCN-TRGNEVISVMNRAKQAGKSVGVVTITRVQHASPAGTYAHTVNRNWYSDADMPASARQEGCQDIATQLISNMDIDVIL
201 GGGRKYMFPMGTPDFEYPADASQNGIRLDGKNLVQEWLAKHQGAWYVWNRTELMQASLDQSVTHLMGLFEPGDTKYEIHRDPTLDPSLMEMTEAALRLLS
301 RNPRGFYLFVEGGRIDHGHHECVAYQALTEAVMFDDAIERAGQLTSEEDTLTLVTADHSHVFSFGGYPLRCSSIFGLAPGKARLRKAYTVLLYGNGPGYV
401 LKDGARPDVTESESGSPEYRQQSAVPLEEETHGGEDVAVFARGPQAHIVHGVQRQSFVAHVMAFAACLEPYTACDLAPPACTTD

N-Terminal Sequence (1 - 365) of hALPI (SEQ ID NO:5):

1 VIPAEEENPAFWNRQAAEALDAAKKLQPIQKVAKNLILFLGDGLGVPTVTATRILKGQKNCKLGPETPLAMDRFPYLALSKTYNVDRQVPDSAATATAYL
101 CGVKANFQT-GLSAAAARFNQCN-TRGNEVISVMNRAKQAGKSVGVVTITRVQHASPAGTYAHTVNRNWYSDADMPASARQEGCQDIATQLISNMDIDVIL
201 GGGRKYMFPMGTPDFEYPADASQNGIRLDGKNLVQEWLAKHQGAWYVWNRTELMQASLDQSVTHLMGLFEPGDTKYEIHRDPTLDPSLMEMTEAALRLLS
301 RNPRGFYLFVEGGRIDHGHHECVAYQALTEAVMFDDAIERAGQLTSEEDTLTLVTADHSHVFSFG

Crown domain Sequence (366 - 430) of PLAP (SEQ ID NO: 6):

366 GYPLRGSSIFGLAPGKARDKAYTVLLYGNGPGYVLKDGARPDVTESESGSPEYRQQSAVPLDEE

C-Terminal Sequence (431 - 484) of hALPI (SEQ ID NO: 7):

431 THGGEDVAVFARGPQAHLVHGVQEQSFVAHVMAFAACLEPYTACDLAPPACTTD

FIG. 1

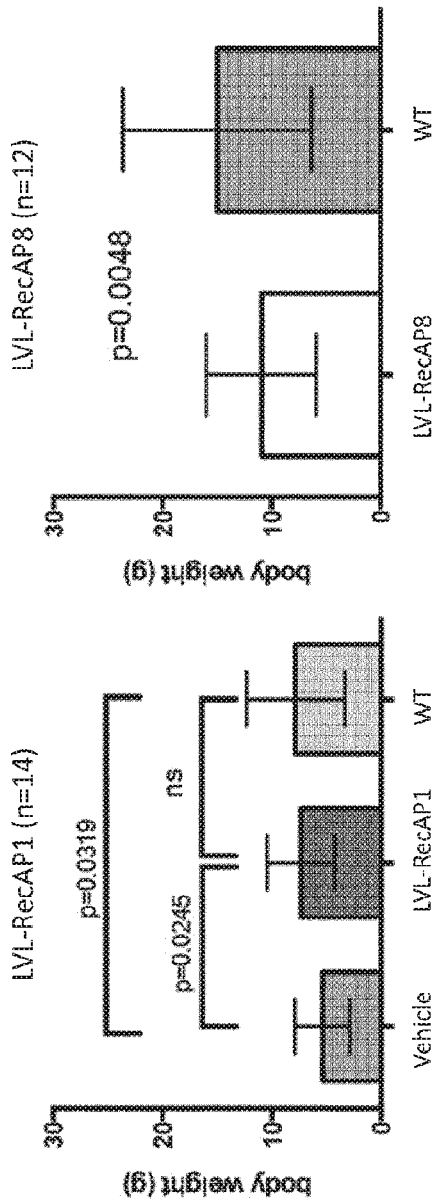
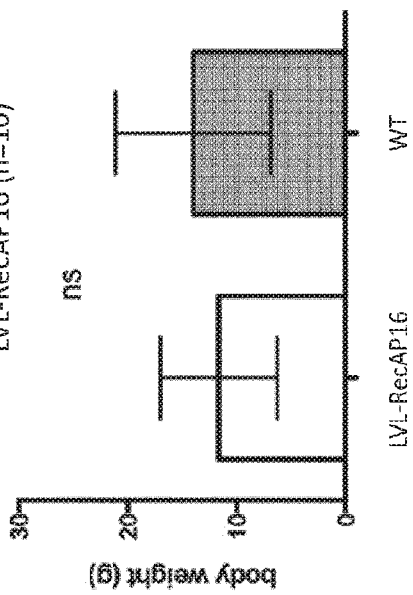
FIG. 6B
FIG. 6C
FIG. 6D

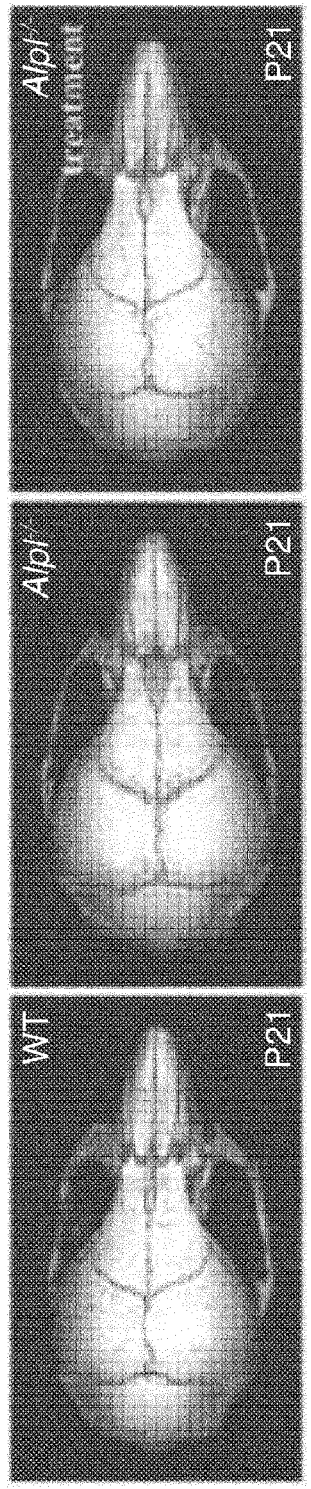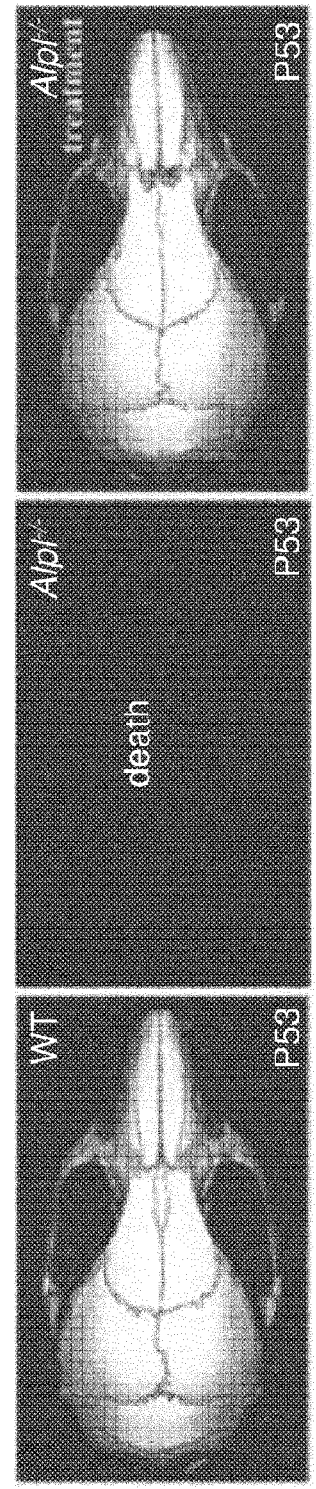

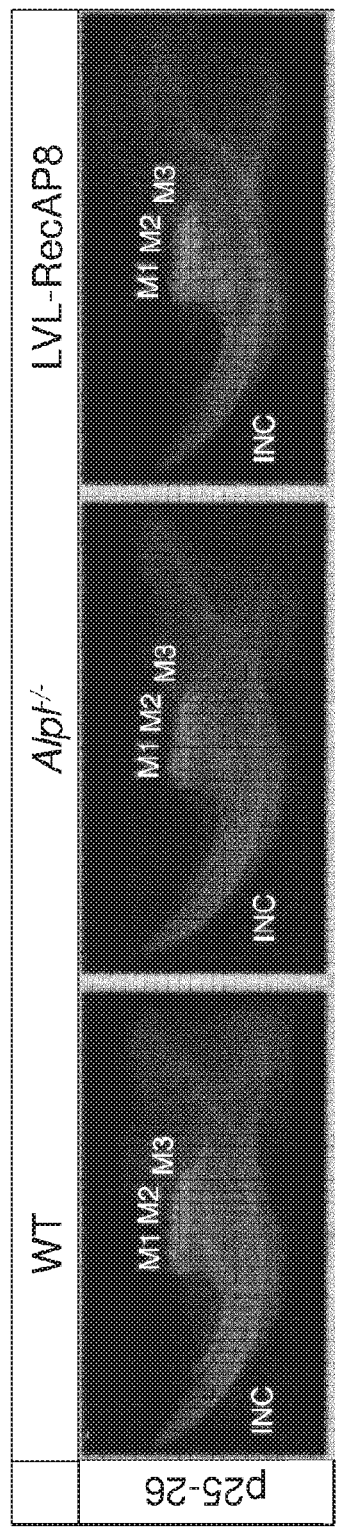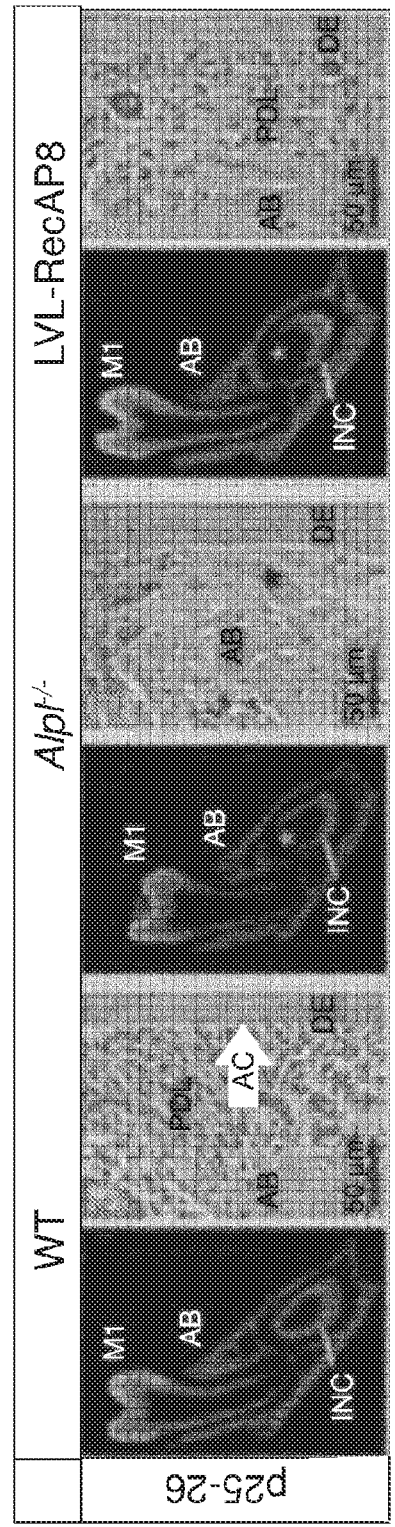

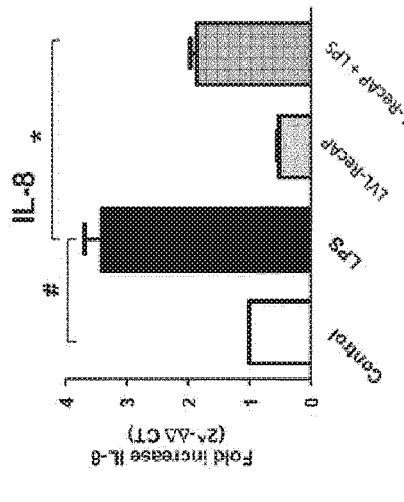
FIG. 12A  FIG. 12B  FIG. 12C
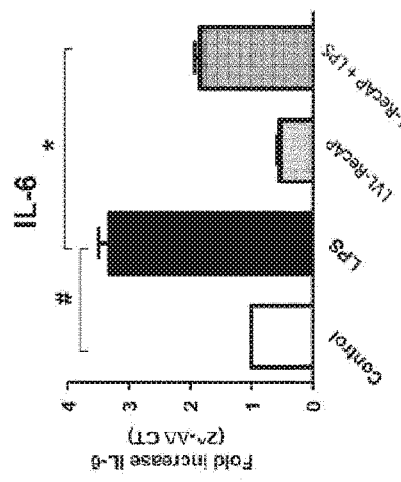
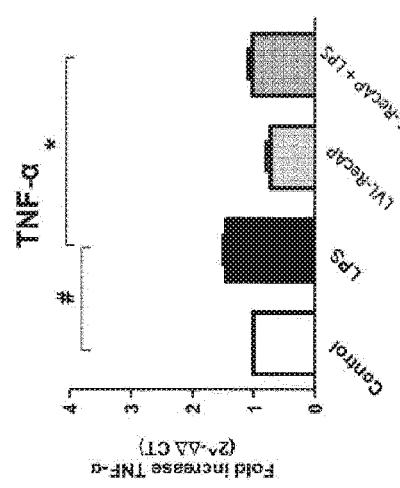
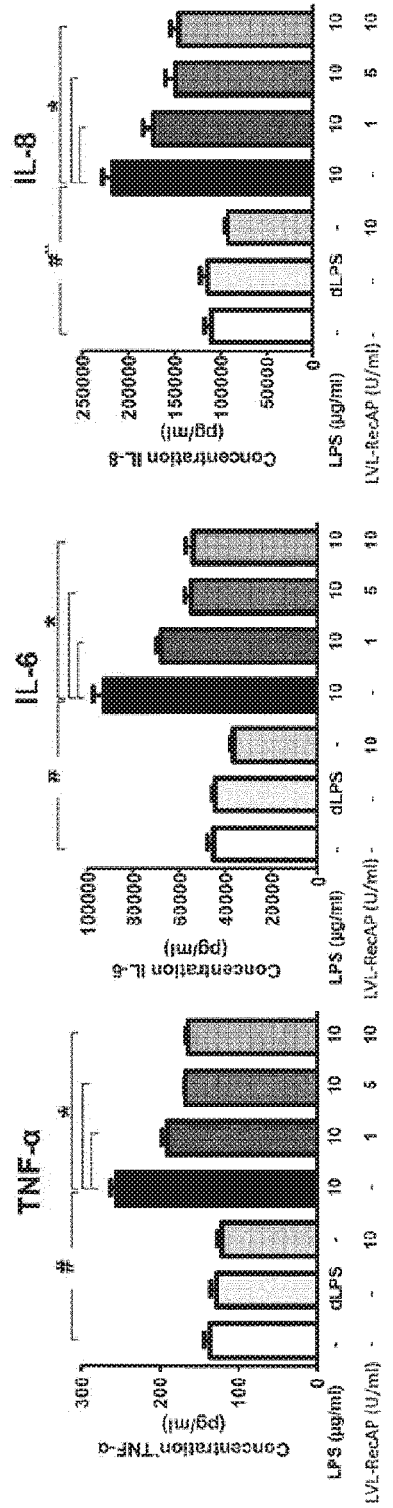
FIG. 12D  FIG. 12E  FIG. 12F

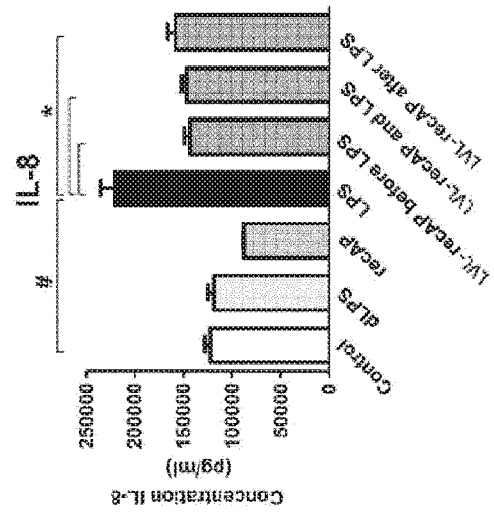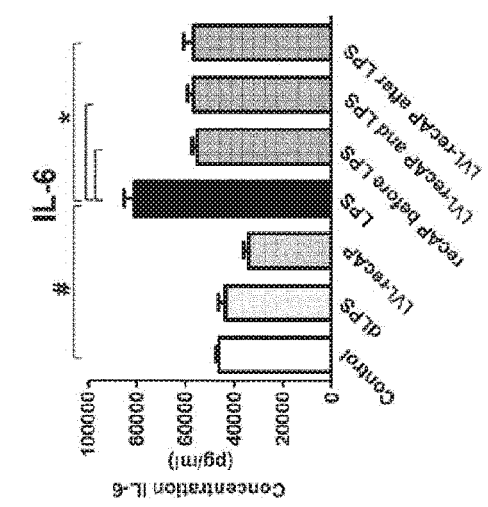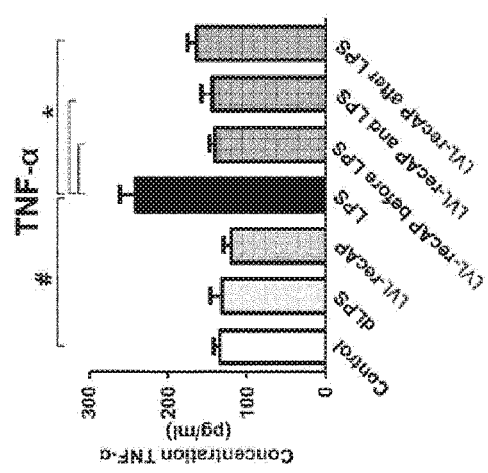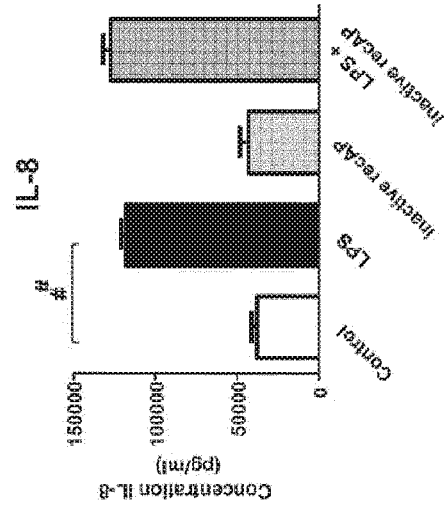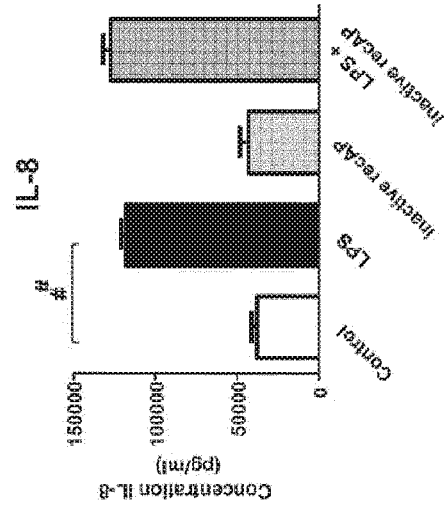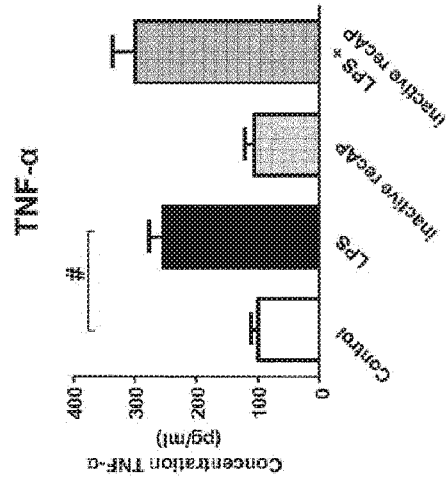

CHIMERIC ALKALINE PHOSPHATASE-LIKE PROTEINS

REFERENCE TO A SEQUENCE LISTING SUBMITTED ELECTRONICALLY VIA EFS-WEB

This application includes a Sequence Listing submitted electronically via EFS-Web (name: "3151.0100002_Sequence_Listing.txt"; size: 21,645 bytes; and created on: Feb. 6, 2018), which is hereby incorporated by reference in its entirety.

The invention relates to alkaline phosphatases with improved properties, pharmaceutical compositions comprising alkaline phosphatases with improved properties and the use of alkaline phosphatases with improved properties for preventing, treating or curing diseases.

A phosphatase is an enzyme that dephosphorylates its substrates; i.e. it hydrolyses phosphoric acid monoesters into a phosphate ion and a molecule with a free hydroxyl group. This action is directly opposite to that of phosphorylases and kinases, which attach phosphate groups to their substrates by using energetic molecules like ATP. Phosphatases can be categorized into two main categories: Cysteine-Dependent Phosphatases (CDPs) and metallo-phosphatases.

Metallo-phosphatases typically co-ordinate 2 catalytically essential metal ion(s) within their active site. There is currently some confusion about the identity of these metal ions, as successive attempts to identify them yield different answers. There is currently evidence that these metals could be magnesium, manganese, iron, zinc, or any combination thereof. It is thought that a hydroxyl ion bridging the two metal ions takes part in nucleophilic attack on the phosphate group.

Phosphatases act in opposition to kinases/phosphorylases, which add phosphate groups to proteins. The addition or removal of a phosphate group may activate or de-activate an enzyme (e.g., kinase signaling pathways) or enable a protein-protein interaction to occur (e.g., SH3 domains); therefore phosphatases are integral to many signal transduction pathways. It should be noted that phosphate addition and removal do not necessarily correspond to enzyme activation or inhibition, and that several enzymes have separate phosphorylation sites for activating or inhibiting functional regulation. CDK, for example, can be either activated or deactivated depending on the specific amino acid residue being phosphorylated. Phosphates are important in signal transduction because they regulate the proteins to which they are attached. To reverse the regulatory effect, the phosphate is removed. This occurs on its own by hydrolysis, or is mediated by protein phosphatases.

One type of phosphatase, alkaline phosphatase (ALP or AP) (EC 3.1.3.1), is a hydrolase enzyme responsible for removing phosphate groups from many types of molecules, including, e.g., nucleotides, proteins, and alkaloids. Up to recently, the alkaline phosphatases were thought to be most effective in an alkaline environment, as the name suggests.

It is thought in the art that one possible physiological role of AP may be that it interacts with inflammatory molecules. First it had been postulated that AP dephosphorylates endotoxins and as such reduces the inflammatory response to these highly inflammatory molecules. Since then, other mechanisms of action have been postulated and pursued. However, up to now, despite its beneficial role in a multitude of inflammatory and other diseases, the mechanism of action has not yet been fully elucidated. In the past, alkaline phosphatase of bovine origin has been used in animal models and clinical trials for the treatment of, for example, sepsis, acute kidney injury, inflammatory bowel disease, enterocolitis, ischemia reperfusion damage, or other inflammatory diseases (Riggle et al, J Surg Res. 2013 March; 180(1):21-6; Peters et al, J Pharmacol Exp Ther. 2013 January; 344(1):2-7; Martinez-Moya et al, Pharmacol Res. 2012 August; 66(2):144-53; Pickkers et al, Crit Care. 2012 Jan. 23; 16(1); Ramasamy et al, Inflamm Bowel Dis. 2011 February; 17(2):532-42; Lukas et al, Inflamm Bowel Dis. 2010 July; 16(7):1180-6; Bol-Schoenmakers et al, Eur J Pharmacol. 2010 May 10; 633(1-3):71-7; Heemskerk et al, Crit Care Med. 2009 February; 37(2):417-23; Tuin et al, Gut. 2009 March; 58(3):379-87; Su et al, Crit Care Med. 2006 August; 34(8):2182-7; van Veen et al, Br J Surg. 2006 April; 93(4):448-56; van Veen, Infect Immun. 2005 July; 73(7):4309-14; Verweij et al, Shock. 2004 August; 22(2): 174-9).

Although at present, alkaline phosphatases, isolated from natural sources as well as recombinantly engineered, are available that are useful in both diagnostics and disease treatment, there is a need for alternative phosphatases with for example an altered (for example improved) specific activity, stability (for example in vivo $T_{1/2}$, or stability in respect of storage (shelf-life)) or substrate specificity.

The present invention provides such modified phosphatases, which have improved properties compared to a chimeric recombinant alkaline phosphatase that is extensively described in WO2008/133511.

SUMMARY OF THE INVENTION

In a first embodiment, the invention provides an isolated protein having phosphatase activity, wherein said protein comprises an amino acid sequence of at least 200 consecutive amino acids having at least 90% sequence identity with SEQ ID NO: 5, an amino acid sequence of at least 50 consecutive amino acids having at least 90% sequence identity with SEQ ID NO: 6, and an amino acid sequence of at least 40 consecutive amino acids having at least 90% sequence identity with SEQ ID NO: 7, wherein the full length protein comprises an amino acid sequence having at least 90% sequence identity with the full length amino acid sequence of SEQ ID NO: 1, with the proviso that the amino acid at position 279 is leucine (L), the amino acid at position 328 is valine (V) and the amino acid at position 478 is leucine (L).

In a preferred embodiment, the full length protein comprises an amino acid sequence having at least 90%, at least 95%, or at least 98% sequence identity with the full length amino acid sequence of SEQ ID NO: 1, with the proviso that the amino acid corresponding to position 279 is leucine (L), the amino acid corresponding to position 328 is valine (V) and the amino acid corresponding to position 478 is leucine (L).

With the term "corresponding to" here, is meant the particular position, relative to the N-terminal amino acid of the mature protein, which is designated "position 1". The term "corresponding to" explicitly does not refer to the particular amino acid residue on that particular position.

The terms "protein" and "polypeptide" refer to compounds comprising amino acids joined via peptide bonds and may be used interchangeably.

As used herein, where "amino acid sequence" is recited it refers to an amino acid sequence of a protein or peptide molecule. An "amino acid sequence" can be deduced from the nucleic acid sequence encoding the protein. However, terms such as "polypeptide" or "protein" are not meant to limit the amino acid sequence to the deduced amino acid sequence, but can include posttranslational modifications of the deduced amino acid sequences, such as amino acid deletions, additions, and modifications such as glycosylations and addition of lipid moieties. Also the use of non-natural amino acids, such as D-amino acids to improve stability or pharmacokinetic behaviour falls within the scope of the term "amino acid sequence", unless indicated otherwise.

Preferably, part of said protein comprises an amino acid sequence of 50-65, preferably 60-65, more preferably 62-65, more preferably 64-65, most preferably 65 consecutive amino acids, having at least 90%, preferably at least 95%, more preferably at least 98% sequence identity with the full length crown domain of human PLAP. For the purpose of the present invention, the amino acid sequence corresponding to the full length crown domain of the human PLAP reference sequence is underlined in SEQ ID NO: 3, depicted in FIG. 1 and corresponds to positions 366-430 therein.

Preferably, part of said protein comprises an amino acid sequence of 200-365, more preferably 250-365, more preferably 300-365, more preferably 350-365, more preferably at least 360-365, most preferably 365 consecutive amino acids having 90%, preferably at least 95%, more preferably at least 98% sequence identity with the N-terminal region flanking the crown domain of human ALPI. This N-terminal region flanking the crown domain is considered one of two parts of the catalytic domain.

Preferably, part of said protein comprises an amino acid sequence of 40-54, preferably 45-54, more preferably 50-54, more preferably 52-54, most preferably 54 consecutive amino acids having 90%, preferably at least 95%, more preferably at least 98% sequence identity with the C-terminal region flanking the crown domain of human ALPI. This C-terminal region flanking the crown domain is considered the second of two parts of the catalytic domain.

For the purpose of the present invention, the amino acid sequence of the human ALPI mature protein reference sequence is depicted in FIG. 1 (SEQ ID NO: 2). For the purpose of determining the N-terminal and C-terminal flanking regions, together referred to as the catalytic domain, the crown domain of human ALPI is herein underlined.

In a particular preferred embodiment, the invention provides a protein according to the invention, wherein said protein comprises an amino acid sequence of 50-65, preferably 60-65, more preferably 62-65, more preferably 64-65, most preferably 65 consecutive amino acids, having at least 90%, preferably at least 95%, more preferably at least 98% sequence identity with the full length crown domain of human PLAP, part of said protein comprises an amino acid sequence of 200-365, more preferably 250-365, more preferably 300-365, more preferably 350-365, more preferably 360-365, most preferably 365 consecutive amino acids having at least 90%, preferably at least 95%, more preferably at least 98% sequence identity with the N-terminal region flanking the crown domain of human ALPI, and part of said protein comprises an amino acid sequence of 40-54, preferably 45-54, more preferably 50-54, more preferably 52-54, most preferably 54 consecutive amino acids having at least 90%, preferably at least 95%, more preferably at least 98% sequence identity with the C-terminal region flanking the crown domain of human ALPI.

With N-terminal flanking region of the crown domain is meant a stretch of amino acids adjacent (i.e. preferably less than 20 amino acids, more preferably less than 15, more preferably less than 10, more preferably less than 5, more preferably less than 3, more preferably less than 2, most preferably no amino acid apart) to the sequence of the crown domain (the corresponding amino acids thereof underlined in FIG. 1), at the left hand side of the crown domain, wherein the left hand side is defined as that part of the peptide chain carrying the amino (NH2) group of the first amino acid. With C-terminal flanking region of the crown domain is meant a stretch of amino acids corresponding to the positions adjacent (i.e. less than 20 amino acids, preferably less than 15, more preferably less than 10, more preferably less than 5, more preferably less than 3, more preferably less than 2, most preferably no amino acid apart) to the sequence of the crown domain (the corresponding amino acids thereof underlined in FIG. 1), at right hand side of the crown domain, wherein the right hand side is defined as that part of the peptide chain carrying the free alpha carboxyl group of the last amino acid.

In humans, four alkaline phosphatase isoforms have been identified so far. These are intestinal (ALPI), placental (ALPP), placental-like (GCAP), and liver/bone/kidney (or tissue non-specific) alkaline phosphatase (TNAP). The first three are located together on chromosome 2 while the tissue non-specific form is located on chromosome 1. The exact physiological functions of the APs are not known, but AP appears to be involved in a large number of physiological processes.

The sequence of human alkaline phosphatases is known in the art and can be easily found in the relevant databases. For determining the % sequence identity to the crown domain of PLAP and catalytic domain of ALPI, the respective reference sequences are preferably used. The reference sequence of human ALPI is depicted as SEQ ID NO: 2. The reference sequence of human ALPP is depicted as SEQ ID NO: 3. Within those reference sequences in FIG. 1, the sequence commonly known as the crown domain is underlined.

The placental alkaline phosphatase is herein abbreviated as ALPP or PLAP. The abbreviations ALPI or IAP refer to intestinal alkaline phosphatase. The placental-like 2 alkaline phosphatase is herein abbreviated as ALPP2, ALPG or GCAP and the abbreviations ALPL, TNSALP, TNAP or BLK are herein used to refer to liver/tissue non-specific alkaline phosphatase. The different abbreviations for one and the same alkaline phosphatase may be used interchangeably herein.

From a conformational point of view, an alkaline phosphatase roughly consists of two domains: a crown domain and an active-site domain (Mammalian Alkaline Phosphatases: From Biology to Applications in Medicine and Biotechnology. Jose Luis Millan; Wiley, 2006). The active-site domain can be divided in separate parts like the catalytic residue and three metal ion sites (Zn1, Zn2 and Mg3). From a primary structure point of view, it is clear that the crown domain is flanked by the amino acids that form the active site domain. Hence, in a preferred embodiment, the catalytic domain is not composed of a contiguous sequence of amino acids, but is flanking the crown domain. With reference to SEQ ID NO:1 which denotes the amino acid sequence of one alkaline phosphatase according to the invention, which does not limit the present invention in any way, the crown domain preferably comprises the amino acids on position 366-430, whereas the catalytic domain preferably refers to the remaining sequences before position 366 and after position 430 in the mature protein sequences as depicted in FIG. 1. The amino acid sequence of alkaline phosphatases and the relative positions of the catalytic and crown domain are known by the skilled person (Mammalian Alkaline Phosphatases: From Biology to Applications in Medicine and Biotechnology. José Luis Millan; Wiley, 2006).

In some embodiments, a protein according to the invention thus comprises a sequence having at least 90% sequence identity with the crown domain of a human ALPP and a sequence having at least 90% sequence identity with the catalytic domain of a human intestinal alkaline phosphatase. Preferably said sequence having said sequence identity to the crown domain of ALPP is situated in a protein according to the invention at approximately the same position as the crown domain of ALPP in the native ALPP protein, i.e. at approximately position 366-430, relative to position 1 as indicated in FIG. 1 (sequence representing the crown domain is underlined).

The sequence having sequence identity with the crown domain of ALPP preferably has at least 95%, more preferably at least 98%, most preferably 100% sequence identity with the native sequence of the crown domain of ALPP, which is represented by underlined amino acids on positions 366-430 in SEQ ID NO: 3.

The percentage of identity of an amino acid or nucleic acid sequence, or the term "% sequence identity", is defined herein as the percentage of residues in a candidate amino acid or nucleic acid sequence that is identical with the residues in a reference sequence after aligning the two sequences and introducing gaps, if necessary, to achieve the maximum percent identity. In a preferred embodiment, the calculation of said at least percentage of sequence identity is carried out without introducing gaps. Methods and computer programs for the alignment are well known in the art, for example "Align 2" or the BLAST service of the National Center for Biotechnology Information (NCBI).

Preferably said sequence having a sequence which is at least 90% identical to the N-terminal part flanking the crown domain of ALPI is situated in a protein according to the application at approximately the same position as that part of ALPI in the native ALPI protein, i.e. as represented by positions 1-365 in SEQ ID NO: 1 in FIG. 1.

Further, the sequence having sequence identity with the catalytic domain of ALPI preferably has at least 95%, more preferably at least 98% sequence identity with the N-terminal part flanking the crown domain of ALPI, represented by positions 1-365 in FIG. 1, SEQ ID NO: 2, with the proviso that the amino acid at position 279 is L and the amino acid corresponding to position 328 is V. Most preferably, the sequence having sequence identity with that N-terminal part of the catalytic domain of ALPI is identical to the native sequence of the catalytic domain of ALPI, with the exception that the amino acid at position 279 is L and the amino acid at position 328 is V.

Preferably said sequence having a sequence which is at least 90% identical to the C-terminal part flanking the crown domain of ALPI is situated in a protein according to the invention at approximately the same position as that part of ALPI in the native ALPI protein, i.e. as represented by positions 431-484 in SEQ ID NO: 1.

The sequence having sequence identity with the C-terminal part flanking the crown domain of ALPI preferably has at least 95%, more preferably at least 98% sequence identity with the C-terminal sequence, flanking the crown domain of ALPI and represented by positions 431-484 in SEQ ID NO: 2, with the proviso that the amino acid at position 478 is L. Most preferably, the sequence having sequence identity with that C-terminal part of the catalytic domain of ALPI is identical to the native sequence of the catalytic domain of ALPI, with the exception that the amino acid at position 478 is L.

Previously, it was shown that an alkaline phosphatase having a crown domain sequence which has sequence identity with the crown domain of ALPP and having a catalytic domain having a sequence identity with the catalytic domain of ALPI (herein referred to as catALPI/crownALPP) retained its initial specific activity in low $Zn^{2+}$ medium. These results showed that the in vivo activity is $Zn^{2+}$ independent. In comparison, ALPI quickly lost its activity under the same low $Zn^{2+}$ conditions. The inventors concluded that such an enzyme whose activity is independent of $Zn^{2+}$ could be useful in illnesses where $Zn^{2+}$ depletion is part of the pathology (e.g. nutritional defects, alcohol abuse and intestinal integrity damage, chronic infections including sepsis, or inflammatory diseases in general) or where addition of $Zn^{2+}$ (as a stabilizing agent in manufacture) may be contraindicated (e.g. acute phase of sepsis, autoimmune diseases). Apart from production and application advantages, catALPI/crownALPP also had advantages in respect to stability during storage. The properties of catALPI/crown ALPP are described in detail in WO2008/133511.

The current application surprisingly shows that a protein according to the present invention is even more stable at low $Zn^{2+}$ concentration. It is shown here, that a specific modification involving three positions with respect to the previously described catALPI/crownALPP sequence increases the $Zn^{2+}$ independency even more. In summary, it has thus been shown that native AP, such as ALPI, loses its enzymatic activity in environments with low $Zn^{2+}$ concentrations, catALPI/crownALPP (as described in WO2008/133511) retains its activity in environments with low $Zn^{2+}$ but loses its activity when, e.g. $Zn^{2+}$ chelating agents are added, whereas a protein according to the present invention retains much of its activity even in the presence of a zinc chelator, such as EDTA. Thus, in diseases wherein severe $Zn^{2+}$ depletion is part of the pathology, said native AP is unable to unfold its enzymatic activity at the site where it is thought to be the most beneficial, e.g. at the site of inflammation. In contrast, a recombinant AP not susceptible to very low $Zn^{2+}$ concentrations, in particular a protein according to the invention retains its activity in an environment with very low $Zn^{2+}$ concentration, e.g. at an inflammation site. Such enzyme is thus very useful for treatment of diseases that are due to or accompanied by low $Zn^{2+}$ levels. Such decreased $Zn^{2+}$ levels would render other alkaline phosphatases less active, as compared to a protein according to the invention.

Several enzymes in the human body depend on $Zn^{2+}$ for their activity and for instance immunologic responses are more effective if sufficient levels of $Zn^{2+}$ are present. The innate as well as the specific parts of the immune system are known to be influenced by zinc and it has been established that zinc containing proteins accumulate at sites of inflammation. In a healthy individual, $Zn^{2+}$ serum reference values are between 10 and 20 μM. For instance in alcohol abuse or during malnutrition, these levels can decrease to less than 10 μM or even less than 1 μM. Furthermore, (sub)chronic inflammation, such as rheumatoid arthritis, sepsis, and Crohn's disease present with serum zinc deficiency. In such $Zn^{2+}$ deficient environments, a protein according to the invention is still very active whereas other, known alkaline phosphatases more or less quickly lose their phosphatase activity.

The invention thus provides the insight that a protein according to the invention is especially useful in the treatment of a disease that is accompanied with local or systemic $Zn^{2+}$ deficiency. Compared to other known alkaline phosphatases, a protein according to the invention is more active under low $Zn^{2+}$ conditions. In preferred embodiment therefore, the invention provides a protein according to the invention for use in preventing or treating a disease which is accompanied by $Zn^{2+}$ deficiency. Preferably, said disease comprises an inflammatory disease, more preferably selected from the group consisting of autoimmune diseases, rheumatoid arthritis, asthma, chronic obstructive pulmonary disease, atherosclerosis, inflammatory disease of the gastrointestinal tract, infection, sepsis, neurodermatitis, inflammatory liver disease, inflammatory lung disease and inflammatory kidney disease.

With the term "zinc deficiency" or "$Zn^{2+}$ deficiency" is meant that the amount of zinc (locally) available is insufficient to enable unhindered cellular and/or enzymatic activity. Zinc deficiency can be absolute or relative, wherein absolute zinc deficiency can be easily determined by referring to reference values in healthy individuals, known in the art. Relative zinc deficiency, for instance, can occur when zinc concentrations are still within the boundaries set by reference values in healthy individuals, but zinc concentrations needed are higher than normal, for instance during inflammation. In some embodiments, zinc deficiency means that a subject's (local) zinc concentration is below 10 μM, more preferably below 5 μM, more preferably below 2 μM, more preferably below 1 μM, more preferably below 0.1 μM, more preferably below 0.05 μM, more preferably below 0.02 μM, more preferably below 0.01 μM, more preferably below 0.005 μM, most preferably below 0.002 μM. In some embodiments, zinc deficiency means that the (local) zinc concentration is lower than necessary for unhindered cellular and/or enzymatic activity.

With the term "inflammatory disease" is meant, any disease that is due to or accompanied by a protective tissue response to injury or destruction of tissues, which serves to destroy, dilute, or wall off both the injurious agent and the injured tissues. The classical signs of acute inflammation are pain (dolor), heat (calor), redness (rubor), swelling (tumor), and loss of function (functio laesa). Typically, inflammation is characterized by increase in inflammatory parameters, such as C-reactive protein, leucocytes and cytokines (IL-6, TNF-alpha, etc). Although the inflammation is initially protective by nature, deranged inflammatory disease, such as rheumatoid arthritis and (other) autoimmune diseases, also fall within the definition of "inflammatory disease". In a preferred embodiment, the protein of the present invention is for use in the treatment of such deranged or harmful inflammatory disease.

Further, during standard pharmacokinetic analysis, the present inventors have unexpectedly observed that a protein according to the invention is targeted to several organs, in particular skin, kidney, spleen, liver, lungs, brain, fat, bone, and colon. Using a radioactive iodine-coupled protein of the invention, it has been observed that the % organ/blood ratio for a protein according to the invention relative to that of catALPI/crownALPP is especially favourable for skin, kidney, spleen, liver, lungs, brain, fat, bone, and colon, i.e. a protein according to the invention is targeted relatively more to these organs than the known catALPI/crownALPP protein. In particular, a protein according to the invention resides in lower concentrations in the blood than catALPI/crownALPP and resides in higher concentrations in the mentioned organs. When a condition relating to these organs, such as liver neurodermatitis, kidney injury, liver fibroses, hypophosphatasia or the like is to be treated less protein is needed for treatment, reducing costs and/or increasing efficacy. Experiments involving diseases related to these organs have already been performed (hypophosphatasia), are in progress (kidney disease), or are planned. The invention thus provides a protein which shows improved zinc independency and pharmacokinetic behaviour when compared to alkaline phosphatases known in the art.

The inventors have shown, in various working embodiments, that a protein according to the invention is useful as a medicament. Diseases or conditions that can be treated with a protein according to the invention include: reduced renal function, kidney injury, renal failure and hypophosphatasia. Further, because of specific features of an alkaline phosphatase protein according to the invention which constitute improvements over known alkaline phosphatase proteins that have been used, the protein according to the invention is useful not only for reduced renal function, kidney injury, renal failure and hypophosphatasia, but also for the prevention or treatment of autoimmune diseases, rheumatoid arthritis, asthma, chronic obstructive pulmonary disease, atherosclerosis, inflammatory disease of the gastrointestinal tract, infection, sepsis, neurodermatitis, inflammatory liver disease, inflammatory lung disease and inflammatory kidney disease. These are all diseases affecting organs which are targeted by a protein according to the invention and/or are accompanied by (relative) zinc deficiency.

The term "prevention" or "preventing" is herein defined as the (the act of) administering a protein according to the invention to a subject with the intention to prevent said subject of attracting a particular disease. Although the intention of treatment is to prevent said subject attracting said disease, it is not necessary that the disease state is completely prevented after one or multiple administration(s) of a protein according to the invention, as subjects are, e.g., not necessarily susceptible for a specific treatment protocol. It is preferred that, overall, efficacy of said prevention is achieved in that a group of subjects that has received a protein according to the invention for preventing a particular disease shows at least a reduced increase in disease-severity or e.g. less complications of said disease, when compared with a group of subjects that has not received said protein. For instance in case of renal disease, it is preferred that subjects at risk of attracting renal disease, after being treated with a protein according to the invention show less decline in renal function, relative to subjects that have not been treated with said protein. If a subject attracts a disease for which a protein was administered in order to prevent said disease, further administrations may either be given (herein referred to as "treatment") to prevent worsening of said disease states or as treatment with the intention to cure.

The term "treatment" or "treating" is herein defined as (the act of) administering a protein according to the invention to a subject with the intention to cure the subject of an (expected) illness or improve, reduce, or remove the symptoms of an illness in the subject. Although the intention of treatment is to cure said subject, it is not necessary that said subject is cured after one or multiple administration(s) of a protein according to the invention, as subjects are, e.g., not necessarily susceptible for a specific treatment protocol. It is preferred that, overall, efficacy of said treatment is achieved in that subjects having been treated with a protein according to the invention show at least an improvement of their disease-condition or e.g. less complications of said disease, when compared with a non-treated (or placebo treated) group. For instance in case of renal disease, it is preferred that subjects, after being treated with a protein according to the invention show improved renal function or less decline in renal function, relative to subjects that have not been treated with said protein.

The invention further provides a polynucleotide comprising a nucleotide sequence encoding a protein according to the invention.

As used herein, the terms "nucleic acid sequence" and "polynucleotide" also encompass non-natural molecules based on and/or derived from nucleic acid sequences, such as for instance artificially modified nucleic acid sequences, peptide nucleic acids, as well as nucleic acid sequences comprising at least one modified nucleotide and/or non-natural nucleotide such as for instance inosine, LNA, Morpholino, and 2'-O-methyl RNA.

Also provided is a vector comprising such polynucleotide according to the invention. Such a vector preferably comprises additional nucleic acid sequences such as elements necessary for transcription/translation of the nucleic acid sequence encoding a phosphatase (for example promoter and/or terminator sequences). Said vector can also comprise nucleic acid sequences coding for selection markers (for example an antibiotic) to select or maintain host cells transformed with said vector. Examples of suitable vectors are cloning or expression vectors. Any vector suitable for mediating expression in a host cell of choice may be used according to the invention, either integrated or episomally replicating in a host cell. The vector can be a plasmid, a virus (for example a retrovirus, adenovirus, adeno-associated virus, baculovirus and/or derivatives thereof), a cosmid, a phage or a phagemid, an episomal vector or an artificial chromosome. Such polynucleotide or vector is very useful for the production of a protein according to the invention, but can also be used for gene therapy.

The invention thus provides a protein according to the invention for use as a medicament. It is also possible to treat a patient suffering from or at risk of suffering from any one of the above mentioned disease to be treated with a polynucleotide according to the invention, or with a vector according to the invention, in order to express a protein according to the invention in vivo. The invention thus also provides a polynucleotide according to the invention or a vector according to the invention for use as a medicament, preferably for the prevention or treatment of reduced renal function, kidney injury, renal failure, hypophosphatasia autoimmune diseases, rheumatoid arthritis, asthma, chronic obstructive pulmonary disease, atherosclerosis, inflammatory disease of the gastro-intestinal tract, infection, sepsis, neurodermatitis, inflammatory liver disease, inflammatory lung disease and inflammatory kidney disease.

Also provided is a protein, a polynucleotide or a vector according to the invention for use in a method for the prevention or treatment of an inflammatory disease, a kidney disease or hypophosphatasia.

Also provided is the use of a protein, polynucleotide and/or vector for according to the invention for the manufacturing of a medicament, preferably for the prevention or treatment of reduced renal function, kidney injury, renal failure, hypophosphatasia, autoimmune diseases, rheumatoid arthritis, asthma, chronic obstructive pulmonary disease, atherosclerosis, inflammatory disease of the gastro-intestinal tract, infection, sepsis, neurodermatitis, inflammatory liver disease, inflammatory lung disease and inflammatory kidney disease.

In another embodiment, the invention provides the use of an alkaline phosphatase protein according to the invention, of a polynucleotide according to the invention, or of a vector according to the invention, in the preparation of a medicament for the treatment of a disease which is accompanied by a local or systemic $Zn^{2+}$ deficiency, preferably said disease is an inflammatory disease, a kidney disease or hypophosphatasia, preferably said disease comprises an inflammatory disease, more preferably a disease selected from the group consisting of autoimmune diseases, rheumatoid arthritis, asthma, chronic obstructive pulmonary disease, atherosclerosis, inflammatory disease of the gastro-intestinal tract, infection, sepsis, neurodermatitis, inflammatory liver disease, inflammatory lung disease and inflammatory kidney disease.

In yet another embodiment, the invention provides a method for treating a subject (preferably a human) to treat a disease which is preferably accompanied by $Zn^{2+}$ deficiency, comprising administering an effective amount of a phosphatase according to the invention, wherein said disease preferably comprises an inflammatory disease, more preferably selected from the group consisting of autoimmune diseases, rheumatoid arthritis, asthma, chronic obstructive pulmonary disease, atherosclerosis, inflammatory disease of the gastro-intestinal tract, infection, sepsis, neurodermatitis, inflammatory liver disease, inflammatory lung disease and inflammatory kidney disease.

The invention thus provides a protein, polynucleotide, and/or vector according to the invention for use in a variety of disease. A protein according to the invention is especially useful, because of its organ distribution, for use in treating a disease involving the gastro-intestinal tract, kidney skin, liver, lung, brain, fat tissue, or bone.

In one preferred embodiment, the invention provides a protein, polynucleotide and/or vector according to the invention for use in treating kidney disease.

Although there is continuing insight in the pathophysiology of kidney injury and there are therapies that improve renal function [Lameire N H, Acute kidney injury: an increasing global concern. Lancet. 2013 Jul. 13; 382(9887): 170-9], there is still a need for alternative treatments to treat kidney injury and/or improve renal function. The present invention provides such alternative treatment by providing a protein, polynucleotide and/or a vector for use according to the invention.

In a preferred embodiment, the invention provides a protein, polynucleotide and/or vector for use according to the invention, wherein said kidney disease is selected from the group of renal failure, acute kidney injury, chronic kidney disease, ischemic renal disease.

The term acute kidney injury (AKI), previously called acute renal failure, means that kidney function is rapidly lost. AKI is diagnosed on the basis of characteristic laboratory findings, such as elevated blood urea nitrogen and creatinine, or inability of the kidneys to produce sufficient amounts of urine. AKI can be subdivided in prerenal AKI, intrinsic AKI and postrenal AKI.

Prerenal AKI is caused by decreased effective blood flow to the kidney. Typical laboratory findings for prerenal AKI are: $U_{osm}$: >500, $U_{Na}$: <10, $Fe_{Na}$: <1% and BUN/Cr ratio: >20.

The term intrinsic AKI is used when sources of damage to the kidney itself are the cause. Typical laboratory findings for intrinsic AKI are: $U_{osm}$: <350, $U_{Na}$: >20, $Fe_{Na}$: >2% and BUN/Cr ratio: <15.

The term postrenal AKI is reserved for those conditions were urinary tract obstruction is the cause of AKI. Typical laboratory findings for postrenal AKI are: $U_{osm}$: <350, $U_{Na}$: >40, $Fe_{Na}$: >4% and BUN/Cr ratio: >15.

Worldwide, there are several guidelines for classification of chronic kidney disease. As one example, the classification criteria of the National Kidney Foundation (2002) "K/DOQI clinical practice guidelines for chronic kidney disease" are described below. The skilled person may select different patient populations, based on other guidelines.

Typically, all individuals with a glomerular filtration rate (GFR)<60 mL/min/1.73 m2 for 3 months are classified as having chronic kidney disease, irrespective of the presence or absence of kidney damage. The rationale for including these individuals is that reduction in kidney function to this level or lower represents loss of half or more of the adult level of normal kidney function, which may be associated with a number of complications. Generally individuals with chronic kidney damage are classified as having chronic kidney disease, irrespective of the level of GFR. The rationale for including individuals with GFR>60 mL/min/1.73 m2 is that GFR may be sustained at normal or increased levels despite substantial kidney damage and that patients with kidney damage are at increased risk of the two major outcomes of chronic kidney disease: loss of kidney function and development of cardiovascular disease, which may lead to morbidity and mortality.

The loss of protein in the urine is regarded as an independent marker for worsening of renal function and cardiovascular disease. Hence, British guidelines append the letter "P" to the stage of chronic kidney disease if there is significant protein loss.

The 5 stages of chronic kidney disease are typically classified as follows:

Stage 1: Slightly diminished function; kidney damage with normal or relatively high GFR (≥90 mL/min/1.73 m2). Kidney damage is defined as pathological abnormalities or markers of damage, including abnormalities in blood or urine test or imaging studies.

Stage 2: Mild reduction in GFR (60-89 mL/min/1.73 m2) with kidney damage. Kidney damage is defined as pathological abnormalities or markers of damage, including abnormalities in blood or urine test or imaging studies.

Stage 3: Moderate reduction in GFR (30-59 mL/min/1.73 m2). British guidelines distinguish between stage 3A (GFR 45-59) and stage 3B (GFR 30-44) for purposes of screening and referral.

Stage 4: Severe reduction in GFR (15-29 mL/min/1.73 m2) Preparation for renal replacement therapy.

Stage 5: Established kidney failure (GFR<15 mL/min/1.73 m2), permanent renal replacement therapy (RRT), or end stage renal disease (ESRD).

The term renal failure now denotes a medical condition in which the kidneys fail to adequately filter waste products from the blood. The two main forms are acute kidney injury, which is often reversible with adequate treatment, and chronic kidney disease, which is often not reversible.

Ischemic renal disease is reserved for those conditions in which a clinically important reduction in glomerular filtration rate or loss of renal parenchyma is caused by hemodynamically significant renal artery stenosis or other causes that result in low blood pressure in the kidneys, such as e.g. hemodynamic shock or the use of an arterial clamp for temporary interruption of blood flow.

The inventors have also shown that a protein according to the invention is useful in the treatment of hypophosphatasia (HPP). This was quite unexpected, as previous experiments using TNAP for the treatment of hypophosphatasia failed to show efficacy of enzyme replacement therapy. Consequently an artificial fusion protein between a TNAP enzyme and a bone homing peptide was developed (Whyte et al, N Engl J Med. 2012 Mar. 8; 366(10):904-13). Surprisingly, the protein according to the present invention does not need such bone homing peptide and is able to effectively reduce the signs of symptoms of hypophosphatasia in a mouse model. In another preferred embodiment, the invention thus provides a protein, polynucleotide and/or vector according to the invention for use in treating hypophosphatasia.

The metabolic basis of hypophosphatasia stems from a molecular defect in the gene encoding tissue non-specific alkaline phosphatase (TNAP). TNAP is an ectoenzyme tethered to the outer surface of osteoblast and chondrocyte cell membranes. TNAP normally hydrolyzes several substances, including inorganic pyrophosphate (PPi) and pyridoxal 5'-phosphate (PLP) a major form of vitamin B6.

When TNAP is low, inorganic pyrophosphate (PPi) accumulates extracellularly and potently inhibits formation of hydroxyapatite (mineralization) causing rickets in infants and children and osteomalacia (soft bones) in adults. PLP is the principal form of vitamin B6 and must be dephosphorylated by TNAP to pyridoxal (PL) to cross over the cell membrane. Vitamin B6 deficiency in the brain impairs synthesis of neurotransmitters, which can cause seizures. In some cases, deposition of calcium pyrophosphate dehydrate (CPPD) crystals in the joint can cause pseudogout.

There are no approved therapies for HPP today. Current management consists of palliating symptoms, maintaining calcium balance and applying physical, occupational, dental and orthopedic interventions as necessary. Bisphosphonate (pyrophosphate synthetic analog) administration in one infant had no discernible effect on the skeleton, and the infant's disease progressed until death at 14 months of age.

Bone marrow cell transplantation in two severely affected infants produced radiographic and clinical improvement, although the mechanism of efficacy is not fully understood and significant morbidity remained. Enzyme replacement therapy with normal serum or with ALP-rich serum from patients with Paget's bone disease was not beneficial [Whyte M P, Valdes R, Ryan L M, McAlister W H (September 1982). "Infantile hypophosphatasia: enzyme replacement therapy by intravenous infusion of alkaline phosphatase-rich plasma from patients with Paget bone disease". J. Pediatr. 101 (3): 379-86][Whyte M P, McAlister W H, Patton L S, et al. (December 1984). "Enzyme replacement therapy for infantile hypophosphatasia attempted by intravenous infusions of alkaline phosphatase-rich Paget plasma: results in three additional patients". J. Pediatr. 105 (6): 926-33]. These enzyme replacement therapies were thought to be ineffective because the alkaline phosphatase function is supposed to be at the bone surface and not in the blood. Further attempts to improve the efficacy of enzyme replacement therapy were therefore built around a bone targeted TNAP enzyme with promising results [Whyte et al. N Engl J Med. 2012 Mar. 8; 366(10):904-13]. Surprisingly, the present invention shows that, without introducing an artificial bone-targeting moiety, a protein according to the invention is beneficial in a murine model of hypophosphatasia. One advantage of the present protein over that described in Whyte et al and Millan et al [J. Bone Miner. Res. 2008; 23(6):777-787] is that, because of the absence of the artificial bone targeting moiety, the present protein is expected to be much less immunogenic. The present protein consists of a protein having high sequence identity with naturally occurring human alkaline phosphatase proteins. Furthermore, the protein of the present invention has an advantage over the bone-targeted alkaline phosphatase with respect to ease and cost of production.

In a preferred embodiment, a protein, polynucleotide, and/or vector according to the invention for use in the treatment of hypophosphatasia is provided, wherein said hypophosphatasia is selected from perinatal hypophosphatasia, infantile hypophosphatasia, childhood hypophosphatasia, and adult hypophosphatasia.

Perinatal hypophosphatasia is the most pernicious form of hypophosphatasia. In utero, profound hypomineralization results in caput membraneceum, deformed or shortened limbs during gestation and at birth and rapid death due to respiratory failure.

Infantile hypophosphatasia presents in the first 6 months of life. Postnatal development often appears normal until the onset of poor feeding and inadequate weight gain, and clinical manifestations of rickets are recognized. Hypercalcemia and hypercalcinuria are also common and may explain the nephrocalcinosis, renal compromise, and episodes of recurrent vomiting. Mortality is estimated to be 50% in the first year of life.

Hypophosphatasia in childhood has variable clinical expression. As a result of aplasia, hypoplasia, or dysplasia of dental cementum, premature loss of deciduous teeth (i.e. before the age of 5) occurs. Frequently, incisors are shed first; occasionally almost the entire primary dentition is exfoliated prematurely. Dental radiographs sometimes show the enlarged pulp chambers and root canals characteristic of the "shell teeth" of rickets. Patients may also experience delayed walking, a characteristic waddling gait, complain of stiffness and pain, and have an appendicular muscle weakness (especially in the thighs) consistent with non-progressive myopathy. Typically, radiographs show rachitic deformities and characteristic bony defects near the ends of major long bones (i.e. "tongues" of radiolucency projecting from the rachitic growth plate into the metaphysis). Growth retardation, frequent fractures and osteopenia are common. In severely affected infants and young children it is not uncommon, despite the appearance of widely "open" fontanels on radiographic studies, for functional synostosis of cranial sutures to occur. The illusion of "open" fontanels results from large areas of hypomineralized calvarium. Subsequently true premature bony fusion of cranial sutures may elevate intracranial pressure.

Adult hypophosphatasia can be associated with rickets, premature loss of deciduous teeth, or early loss of adult dentition followed by relatively good health. Osteomalacia manifests in painful feet resulting from recurrent poorly healing metatarsal stress fractures, and discomfort in the thighs or hips due to femoral pseudofractures which, when they appear in radiographic study, are distinguished from most other types of osteomalacia (which occur medially) by their location in the lateral cortices of the proximal femora. Some patients suffer from calcium pyrophosphate dihydrate crystal depositions with occasional overt attacks of arthritis (pseudogout), which appears to be the result of elevated endogenous inorganic pyrophosphate (PPi) levels. These patients may also suffer articular cartilage degeneration and pyrophosphate arthropathy. Radiographs may reveal pseudofractures in the lateral cortices of the proximal femora, stress fractures, and patients may experience osteopenia, chondrocalcinosis, features of pyrophosphate arthropathy, and calcific periarthritis.

In a preferred embodiment, a protein, polynucleotide, and/or vector for use in the treatment of hypophosphatasia according to the invention is provided, wherein the treatment results in prolonged survival; increased body weight; improved skeletal phenotype (such as induction of secondary ossification centres, improvement of bone mineralization, for instance in trabecular and/or cortical bone, or induction of osteoid); attenuation of craniofacial defects (such as shape abnormalities and coronal suture fusion); improvement of dento-alveolar phenotype (such as improvement of molar height and form, dentin-thickness, and bone mineralization); and/or reduction of plasma PPi levels of the patient.

Also provided is the use of a protein, polynucleotide, and/or vector according to the invention for the preparation of a medicament for the prevention or treatment of hypophosphatasia, wherein the treatment results in prolonged survival; increased body weight; improved skeletal phenotype (such as induction of secondary ossification centres, improvement of bone mineralization, for instance in trabecular and/or cortical bone, or induction of osteoid); attenuation of craniofacial defects (such as shape abnormalities and coronal suture fusion); improvement of dento-alveolar phenotype (such as improvement of molar height and form, dentin-thickness, and bone mineralization); and/or reduction of plasma PPi levels of a patient.

Also provided is a method for treating a subject suffering or at risk of suffering from hypophosphatasia, wherein the treatment results in prolonged survival; increased body weight; improved skeletal phenotype (such as induction of secondary ossification centres, improvement of bone mineralization, for instance in trabecular and/or cortical bone, or induction of osteoid); attenuation of craniofacial defects (such as shape abnormalities and coronal suture fusion); improvement of dento-alveolar phenotype (such as improvement of molar height and form, dentin-thickness, and bone mineralization); and/or reduction of plasma PPi levels in said subject.

In a more preferred embodiment, a protein, polynucleotide, and/or vector for use in the treatment of hypophosphatasia according to the invention is provided, wherein said hypophosphatasia is selected from infantile, childhood or adult hypophosphatasia. More preferably, the hypophosphatasia is infantile hypophosphatasia.

Throughout the specification, examples and literature in the art, other nomenclature is used to designate the respective isoforms of alkaline phosphatase. For the sake of clarity, in Table 1 below the names and abbreviations commonly used, or used in this application are listed.

TABLE 1 synonyms and abbreviations used in the present patent application or generally known for the different types of alkaline phosphatases

| ALKALINE PHOSPHATASES | ABBREVIATIONS |
|---|---|
| Placental alkaline phosphatase | ALPP, PLAP, |
| Secretable Placental alkaline phosphatase | shPLAP, sALPP |
| Intestinal alkaline phosphatase | ALPI, IAP hIAP |
| Secretable Intestinal alkaline phosphatase | shIAP, sALPI |
| Placental-like alkaline phosphatase | GCAP |
| Tissue nonspecific alkaline phosphatase | TNAP, BLK, ALPL, TNSALP |
| Recombinant alkaline phosphatase comprising the catalytic domain of ALPI and the crown domain of ALPP | catALPI/crownALPP, RecAP, Xinplap, sALPI-ALPP-CD |
| Protein according to the invention | LVL-RecAP, improved RecAP |

With the term "secretable" is meant that no posttranslational Glycosylphosphatidylinositol (GPI) anchor has been attached to mature protein, enabling the protein to be secreted and not membrane bound. A GPI anchor is a glycolipid that can be attached to the C-terminus of a protein during posttranslational modification. It is composed of a phosphatidylinositol group linked through a carbohydrate-containing linker (glucosamine and mannose to the inositol residue through a glycoside bond) and via an ethanolamine phosphate (EtNP) bridge to the C-terminal amino acid of a mature protein. The two fatty acids within the hydrophobic phosphatidylinositol group anchor the protein to the cell membrane. It is advantageous for production and downstream processing, and thus preferred that a protein according to the invention does not comprise a GPI anchor.

It is clear that any of the described secretable modified phosphatases (and thus also a secretable protein according to the invention) can for example be produced by introducing into a host cell a nucleic acid capable of encoding said secretable phosphatase in operable linkage with regulatory sequences and allowing said host cell to express said secretable phosphatase and optionally isolating the produced phosphatase from the medium in which the host cell are grown and/or maintained. However, apart from mutations in the above-mentioned GPI-attachment sequence, other methods exist that make GPI-anchorless, secreted proteins, e.g.:

1) After expression as membrane-anchored proteins, phospholipases may be used to cleave off the GPI anchor. Hence the invention also provides a method for producing a secreted phosphatase comprising culturing a host capable of expressing a membrane anchored phosphatase, allowing said host cell to produce said phosphatase and incubating the obtained cells with a phospholipase and optionally isolating the released phosphatase.
2) Interference with the production of the GPI anchor or the use of a cell (type) that is deficient in GPI anchor production may also be used to make a secretable form of an otherwise GPI-anchored protein. Examples of cell lines that have been made to be deficient in GPI anchoring biochemistry are e.g. Jurkat, AM-B, C84, BW, S49, CHO and Raji. In yet another embodiment the invention therefore provides a method for producing a secreted phosphatase comprising culturing a host cell capable of expressing a secretable (alkaline) phosphatase (for example a host cell comprising a nucleic acid sequence encoding any of the mentioned modified secreted (alkaline) phosphatases), allowing said host to produce said secretable phosphatase and optionally isolating the produced phosphatase, wherein said host cell is not capable of biosynthesis of functional GPI anchored proteins. However, the host cell may also produce a phosphatase with a functional GPI signal sequence.
3) Interference with or the use of a cell deficient in transamidases may be used to inhibit attachment of a GPI anchor to the protein, rendering the protein anchorless and secretable. Such a deficient cell has been obtained through mutagenesis in CHO.

A vector according to the invention preferably comprises additional nucleic acid sequences such as elements necessary for transcription/translation of the nucleic acid sequence encoding a phosphatase (for example promoter and/or terminator sequences). Said vector can also comprise nucleic acid sequences coding for selection markers (for example an antibiotic) to select or maintain host cells transformed with said vector. Preferably, a nucleotide sequence encoding for a GPI anchor sequence is absent in a polynucleotide and/or vector according to the invention. Examples of suitable vectors are cloning or expression vectors. Any vector suitable for mediating expression in a suitable host cell may be used according to the invention, either integrated or episomally replicating in a host cell. The vector can be a plasmid, a virus (for example a retrovirus, adenovirus, adeno-associated virus, baculovirus or derivatives thereof), a cosmid, a phage or a phagemid, an episomal vector or an artificial chromosome.

Furthermore the invention also provides a host cell comprising a protein, a nucleic acid sequence or vector according to the invention as described. The cell can be a eukaryotic cell, preferably a mammalian cell, a plant cell or a yeast cell, that is suitable for production of recombinant proteins. Suitable yeast host cells comprise, e.g., *Saccharomyces cerevisiae* and *Pichia pastoris*. Preferred host cells are mammalian (or more preferred human) derived cells such as BHK, HEK293, CHO or PerC6™. In a particular preferred embodiment, the host cell is a CHO cell.

A nucleic acid sequence encoding a protein according to the invention, a vector comprising said nucleic acid sequence, and/or a host cell comprising said nucleic acid sequence are very useful in the production of a protein according to the invention. A protein according to the invention comprises glycosylation sites and hence the protein is preferably produced in cells that provide the desired glycosylation pattern. In a preferred embodiment, the used production system is a mammalian (for example human) in vitro production platform and even more preferably the production involves large-scale production. In another preferred embodiment, the used production system is a plant or yeast or mammalian (preferably non-human) platform in which an artificial human-like glycosylation pattern is introduced.

In one embodiment, the invention thus provides a method for producing a protein according to the invention, the method comprising culturing a host cell comprising a polynucleotide according to the invention or a vector according to the invention and allowing the host cell to produce said protein. Preferred host cells are mammalian (or more preferred human) derived cells such as BHK, HEK293, CHO or PerC6™. In a particular preferred embodiment, the host cell is a CHO cell. Preferably, a method for producing a protein according to the invention further comprises harvesting and optionally purifying said protein from said culture.

As already mentioned, a herein described protein according to the invention is useful in therapy. In one embodiment, the invention provides a composition, preferably a pharmaceutical composition, comprising a protein according to the invention. Said pharmaceutical composition optionally comprises a pharmaceutical acceptable carrier, diluent or excipient.

The composition can be presented in any form, for example as a tablet, as an injectable fluid or as an infusion fluid etc. Moreover, the composition, protein, nucleotide and/or vector according to the invention can be administered via different routes, for example intravenously, rectally, bronchially, or orally. Yet another suitable route of administration is the use of a duodenal drip.

In a preferred embodiment, the used route of administration is the intravenous route. It is clear for the skilled person, that preferably an effective amount of a protein according to the invention is delivered. As a start point, 1-50,000 U/kg/day can be used. Another suitable route, e.g., for HPP, is the subcutaneous route. If the intravenous route of administration is used, a protein according to the invention can be (at least for a certain amount of time) applied via continuous infusion.

Said composition according to the invention can optionally comprise pharmaceutically acceptable excipients, stabilizers, activators, carriers, permeators, propellants, desinfectants, diluents and preservatives. Suitable excipients are commonly known in the art of pharmaceutical formulation and may be readily found and applied by the skilled artisan, references for instance Remmington's Pharmaceutical Sciences, Mace Publishing Company, Philadelphia Pa., 17th ed. 1985.

For oral administration, the protein can, for example, be administered in solid dosage forms, such as capsules, tablets (e.g., with an enteric coating), and powders, or in liquid dosage forms, such as elixirs, syrups, and suspensions. AP can be encapsulated in gelatine capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable colour, taste, stability, buffering capacity, dispersion or other known desirable features are red iron oxide, silica gel, sodium lauryl sulphate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain colouring and flavouring to increase patient acceptance.

In a preferred embodiment, a composition comprising a protein according to the invention is suitable for oral administration and comprises an excipients coating to protect the AP from the adverse effects of gastric juices and low pH. Enteric coating and controlled release formulations are well known in the art. Enteric coating compositions in the art may comprise of a solution of a water-soluble enteric coating polymer mixed with the active ingredient(s) and other excipients, which are dispersed in an aqueous solution and which may subsequently be dried and/or pelleted. The enteric coating formed offers resistance to attack of a protein according to the invention by atmospheric moisture and oxygen during storage and by gastric fluids and low pH after ingestion, while being readily broken down under the alkaline conditions which exist in the lower intestinal tract.

The invention provides a composition according to the invention for use as a medicament, preferably for treating a disease accompanied by a local or systemic zinc deficiency, an inflammatory diseases, a kidney disease, or hypophosphatasia. The inflammatory disease preferably being selected from the group consisting of autoimmune diseases, rheumatoid arthritis, asthma, chronic obstructive pulmonary disease, atherosclerosis, inflammatory disease of the gastrointestinal tract, infection, sepsis, neurodermatitis, inflammatory liver disease, inflammatory lung disease and inflammatory kidney disease. The kidney disease preferably being selected from the group consisting of renal failure, acute kidney injury, chronic kidney disease, and ischemic renal disease. The hypophosphatasia preferably being selected from the group consisting of perinatal hypophosphatasia, infantile hypophosphatasia, childhood hypophosphatasia, and adult hypophosphatasia.

Besides the fact that a protein according to the invention can be incorporated in a pharmaceutical composition such a phosphatase can also be part of a nutritional composition or a nutraceutical.

A protein according to the invention can be added to a nutrient (such as milk) but can also be produced within said nutrient (for instance by molecular engineering). Moreover, tablets and/or capsules can be prepared which are subsequently added to a nutrient or which can be taken directly by a human being.

Further provided is a method for treating a subject suffering from an inflammatory disease, a kidney disease or hypophosphatasia, comprising administering an effective amount of a protein according to the application, e.g., an isolated or recombinant protein having phosphatase activity, wherein part of said protein comprises an amino acid sequence of at least 50 consecutive amino acids, having at least 90% sequence identity with the full length crown domain of human PLAP, part of said protein comprises an amino acid sequence of at least 200 consecutive amino acids having 90% sequence identity with the N-terminal region flanking the crown domain of human ALPI, and part of said protein comprises an amino acid sequence of at least 40 consecutive amino acids having 90% sequence identity with the C-terminal region flanking the crown domain of human ALPI., wherein the full length protein comprises an amino acid sequence having at least 90% sequence identity with the full length amino acid sequence of SEQ ID NO: 1, with the proviso that the amino acid on position 279 is leucine (L), the amino acid on position 328 is valine (V) and the amino acid on position 478 is leucine (L), or an effective amount of a polynucleotide according to the application or an effective amount of a vector according to the application.

The invention will be explained in more detail in the following, non-limiting examples.

FIGURE LEGENDS

FIG. 1: Amino acid sequences of mature protein LVL-RecAP, hIAP and hPLAP. The putative crown domains of the different proteins are underlined.

FIG. 2: Organ distribution of LVL-RecAP compared to catALPI/crownALPP. Depicted is the organ to blood distribution of LVL-RecAP divided by the organ to blood distribution of catALPI/crownALPP (=ratio of y-axis). A higher value is indicative of LVL-RecAP targeting the respective organ when compared to catALPI/crownALPP.

FIG. 3: Survival of Akp2$^{-/-}$ mice treated with either vehicle, 1 mg LVL-RecAP/kg/day, 8 mg LVL-RecAP/kg/day, or 16 mg LVL-RecAP/kg/day.

FIG. 4: Serum creatinine concentrations in piglets suffering from renal ischemic/reperfusion damage. Sham animals underwent the surgical procedure during which the left kidney was removed. However, renal occlusion and reperfusion were not conducted. In the group that received 0.32 mg/kg/day, on day 0, half of the dose was administered prior to reperfusion and the remaining half of the dose was administered at 8±2 hours post-reperfusion. A full dose was administered daily for the remainder of the in-life period.

FIG. 5: AP concentrations in piglets suffering from renal ischemic/reperfusion damage. Sham animals underwent the surgical procedure during which the left kidney was removed. However, renal occlusion and reperfusion were not conducted. In the group that received 0.32 mg/kg/day (200 U/kg/day), on day 0, half of the dose was administered prior to reperfusion and the remaining half of the dose was administered at 8±2 hours post-reperfusion. A full dose was administered daily for the remainder of the in-life period.

FIG. 6A-6D: Improvement of survival and body weight of Alpl$^{-/-}$ mice by LVL-RecAP treatment. 6A) LVL-RecAP16 survived to the end of the experiment. Average of survival was p19, p22 and p42.5 for Vehicle, LVL-RecAP1, and LVL-RecAP8, respectively. 6B) Alpl$^{-/-}$ vehicle treated mice are lighter than WT littermates; LVL-RecAP1 treatment improves body weight close to WT at p18. 6C) Vehicle treated mice do not survive longer and LVL-RecAP8 treated mice are still lighter than WT littermates at p53. 6D) Whereas LVL-RecAP16 treated mice present a body weight not significantly different from their WT littermates at p53.

FIG. 7A-7B: 7A) LVL-RecAP treatment improves the skeletal phenotype of Alpl$^{-/-}$ mice. Radiographs of spine, forelimb, rib cage, hindlimb and paws from Akp2$^{-/-}$ mice treated with vehicle, LVL-RecAP1, LVL-RecAP8, LVL-RecAP16, and untreated WT controls (magnification 5×). A) Akp2$^{-/-}$ mice display a severe osteomalacia (arrows) in vertebrae, long bones and rib cage. Secondary ossification centers are missing in Akp2$^{-/-}$ mice (asterisk). Treatment with LVL-RecAP1 slightly corrects that phenotype (arrowheads) compared to untreated WT at p18. 7B) Treatment with LVL-RecAP8 and LVL-RecAP16 clearly corrects the bone phenotype in vertebrae, long bones and rib cage. Specifically the distal most extremities are improved as the development of the secondary ossification centers in the metatarsal region demonstrates (arrowheads).

FIG. 8A-8C: 8A) Improved mineralization in LVL-RecAP-treated Alpl$^{-/-}$ mice. A) Histological analysis of femora of vehicle treated Alpl$^{-/-}$ (p18), LVL-RecAP8 (p51), LVL-RecAP16 p53, and untreated WT mice p53. Von Kossa staining revealed better bone mineralization with increased dosages LVL-RecAP8 and LVL-RecAP16. Secondary ossification centers and cortical bone region show a striking improvement in mineralization (black) compared with untreated. There is less trabecular bone in LVL-RecAP8 and LVL-RecAP16 compared to WT, but increased mineralization in the trabecular region as well as more osteoid, expected to become trabecular bone. 8B/8C) Analysis of BV/TV and OV/BV for LVL-RecAP8 and LVL-RecAP16 demonstrated less bone volume and higher osteoid volume than age-matched controls.

FIG. 9A-9C: Improvement of osteomalacia and plasma PP$_i$ levels in LVL-RecAP-treated Alpl$^{-/-}$ mice. 9A) Histological analysis of femora of vehicle treated Alpl$^{-/-}$ (p18), LVL-RecAP8 (p51), LVL-RecAP16 p53, and untreated WT mice p53. Goldner's Trichrome staining of the femora sections show severe osteomalacia in Alpl$^{-/-}$, and improved mineralization in the cortical area and in the secondary ossification with increased dosages LVL-RecAP8 and LVL-RecAP16. Presence of enlarged areas of osteoid, suggests deposition of bone, but not yet mineralized. 9B/9C) PP$_i$ concentrations in the plasma of Akp2$^{-/-}$ mice receiving LVL-RecAP1, LVL-RecAP16, and WT. LVL-RecAP1 treatment leads to a significant reduction of the elevated PP$_i$ levels in Alpl$^{-/-}$ mice at p18. At p53 LVL-RecAP16 treatment resulted in a correction of plasma PP$_i$ levels comparable to WT controls.

FIG. 10A-10F: Absence of craniofacial defects in LVL-RecAP-treated Alpl$^{-/-}$ mice. μCT isosurface images of WT (10A, 10D), vehicle-treated Alpl$^{-/-}$ (10B, 10E) and LVL-RecAP16 (10C, 10F) mouse skulls at p21 and p53, respectively. Neither frontal nor parietal bones of treated Alpl$^{-/-}$ mice were significantly different from those of WT mice. Adult skulls of LVL-RecAP16-treated Alpl$^{-/-}$ mice did not appear different from WT in terms of size and shape.

FIG. 11A-11Q: LVL-RecAP treatment partially rescues the dentoalveolar phenotype in Alpl$^{-/-}$ mice. Compared to (11A) radiography and (11D) μCT analysis of wild-type controls at p25-26, (11B, 11F) untreated Alpl$^{-/-}$ mouse mandibles feature hypomineralized and reduced alveolar bone (11A/11B), short molars (M1, M2, and M3) with thin dentin (11D/11E) and wide pulp chambers, and defective (white asterisk) incisor (INC) dentin. Compared to (11E) histology of control periodontal tissues, (11G) Alpl$^{-/-}$ mice exhibit no acellular cementum (11A/11C), and alveolar bone osteoid invades the PDL space, creating bone-tooth ankylosis (asterisk). (11C, 11H) LVL-RecAP8-treated Alpl$^{-/-}$ mice show improved radiographic appearance of molar height, dentin thickness, and bone mineralization, though the incisor teeth remain defective. (11I) Histologically LVL-RecAP does not restore acellular cementum to the root surface. Compared to (11J, 11L) controls at p53, (11K, 11M) LVL-RecAP16-treated Alpl$^{-/-}$ mice exhibit reduced alveolar bone mineralization around molar teeth. Molar form and mineralization appear relatively normal in treated Alpl$^{-/-}$ mice, while incisor teeth remain severely affected on the root analogue (white asterisk). Compared to histology of (11N) WT control molars, (11P) LVL-RecAP16-treated Alpl$^{-/-}$ mice feature a mix of mineralized alveolar bone and osteoid (asterisks), and a reduced but maintained PDL space. Poor periodontal attachment is evidenced by lack of cementum, PDL disorganization and detachment, and down growth of the junctional epithelium. Small regions of PDL attachment (chevron) to the tooth were noted. Compared to the strong and parallel organization of PDL collagen fibers in (11O) control tissues, indicated by picrosirius staining under polarized light, (11Q) LVL-RecAP16-treated Alpl$^{-/-}$ mice feature a less organized PDL, though regions of organization and attachment exist adjacent to breakthrough areas of tooth root attachment (white chevron).

FIG. 12A-12L: RecAP treatment attenuates the LPS-induced cytokine production in human proximal tubule epithelial cells (ciPTEC). CiPTEC were pre-treated with recAP (1-5-10 U/ml) followed by LPS-incubation (10 μg/ml) for 24 hrs and subsequently TNF-α, IL-6 and IL-8 production was measured (12A, 12B, 12C) on gene level in cells by qPCR (10 U/ml recAP) and (12D, 12E, 12F) on protein level in supernatant by ELISA. (12G, 12H, 12I) recAP (10 U/ml) was administered 2 hrs preceding LPS exposure, simultaneously with LPS or 2 hrs after LPS exposure, followed by measurement of TNF-α, IL-6 and IL-8 protein content. (12J, 12K, 12L) ciPTEC were pre-treated with inactive AP for 2 hrs, lacking hydrolyzing properties, followed by LPS incubation (10 μg/ml) for 24 hrs, whereafter TNF-α, IL-6 and IL-8 protein content was measured. Control cells were incubated with culture media. Data is expressed as mean±SEM (n=5), # p<0.05 compared to control, * p<0.05 compared to LPS.

FIG. 13A-13F: The effects of recAP are not restricted to LPS-induced inflammation and are renal specific. CiPTEC were pre-treated with recAP (10 U/ml) for 2 hrs followed by a 24-hour incubation with (13A, 13B) TNF-α (10 ng/ml) or (13C, 13D) supernatant of LPS-stimulated peripheral blood mononuclear cells (PBMCs, 1 ng/ml LPS), whereafter IL-6 and IL-8 production was measured on protein level by ELISA. (13E, 13F) PBMCs were preincubated for 2 hrs with recAP (10 U/ml) followed by LPS exposure (1 ng/ml) for 24 hrs. IL-6 and TNF-α production was measured by ELISA. Control cells were incubated with culture media. Data is expressed as mean±SEM (n=5), # p<0.05 compared to control, * p<0.05 compared to LPS.

FIG. 14: The effect of recAP on LPS-induced ATP release in vitro. ciPTEC were pre-treated with recAP (10 U/ml) followed by LPS-incubation (10 μg/ml or 100 μg/ml). After 30 minutes, supernatant was collected to determine cellular ATP release by bioluminescence. Control cells were incubated with culture media. Data is expressed as mean±SEM (n=5), # p<0.05 compared to control.

FIG. 15A-15D: RecAP prevents the LPS-induced deterioration of renal function in vivo. Renal function was assessed by the transcutaneous measurement of FITC-sinistrin $t_{1/2}$. AKI was induced in rats by LPS (0.3 mg/kg b.w., t=0), followed by recAP treatment (1000 U/kg b.w.) at t=2. $T_{1/2}$ measurements were performed at t=2 hrs and t=21.5 hrs (15A, 15B: examples of FITC-sinistrin kinetics obtained for one rat at the two respective time-points). Urine was collected between t=5 and t=16 and plasma was sampled at t=1.5 and t=24 hrs, allowing calculation of (15C) Fractional Urea excretion and (15D) Creatinine Clearance with the average plasma value of t=1.5 and t=24. Data is expressed as mean±SEM (Placebo, LPS n=6; LPS+recAP n=5), # p<0.05 compared to placebo.

FIG. 16A-16E: RecAP prevents renal injury during LPS-induced AKI in vivo. (16A) Urinary KIM-1 excretion and (16B) NGAL excretion, (16C) plasma NGAL levels (t=24), and (16D) renal KIM-1 protein content were determined by ELISA. (16E) Paraffin kidney sections were stained with anti-KIM-1 to visualize KIM-1 protein expression. Scale bars: 400 μm (left panel), 200 μm (right panel). Data is expressed as mean±SEM (Placebo, LPS n=6; LPS+recAP n=5; urinary parameters: Placebo n=5), # p<0.05 compared to placebo.

FIG. 17A-17C. No effect of recAP on LPS-induced cytokines in supernatant. Supernatant of 24 hrs LPS-incubated (10 μg/ml) or medium-incubated (Control) ciPTEC was collected, incubated with or without recAP (10 U/ml) for another 24 hrs followed by the measurement of TNF-α, IL-6 and IL-8 (17A, 17B, 17C) by ELISA. Data is expressed as mean±SEM, # p<0.05 compared to control, * p<0.05 compared to LPS.

FIG. 18. Correlation between enzyme activities of RecAP in human serum at 25° C. and at 37° C.

FIG. 19. Correlation between enzyme activities of LVL-RecAP in human serum at 25° C. and at 37° C.

FIG. 20 shows the activity/μg protein at 25° C. and at 37° C. for RecAP and LVL-RecAP. Values represent mean Δactivity between 25° C. and 37° C. for a given protein concentration.

EXAMPLES

Example 1

Stability of LVL-RecAP in buffer
Materials:
Human Recombinant Alkaline Phosphatases:
1. sALPI-ALPP-CD (SEQ ID NO: 4) (DOM: 4 Aug. 2008)
2. LVL-recAP (SEQ ID NO: 1) (DOM: 14 Oct. 2011)
Methods:
Zinc Dependency:

The enzyme activity and protein content of both human recombinant alkaline phosphatase batches were determined. Subsequently 100 μg/mL protein solutions were prepared for each condition to determine Zinc dependency for batches sALPI-ALPP-CD and LVL-recAP as outlined in Table 2.

The prepared samples were stored at RT and analysed for enzyme activity at T=0, T=2 h and T=24 h.

TABLE 2

Conditions of recombinant alkaline phosphatase batches sALPI-ALPP-CD and LVL-recAP to determine their stability (retained activity) in the presence and absence of Zinc and the influence of a chelator (EDTA).

| Condition | Zn (μM) | BSA (%) | Mg (mM) | Mannitol (%) | EDTA (mM) |
|---|---|---|---|---|---|
| 1 | 0 | 0 | 1 | 1 | 0 |
| 2 | 0.01 | 0 | 1 | 1 | 0 |
| 3 | 10 | 0 | 1 | 1 | 0 |
| 4 | 100 | 0 | 1 | 1 | 0 |
| 5 | 1000 | 0 | 1 | 1 | 0 |
| 6 | 0 | 0 | 1 | 1 | 2 |
| 7 | 0 | 0 | 1 | 1 | 5 |
| 8 | 0 | 0 | 1 | 1 | 10 |
| 9 | 0 | 0 | 1 | 1 | 100 |
| 10 | 50 | 0.025 | 1 | 1 | 0 |

Determinations of enzyme activities were according to standard procedures, as indicated in SOP PC001.

Protein concentrations were determined by OD280 measurements ($\varepsilon_{recAP}$ 1.01 mL/mg/cm $OD_{280}$)

Results

TABLE 3 activity of the different alkaline phosphatases under the conditions as specified in Table 2.

| | sALPI-ALPP-CD | | | LVL-RecAP | | |
|---|---|---|---|---|---|---|
| Diluent | t = 0 | t = 2 | t = 24 | t = 0 | t = 2 | t = 24 |
| 1 | 45.7 | 53.3 | 50 | 60.7 | 59.8 | 57.4 |
| 2 | 48.2 | 53.8 | 51.6 | 57.7 | 57.2 | 58.1 |
| 3 | 47.3 | 54.4 | 51.6 | 57.7 | 54.2 | 52.9 |
| 4 | 46.1 | 52 | 53.4 | 55.3 | 53.7 | 55.7 |
| 5 | 48.2 | 51.2 | 52.2 | 56.7 | 56.3 | 54.7 |
| 6 | 46.9 | 24.2 | 18.7 | 57.6 | 54.2* | 37.7* |
| 7 | 47 | 23.6 | 20.4 | 57.6 | 52.1* | 38.9* |
| 8 | 45 | 23.2 | 17.2 | 56.8 | 50.3* | 35.8* |
| 9 | 50.9 | 22.5 | 16.2 | 55.6 | 46.5* | 31.2* |
| 10 | 47.3 | 55.1 | 53.6 | 62.7 | 57.5 | 55.4 |

As clearly shown in Table 3, LVL-RecAP is considerably more stable (i.e. shows more residual enzyme activity; denoted by values with asterisks) in the presence of a metal chelating agent (EDTA) than sALPI-ALPP CD, implicating less dependency of $Zn^{2+}$ for its activity.

Example 2

Stability of LVL-RecAP in buffer
Materials:
Human Recombinant Alkaline Phosphatases:
1. sALPI-ALPP-CD (DOM: 4 Aug. 2008)
2. LVL-recAP (DOM: 14 Oct. 2011)
Methods In a second independent experiment, stability of sALPI-ALPP-CD and LVL-recAP were tested for several conditions as outlined in table 4. For both recombinant AP batches in this experiment 100 μg/mL protein solutions in 0.025M glycine buffer pH 9.6, human serum and human citrate plasma were prepared for each buffer condition to determine stability. All the prepared recombinant AP samples were incubated at 37° C. and analysed for enzyme activity at T=0, T=0.5 h, T=1 h, T=2 h and T=24 h.

TABLE 4

Conditions of recombinant alkaline phosphatase batches sALPI-ALPP-CD and LVL-recAP in glycine buffer to determine their stability (retained activity) in the presence/absence of Zinc and the influence of a Chelator (EDTA or Citrate).

| Condition | Zn (µM) | BSA % | Mg (mM) | Mannitol (%) | EDTA (mM) |
|---|---|---|---|---|---|
| 1 | 0 | 0 | 1 | 1 | 0 |
| 2 | 0 | 0 | 1 | 1 | 2 |
| 3 | 0 | 0 | 1 | 1 | 10 |
| 4 | 0 | 0 | 1 | 1 | 100 |
| 8 | 50 | 0.025 | 1 | 1 | 0 |

Results

TABLE 5 activity of the different alkaline phosphatases under the conditions as specified in Table 4.

| | LVL-recAP | | | | | sALPI-ALPP-CD | | | | |
|---|---|---|---|---|---|---|---|---|---|---|
| Condition | t = 0 | t = 0.5 | t = 1 | t = 2 | t = 24 | t = 0 | t = 0.5 | t = 1 | t = 2 | t = 240 |
| 1 | 55.1 | 57.7 | 54.9 | 55.2 | 55.8 | 63 | 52.5 | 53.8 | 53.8 | 55.2 |
| 2 | 59.5 | 52.5 | 52 | 51.6* | 37.7* | 56.5 | 48 | 51.6 | 36.3 | 23.3 |
| 3 | 50.9 | 53.5 | 51.6 | 49.2* | 35.2* | 3.3 | 44.7 | 43.7 | 32.9 | 18.9 |
| 4 | 49.3 | 43.9 | 48.7 | 41.3* | 24.2* | 49.8 | 37.9 | 34.6 | 29.4 | 13.3 |
| 8 | 12.2 | 49.3 | 53.9 | 53.1 | 52.1 | 55.9 | 56 | 57.9 | 57.5 | 56 |

Determinations of enzyme activities were performed according to SOP PC001. Protein concentrations were determined by OD280 measurements (εrecAP 1.01 mL/mg/cm OD280).

As clearly shown in Table 5 and in line with results in Table 3, LVL-RecAP is considerably more stable in the presence of a metal chelating agent (EDTA) than sALPI-ALPP CD (as denoted by values with asterisks), implicating less dependency of $Zn^{2+}$ for its activity.

Example 3

Heat Stability and PLP Kinetics of LVL-RecAP

Methods

Protein Expression

Expression plasmids containing secreted, FLAG epitope-tagged sALPI-PLAP-CD and LVL-RecAP were constructed as described previously (Kozlenkov et al. *J Biol Chem* 277, 22992-22999 (2002) and Kozlenkov et al. *J. Bone Miner. Res.* 19, 1862-1872 (2004)). The FLAG-tagged enzymes were transiently transfected into COS-1 cells by electroporation, then grown in DMEM medium for 24 h, as previously described (Narisawa et al. *Am. J. Physiol. Gastrointest. Liver Physiol.* 293, G1068-1077 (2007)) when the medium was replaced with serum-free Opti-MEM (Life Technologies). Opti-MEM containing secreted proteins was collected 60 hours after transfection, then filtered through a 2-µm cellulose acetate filter and dialyzed against TBS containing 1 mM $MgCl_2$ and 20 µM $ZnCl_2$.

Enzyme Kinetics

To measure the relative catalytic activities of FLAG-tagged enzymes, micro-titer plates were coated with anti-FLAG M2 antibody (Sigma-Aldrich) at 0.2-0.6 µg $mL^{-1}$. These plates were incubated with saturating concentrations of FLAG-tagged LVL-RecAP or sALPI-PLAP for 3 h at room temperature, after which plates were washed with PBS, containing 0.008% Tween-80 and the relative activities for PLP were compared for the M2-saturated enzymes.

Hydrolysis of the physiological substrate pyridoxal-5'-phosphate (PLP) (Sigma-Aldrich) was measured at pH 7.4 in standard assay buffer (50 mM Tris-HCl buffer, 100 mM NaCl, 1 mM $MgCl_2$ and 20 µM $ZnCl_2$). The concentration of released phosphate was determined using $P_i$ ColorLock Gold (Innova Biosciences) by measuring absorbance at 650 nm ($A_{650}$). Standard curves constructed for increasing concentrations of phosphate were linear between 0-50 µM and all experiments were designed to fall within this range of hydrolyzed phosphate concentrations. Molar reaction rates, expressed as $[P_i]$ $s^{-1}$ were calculated for the indicated substrate concentration range and were fitted to a one-binding site model (GraphPad Prism) versus [substrate] to calculate $K_m$ (Lineweaver-Burk plots were not applied, because of lack of precision of reciprocal conversions at very low substrate concentrations).

A substrate concentration for PLP of 400 µM was used. The soluble enzyme concentration was about 1 nM and incubation times ranged from 15-30 min, depending on the catalytic efficiency for each enzyme. To ensure steady-state conditions and to correct for non-specific substrate signals in the $P_i$ ColorLock Gold method, an early reading (at 5 min) was subtracted from the later reading, and $\Delta A_{650}$ was measured on the corresponding $P_i$ standard curve, constructed for each experiment separately. All experiments were carried out three to five times and the derived constants are reported as mean±SD.

To measure the heat stability, FLAG-tagged enzymes were incubated at 65° C. in 1 M DEA (pH 9.8) containing 1 mM $MgCl_2$ and 20 µM $ZnCl_2$. Samples were removed at different time points and placed on ice, then residual activity was measured using pNPP using the following method: The activity of bound enzymes was measured as the absorbance at 405 nm ($A_{405}$) as a function of time at 25° C., using pNPP (10 mM) as a substrate, at pH 7.4 in 50 mM Tris-HCl buffer, 100 mM NaCl, containing 1 mM $MgCl_2$ and 20 µM $ZnCl_2$. Enzymes were also incubated in this buffer for 10 min at increasing temperatures (25-100° C.) and residual activity was measured in the same manner.

Results

Production of FLAG-Tagged Enzymes

To compare the kinetic properties of LVL-RecAP with sALPI-PLAP, a FLAG-tag sequence was added to both cDNAs, as done previously to comparatively study PLAP and TNAP (Kozlenkov et al. *J Biol Chem* 277, 22992-22999 (2002) and Kozlenkov et al. *J. Bone Miner. Res.* 19, 1862-1872 (2004)). The cDNAs were expressed in COS-1 cells and culture supernatant containing secreted enzymes was recovered. Successful expression and recovery were confirmed by anti-FLAG antibody western blot analysis.

Kinetics Parameters with Physiological Substrates

The phosphohydrolase properties of LVL-RecAP and sALPI-PLAP were investigated for physiological substrates implicated in inflammation and seizures, specifically the vitamin $B_6$ vitamer PLP. LVL-RecAP showed lower Km than sALPI-PLAP (30.1 μM vs 60.7 μM) at physiologic pH (7.4), indicating that the improved LVL-RecAP has higher affinity for PLP than sALPI-PLAP at physiologic pH.

Enzyme Stability

The impact of the amino acid mutations in LVL-RecAP on the overall stability of the enzyme was investigated by heat inactivation studies. Although sALPI-PLAP has already highly improved heat resistance (50% inactivation at 77.8° C.), LVL-RecAP was even more resistant to heat inactivation (50% inactivation at 80.6° C.).

Example 4

Pharmacokinetic Distribution of LVL-RecAP in Rats

Part A Radiolabelling with Iodine-125

The sALPI-PLAP-CD protein and the LVL-RecAP protein were radiolabelled with Iodine-125 using the chloramine-T procedure as described by Greenwood et al.* The principle of labelling is based on the "in situ" oxidation of iodide to atomic iodine and its nucleophilic substitution into phenol rings in ortho position of the hydroxyl group of tyrosine residues.

The sALPI-PLAP protein was radioiodinated using the Chloramine-T technique in order to obtain ~0.5 mCi/mg final specific activity and ~1 mg/mL (NaCl 0.9%) final concentration.

*F. C Greenwood, V. M Hunter, H. G Glover, The preparation of 131I labelled growth hormone of high specific radioactivity, Biochem. J. 89 (1963) 114-123

A.1 Materials sALPI-PLAP Alkaline Phosphatase (496.7 U/mg) and LVL-RecAP (624 U/mg) was provided by AM-Pharma at 6.34 mg/mL concentration in 25% glycerol w/v, 5 mM Tris, 2 mM $MgCl_2$, 50 μM $ZnCl_2$, pH 8.0. sALPI-PLAP protein and LVL-RecAP protein were stored at 4° C.

Iodine-125 radionuclide was purchased from Perkin Elmer as sodium iodide in $10^{-5}$N sodium hydroxide (specific activity: 643.8 GBq/mg—radionuclide purity: 99.95%).

Chloramine-T (N-chloro-p-toluenesulfonamide, MW 227.6 g/mol), trichloroacetic acid, sodium metabisulfite (MW 190.1 g/mol) and tyrosine were purchased from Sigma.

Tris Buffer 5 mM pH 8 was prepared in Chelatec laboratory.

NaCl 0.9% was provided by Versol®.

A.2 Method

850 μg of protein, about 600 μCi of $Na^{125}I$, 50 μL of Tris buffer and 10 μL of chloramine-T (404.8 nmol, 50 equivalents/protein) were successively added in a 1.5 mL Lo-Bind eppendorf tube. The reaction was allowed to stir 1 minute at room temperature. 2 μL of the radiolabelling medium was mixed with MBS 5% solution and the radiolabelling efficiency was evaluated by Instant thin layer chromatography (ITLC) with 10% TCA as eluent (alkaline phosphatase at the bottom of the strip and free 125-iodine is eluted at the top of the strip).

After adding 30 μL of tyrosine solution (10 mg/mL in water) to the crude mixture, the iodinated sALPI-PLAP and iodinated LVL-RecAP were purified by gel filtration (G10, GE Healthcare) eluted with NaCl 0.9%. Fractions of 0.2 mL volume were collected in test tubes. Radioactivity in each fraction was measured in an automatic Gamma Counter calibrated for iodine-125 radionuclide (Wallace Wizard 2470—Perkin Elmer). The fractions containing the desired radioiodinated product were pooled. The radiochemical purity of the radiolabelled compound was verified by ITLC.

A.3 Results and Characteristic of Radiolabelled sALPI-PLAP Protein

The efficiency of radiolabelling determined by ITLC was over 85% for both proteins. After G10 purification, radiopurity of the labelling reaction is higher than 97% for both proteins.

The characteristics of radiolabelled sALPI-PLAP solution after G10 purification are summarized in Table 6.

TABLE 6

Characteristics of $^{125}$I-sALPI-PLAP solution after purification

|  | $^{125}$I-sALPI-PLAP | $^{125}$I-LVL-RecAP |
| --- | --- | --- |
| Labelling efficiency (ITLC) | 86.36% | 85.64% |
| G10 purification | | |
| Concentration (mg/mL) | 1.149 | 1.145 |
| Specific Activity (mCi/mg) | 0.669 | 0.544 |
| Volumic Activity (mCi/mL) | 0.791 | 0.637 |
| Radiopurity (%) | 97.23 | 97.8 |

A.4 Alkaline Phosphatase Activity

The enzymatic activity of radiolabelled sALPI-PLAP was assessed via ELISA.

Materials

Alkaline phosphatase colorimetric assay kit (reference ab83369—batch number: GR118166-3).

Unlabelled recombinant human alkaline phosphatase diluted at 0.25 mg/mL in NaCl 0.9%

Radiolabelled recombinant human alkaline phosphatase diluted at 0.25 mg/mL in NaCl 0.9%

Protocol

The Abcam kit uses p-nitrophenyl phosphate (pNPP) as a phosphatase substrate which turns yellow (Lamda max=405 nm) when dephosphorylated by AP. The kit can detect 10-250 μU AP in samples.

The alkaline phosphatase colorimetric assay was performed on unlabelled and radioiodinated sALPI-PLAP. The assay was performed as described in protocol provided by Abcam.

Briefly, a standard curve was generated from 0 to 20 nmol/well of pNPP standard (final volume: 120 μL). 10 μL of AP enzyme solution was added in each well. In parallel, the test sample of sALPI-PLAP was diluted 15000 and 8000 times in assay buffer. 10 and 20 μL of each dilution was added and the final volume was brought to 80 μL with assay buffer. Then, 50 μL of pNPP solution was added to each well containing the test sample.

The standard and sample reactions were incubated 60 min at 25° C. in the dark. All reactions were then stopped with 20 μL of stop solution. The O.D. at 405 nm was measured in a microplate reader.

pNP standard curve was plotted. The sample readings were applied to the standard curve to get the amount of pNP generated by AP sample. AP activity of the test samples can be calculated:

sALPI-PLAP activity (U/mL)=A/V/Tx dilution factor of test sample

A: amount of pNP generated by samples (in μmol)
V: volume of sample added in the assay well (in mL)
T: reaction time in minutes sALPI-PLAP activity (U/mg)=sALPI-PLAP activity
(U/mL)/concentration of sALPI-PLAP (mg/mL)

Results

Table 7 summarises the results.

TABLE 7

Enzymatic activity of unlabelled
sALPI-PLAP and $^{125}$I-ALPI-PLAP

| | sALPI-PLAP activity (U/mg) | | |
|---|---|---|---|
| | Dilution 1/15000 | Dilution 1/8000 | Mean |
| sALPI-PLAP | 474.6 | 471.6 | 473.1 |
| $^{125}$I-sALPI-PLAP | 482.6 | 475.3 | 479.0 |
| LVL-RecAP | 501.3 | 530.2 | 515.8 |
| $^{125}$I-LVL-RecAP | 539.2 | 588.5 | 563.8 |

The enzymatic activity of unlabelled and radiolabelled sALPI-PLAP is similar to about 475 U/mg. Thus, the activity of sALPI-PLAP is not compromised by the radioiodination using chloramine-T as oxidant.

Part B: Biodistribution Study of $^{125}$I-sALPI-PLAP Protein in Healthy Rats

B.1 Materials

The characteristics of the rat strain used in this study are presented below:

Species Sprague Dawley Rats
Strain Crl CD® (SD) IGS BR
Source Charles RIver France
Number and sex 15 males
Body weight range/age Approximately 250 g at the beginning of the study
Acclimation period Five days before treatment
Identification method Cage identification with the group (sacrifice time).
Animal Management
Husbandry: The rats were housed in animal facilities before treatment and in radioactivity room after treatment.
Food: Freely available rat diet. No fasting period before treatment.
Water: Tap water was delivered by polypropylene bottle ad libitum.
Housing Before treatment, animals were housed in groups of three in polycarbonate cages in standard conditions, identified by a card indicating the study number, the animal number, the sex, and the dates of beginning and end of the study. Animals designated for excretion balance were transferred in metabolism cages (one by cage) after treatment.
Environmental: The temperature was recorded every day. The temperature of the room was between 22 and 24° C. The artificial light cycle was controlled using an automatic timer (10 hours of light, 14 hours of dark).
Personnel: Associates involved were appropriately qualified and trained.
Selection: Animals were examined at receipt by the study director.
Only healthy animals were selected. Particular attention was paid to any sign of inflammatory reaction in the animals (e.g. abscess; skin inflammation etc).

B.2 Dosing Solution of $^{125}$I-sALPI-PLAP and 125I-LVL-RecAP

The Iodinated sALPI-PLAP and LVL-RecAP solutions were diluted at 0.25 mg/mL in NaCl 0.9% just prior to in vivo administration.

B.3 Study Design

The study design is presented in Tables 8 and 9.

TABLE 8

Study design for $^{125}$I-sALPI-PLAP in vivo distribution

| Group | Number of animals | Blood sampling time | Sacrifice time | Biodistribution |
|---|---|---|---|---|
| A1 | 3 males | 2 mn, 10 mn | 30 mn | Blood and organs |
| A2 | 3 males | 5 mn, 45 mn | 2 h | Blood and organs |
| A3 | 3 males | 15 mn, 4 h | 6 h | Blood and organs |
| A4 | 3 males | 1 h, 3 h, 18 h | 24 h | Blood and organs |
| A5* | 3 males | NA | 48 h | Blood and organs |

*housed individually in metabolism cages with urine and faeces collection at 24 h and 48 h

TABLE 9

Study design for $^{125}$I-LVL-RecAP in vivo distribution

| Group | Number of animals | Blood sampling time | Sacrifice time | Biodistribution |
|---|---|---|---|---|
| B1 | 3 males | 2 mn, 10 mn | 30 mn | Blood and organs |
| B2 | 3 males | 5 mn, 45 mn | 2 h | Blood and organs |
| B3 | 3 males | 15 mn, 4 h | 6 h | Blood and organs |
| B4 | 3 males | 1 h, 3 h, 18 h | 24 h | Blood and organs |
| B5* | 3 males | NA | 48 h | Blood and organs |

B.4 Administration

At the time of the experiment, the mean weight of the Sprague Dawley rats was about 240 g. Unanesthetized rats were injected intravenously in lateral tail vein (left) at a dose level of 400 μg/kg corresponding to a quantity of 96 μg protein per rat and an activity of about 58 μCi per rat. The volume of injection was about 380 μL. The individual dose volumes were calculated using individual body weight of each rat on the day of treatment. Rats were placed in a contention device. In order to dilate the tail blood vessels, the tail was dipped in warm water (45° C.) and then disinfected with alcohol. The dosing solution was slowly injected in the tail vein. In order to calculate the actual dose received by each rat, the syringes were weighed before and after treatment and an aliquot of dosing solution was counted in a Gamma Counter.

B.5 Distribution in Various Organs

At the time of sacrifice, the animals were anaesthetized by intraperitoneal injection of 2.5 mL/kg body weight of a mixture ketamine hydrochloride (50 mg/mL) and xylazine hydrochloride (20 mg/mL) in PBS. Rats were then rapidly sacrificed by exsanguination via intracardiac puncture. The organs of interest were harvested followed by the cutting in pieces for organs weighting more that 2 g such as liver, stomach, small intestine and colon. Each piece was thereafter rinsed with physiological serum prior to be wiped with soft paper tissue, weighed and counted separately. The selected organs were liver, kidneys, heart, lungs, spleen, skeletal muscle, femur, brain, thyroid, stomach, small intestine with content, colon with content, skin and perirenal fat.

The counting of tissue radioactivity was performed in an automatic gamma counter (Wallace Wizard 2470—Perkin Elmer) calibrated for Iodine-125 radionuclide (efficiency: 74%—counting time: 10 sec).

The concentration of radioactivity in the organs/tissues is expressed as percentage of the injected dose per gram of tissue (% ID/g). Data analysis includes the percentage of the injected dose (% ID) and equivalent quantity of protein per organ or tissue. For well-defined organs, these were calculated using the radioactivity counted in whole organ. For blood, this was approached assuming that blood accounts for 6.4% of total body weight.

In addition, the ratio between the radioactivity retained in the tissues and the radioactivity in blood was calculated (ratio organ/blood). Finally, the ratio between the organ/blood ratio of sALPI-PLAP and the organ/blood ratio of LVL-RecAP was calculated (FIG. 2).

B.6 Distribution in Rat Blood and Serum

Blood and Serum Radioactive Level

At the time of sacrifice, the blood samples were obtained from exsanguinations via intracardiac puncture on anaesthetized rat by intraperitoneal injection of a mixture of ketamine hydrochloride and xylazine hydrochloride in PBS.

At the other time points indicated in the study design (table 8 and 9), the blood was withdrawn from the lateral tail vein (right) using a 23-gauge butterfly needle without anesthesia.

Each blood sample was collected into preweighed Microvette tubes with clotting activator (Sarstedt). The tubes were weighed and the radioactivity was measured in the Gamma counter.

Blood samples were incubated at room temperature for 30 min and then, they are centrifuged for 5 minutes at 10 000 g to prepare serum. Serum was collected into pre-weighed tubes and counted in the Gamma counter.

The concentration of radioactivity in blood and serum is expressed as percentage of the injected dose and equivalent quantity of sALPI-PLAP per mL.

Data analysis includes the percentage of the injected calculated for the total blood and serum.

Tables 10 and 11 show the ratio of radioactivity measured in different organs in relation to blood serum radioactivity of sALPI-PLAP and LVL-RecAP respectively. FIG. 2 shows the ratio of the organ/blood ratio LVL-RecAP to organ/blood ratio sALPI-PLAP. A ratio of 2, for instance, indicates that LVL-RecAP is targeted twice as much to the indicated organ as sALPI-PLAP. Higher ratios further indicate that relatively more activity of LVL-RecAP is found in a particular organ when the same dose is used.

TABLE 10

Organ/Blood ratio for sALPI-PLAP

| ORGANS | 0.5 H | 2 H | 6 H | 24 H | 48 H |
| --- | --- | --- | --- | --- | --- |
| Thyroid/Trachea | 0.1624 ± 0.0157 | 4.6771 ± 0.4433 | 31.745 ± 5.175 | 208.16 ± 23.74 | 733.85 ± 79.16 |
| Skin | 0.0307 ± 0.0035 | 0.2842 ± 0.0134 | 0.4661 ± 0.1617 | 0.9448 ± 0.2565 | 1.0787 ± 0.3686 |
| Kidneys | 0.2076 ± 0.0011 | 0.3438 ± 0.0310 | 0.3535 ± 0.0219 | 0.3250 ± 0.0467 | 0.4299 ± 0.0219 |
| Stomach | 0.0446 ± 0.0016 | 1.0699 ± 0.1665 | 3.0622 ± 0.6977 | 1.4478 ± 0.1200 | 3.5819 ± 0.9018 |
| Spleen | 0.5388 ± 0.0796 | 0.4133 ± 0.0322 | 0.2880 ± 0.0283 | 0.2256 ± 0.0270 | 0.2273 ± 0.0254 |
| Liver | 5.2403 ± 0.1943 | 1.9917 ± 0.0347 | 0.4811 ± 0.0877 | 0.3219 ± 0.0325 | 0.4676 ± 0.0295 |
| Heart | 0.1824 ± 0.0136 | 0.2259 ± 0.0198 | 0.2605 ± 0.0217 | 0.2791 ± 0.0387 | 0.2809 ± 0.0165 |
| Lungs | 0.1777 ± 0.0119 | 0.2767 ± 0.0318 | 0.3397 ± 0.0730 | 0.3833 ± 0.0091 | 0.3937 ± 0.0251 |
| Skeletal muscle | 0.0334 ± 0.0033 | 0.0978 ± 0.0193 | 0.0842 ± 0.0178 | 0.0876 ± 0.0038 | 0.0947 ± 0.0150 |
| Fat | 0.0095 ± 0.0023 | 0.0261 ± 0.0070 | 0.0509 ± 0.0111 | 0.0615 ± 0.0065 | 0.0874 ± 0.0153 |
| Brain | 0.0160 ± 0.0031 | 0.0257 ± 0.0011 | 0.0213 ± 0.0011 | 0.0253 ± 0.0025 | 0.0408 ± 0.0063 |
| Femur | 0.1886 ± 0.0217 | 0.1991 ± 0.0131 | 0.1901 ± 0.0155 | 0.1602 ± 0.0119 | 0.1612 ± 0.0132 |
| Small intestine | 0.1882 ± 0.0247 | 0.8440 ± 0.1896 | 1.1055 ± 0.0827 | 1.0729 ± 0.1268 | 0.6329 ± 0.1044 |
| Colon | 0.0227 ± 0.0028 | 0.0777 ± 0.0077 | 0.4150 ± 0.0489 | 0.3473 ± 0.0596 | 0.3991 ± 0.0964 |

TABLE 11

Organ/Blood ratio for LVL-RecAP

| ORGANS | 0.5 H | 2 H | 6 H | 24 H | 48 H |
| --- | --- | --- | --- | --- | --- |
| Thyroid/Trachea | 0.5934 ± 0.0892 | 7.3638 ± 1.5049 | 52.934 ± 13.475 | 462.83 ± 34.395 | 1075.2 ± 118.65 |
| Skin | 0.0942 ± 0.0012 | 0.4110 ± 0.0485 | 0.6843 ± 0.0810 | 1.2130 ± 0.1243 | 1.9213 ± 0.8965 |
| Kidneys | 0.5793 ± 0.0187 | 0.6425 ± 0.0555 | 0.6428 ± 0.0098 | 0.8238 ± 0.0826 | 1.2481 ± 0.1089 |
| Stomach | 0.2262 ± 0.1021 | 1.5983 ± 0.3099 | 6.2917 ± 3.5698 | 3.0042 ± 1.2012 | 0.9930 ± 0.3279 |
| Spleen | 2.2771 ± 0.1172 | 1.0977 ± 0.1190 | 0.5831 ± 0.0292 | 0.3673 ± 0.0796 | 0.3623 ± 0.0429 |
| Liver | 7.6513 ± 0.9295 | 3.8409 ± 0.0277 | 0.6131 ± 0.0900 | 0.5869 ± 0.0967 | 0.7940 ± 0.0133 |
| Heart | 0.2030 ± 0.0105 | 0.2762 ± 0.0096 | 0.2780 ± 0.0316 | 0.2630 ± 0.0138 | 0.3144 ± 0.0023 |
| Lungs | 0.3007 ± 0.0201 | 0.3740 ± 0.0446 | 0.4332 ± 0.0111 | 0.3966 ± 0.0235 | 0.4515 ± 0.0220 |
| Skeletal muscle | 0.0462 ± 0.0072 | 0.0997 ± 0.0142 | 0.1036 ± 0.0251 | 0.0784 ± 0.0113 | 0.0953 ± 0.0080 |
| Fat | 0.0298 ± 0.0078 | 0.0380 ± 0.0063 | 0.0495 ± 0.0034 | 0.0781 ± 0.0155 | 0.0970 ± 0.0245 |
| Brain | 0.0261 ± 0.0052 | 0.0389 ± 0.0085 | 0.0253 ± 0.0028 | 0.0288 ± 0.0016 | 0.0646 ± 0.0100 |
| Femur | 0.3764 ± 0.0102 | 0.2973 ± 0.0098 | 0.2460 ± 0.0149 | 0.1804 ± 0.0325 | 0.1746 ± 0.0370 |
| Small intestine | 0.1573 ± 0.0049 | 0.5625 ± 0.0393 | 1.0308 ± 0.1134 | 0.9402 ± 0.0935 | 0.6612 ± 0.1003 |
| Colon | 0.0361 ± 0.0047 | 0.1049 ± 0.0271 | 0.3658 ± 0.0693 | 0.5353 ± 0.1967 | 0.4787 ± 0.0712 |

Example 5

Akp2−/− Mouse Model of Infantile Hypophosphatasia

The Akp2−/− mice model of infantile hypophosphatasia is known in the art (J Dent Res 90(4):470-476, 2011). In short, Akp2−/− mice were created by insertion of the Neo cassette into exon 6 of the mouse TNALP gene (Akp2) via homologous recombination to functionally inactivate the Akp2 gene, resulting in no detectable TNALP mRNA or protein.

Animal use and tissue collection procedures followed approved protocols from the Sanford-Burnham Medical Research Institute Animal Ethics Committee. Animals were treated with either vehicle (N=10), 1 mg LVL-RecAP/kg/day (N=10); 8 mg LVL-RecAP/kg/day (N=8) or 16 mg LVL-RecAP/kg/day (N=10). Survival was measured and skeletal development assessed. Mineralization of kidneys was assessed. Plasma PPi, plasma pyridoxal, plasma calcium and phosphate levels were measured, femur and/or tibia length for the different treatment groups were measured. MicroCT data was colleted for analysis of residual hyperosteodosis at each dose.

Results

Enhanced long-term survival for animals treated at 16 mg/kg/day (FIG. 3).

There was (incomplete) rescue of the skeletal defect in the long bones even at the highest dose (data not shown)

There was some rescue in the dental phenotype (data not shown).

There seems to be rescue of craniosynostosis (data not shown; to be confirmed)

The work on the kidneys is still ongoing. There was indication of mineral in kidneys of untreated mice and less mineral in kidneys of treated mice (data not shown).

Example 6

Ischemia Reperfusion in a Pig Kidney Model

Materials and Methods

Vehicle, Control and Test Article Information

Control and Test Article Preparation

Fresh control article, LVL-RecAP Diluent Solution (placebo), was prepared for use on study prior to each dose administration and was stored refrigerated at 2 to 8° C. when not in use.

The test article, LVL-RecAP, was used as received. No adjustment was made for purity when preparing the test article formulations. Formulations of the test article were prepared by mixing with the appropriate volume of sterile saline to achieve nominal concentrations of 0, 0.96, or 4.8 mg/mL. Formulations were prepared prior to each dose administration under a laminar flow hood using sterile equipment and aseptic techniques. The formulations were dispensed into the appropriate number of amber glass serum bottles, kept on ice prior to use and were used for dosing within 2 hours of preparation. On occasion, additional preparations were made as necessary during the course of the study.

Analysis of Dosing Formulations

Duplicate 0.5 mL samples of the final dosing formulation were collected on prior to dosing each day of preparation on Day 0 (Groups 3 to 7) and Day 7 (Group 7). Samples were collected from the middle strata and were stored frozen (−50 to −90° C.) for possible future analysis.

Test System Information

Animal Acquisition and Acclimation

Male experimentally naïve Domestic Yorkshire crossbred swine (farm pigs) (approximately 8 to 10 weeks of age, at receipt) were received from Midwest Research Swine, Gibbon, Minn. During the 10 to 28 day acclimation period, the animals were observed daily with respect to general health and any signs of disease. Ova and parasite evaluations on stool samples were performed, and all results were negative for animals placed on study.

Randomization, Assignment to Study, and Maintenance

Using separate simple randomization procedures animals (weighing 12.5 to 25.0 kg at randomization) were assigned to the control and treatment groups identified in the following Table 12.

TABLE 12

Group Assignments

| Group Number | Dose Level | Number of Male Animals[a] | |
|---|---|---|---|
| | | Initial | Evaluated |
| 1 | Control | 7 | 6 |
| 2 | Sham[b] | 7 | 6 |
| 5 | 0.32 mg/kg | 7 | 6 |
| 6 | 1.6 mg/kg | 7 | 7 |
| 7 | 0.32 mg/kg/day[c] | 7 | 7 |

[a]On Day 0, animals underwent a surgical procedure during which the left or right kidney was removed and the contralateral renal artery was occluded for 45 minutes. Following occlusion, the vessel was allowed to reperfuse. Seven animals were submitted for surgery in each group with the intent to achieve six animals on study.
[b]Sham animals underwent the surgical procedure during which the left kidney was removed. However, renal occlusion and reperfusion were not conducted.
[c]On Day 0, half of the dose was administered prior to reperfusion and the remaining half of the dose was administered at 8 ± 2 hours post-reperfusion. A full dose was administered daily for the remainder of the in-life period.

Animals selected for study were as uniform in age and weight as possible. A veterinarian assessed the health of the animals prior to placement on study. Extra animals obtained for the study, but not placed on study, were transferred to the stock colony.

Each animal was assigned an animal number used in the Provantis™ data collection system and was implanted with a microchip bearing a unique identification number. Each animal was also identified by a vendor ear tag. The individual animal number, implant number, ear tag number, and study number comprised a unique identification for each animal. Each cage was identified by the animal number, study number, group number, and sex.

The animals were individually housed in runs with raised flooring or stainless steel mobile cages with plastic coated flooring. This type of housing provided adequate room for exercise for these animals. Animal enrichment was provided according to MPI Research SOP. Fluorescent lighting was provided for approximately 12 hours per day. The dark cycle was interrupted intermittently due to study related activities. Temperature and humidity were continuously monitored, recorded, and maintained to the maximum extent possible within the protocol designated ranges of 61 to 81° F. and 30 to 70%, respectively. The actual temperature and humidity findings are not reported, but are maintained in the study file.

Diet (Certified Lab Diet® #5K99, PMI Nutrition International, Inc.) was offered via limited feedings, except during designated periods. Food enrichment, including fiber bits or tablets, was offered as needed.

Surgical Procedures

Procedure-Related Medications

The following Table 13 presents the procedure-related medications and dose levels used during the course of the study.

TABLE 13

Procedure-related Medications and Dose Levels

| Medication | Surgery (Day 0) | Daily Postsurgery |
|---|---|---|
| Acepromazine maleate | 0.1 mg/kg IM | — |
| Atropine sulfate | 0.05 mg/kg IM | — |
| Telazol | 5 to 8 mg/kg IM | — |
| Isoflurane | To effect by inhalation | — |
| Buprenorphine | 0.02 mg/kg IM TID | 0.02 mg/kg IM TID × 3 days |
| Ketoprofen | 3 mg/kg IM | 3 mg/kg IM SID × 3 days |
| Cefazolin | 25 mg/kg IV | — |
| Ceftiofur | 2.2 mg/kg IM | 2.2 mg/kg IM SID × 3 days |
| Lactated Ringer's solution (LRS) | 10 to 15 mL/kg/hr IV | — |
| Marcaine | 2 mg/kg INF | — |
| 0.9% NaCl | As needed for irrigation | — |

IV—Intravenous
IM—Intramuscular
INF—Infused into incision
SID—Once daily
TID—Twice Daily (every 6 to 9 hours)

Pre- and post-operative procedures were conducted in accordance with MPI Research SOP. The animals were fasted for at least 8 hours prior to surgery and anesthesia was induced and maintained as indicated in Table 13. Body temperature was maintained at 37±3° C. Prior to surgery, ultrasounds were performed to determine if renal cysts were present. If no cysts were observed, the left kidney was removed and the right kidney was treated as described below. If cysts were present on one kidney, that kidney was removed and the contralateral kidney underwent the occlusion procedure. If cysts were present in both kidneys, the animal was removed from study without undergoing the surgical procedure.

Surgical Procedure

Renal ischemia/reperfusion injury was induced using the procedure published by Lee et al (J. Vet. Med. Sci 72(1): 127-130). Once anesthetized, all animals were placed in dorsal recumbency and the surgical sites were prepared with alternating wipes of chlorhexidine scrub and solution. A midline laparotomy was performed to expose both kidneys. Based on the ultrasound findings, the left or right kidney was removed.

For Group 2 animals (Sham), the inserted lap sponges were then removed and accounted for and the abdomen was lavaged with warm sodium chloride. The abdomen was closed in a routine manner and the skin was closed with skin staples and tissue glue. The animals were then allowed to recover.

For all other animals, after removal of the designated kidney, the remaining renal vessels were isolated and retracted using vessel loops. The vessel loops were used to occlude the vessels for 45 (±1) minutes, after which the vessels were allowed to reperfuse. An intravenous bolus dose of the control or test article was administered at a dose volume of 0.333 mL/kg (a half dose of 0.167 mL/kg was administered to Group 7 animals) just prior to reperfusion. For all Group 1, 5 and 6 animals (control, 0.32, and 1.6 mg/kg), the implanted lap sponges were then removed and accounted for, the abdomen was lavaged and closed as described above, and the animals were allowed to recover.

For all Group 7 animals (0.32 mg/kg/day), an incision was made in the groin and the left or right femoral vein was isolated. A catheter was advanced into the vessel and the catheter was tunneled under the skin and exteriorized through an incision made on the thorax. A port was attached and anchored to the muscle with non-absorbable suture. The implanted lap sponges were then removed and accounted for, the abdomen was lavaged and closed as described above, and the animals were allowed to recover.

Test or Control Article Administration

On Day 0, the control or test article was intravenously administered to all Group 1, 5, and 6 animals just prior to reperfusion at a full dose of 0, 0.32, and 1.6 mg/kg, respectively. All doses were administered at a dose volume of 0.333 mL/kg. Also on Day 0, the test article was intravenously administered to all Group 7 animals at a combined dose level of 0.32 mg/kg in two separate half doses of 0.16 mg/kg at a dose volume of 0.167 mL/kg. The first dose was administered just prior to reperfusion and the second dose was administered at approximately 8 (±2) hours post-reperfusion. Full doses of 0.32 mg/kg/day (0.333 mL/kg) were administered to all Group 7 animals on Days 1 to 7 at approximately the same time of the day as the initial Day 0 dose (±2 hours).

Statistics

Table 14 below defines the set of comparisons used in the statistical analyses described in this section.

TABLE 14

Table of Statistical Comparisons

| Reference Group | Comparison Groups |
|---|---|
| 1 | 2, 5, 6, 7 |
| 2 | 5, 6, 7 |
| 5 | 7 |

The raw data were tabulated within each time interval, and the mean and standard deviation were calculated for each endpoint and group. For serum creatinine concentrations, treatment groups were compared to the reference groups using Repeated Measures Analysis of Covariance (RMANCOVA).

Repeated Measures Analysis of Covariance (RMANCOVA) For endpoints measured at three or more post-test time intervals, a repeated measures analysis (mixed model) was conducted. For each endpoint, the model tested for the effects of treatment, time, and the interaction of treatment and time. Pre-test data (last measurement before dosing) were included in the model as a covariate.

If there was no significant ($p>0.05$) treatment by time interaction, the treatment main effect was evaluated. If the treatment effect was not significant ($p>0.05$), the results were deemed not significant and no further analyses was conducted on the variable. If the treatment effect was significant ($p<0.05$), linear contrasts were constructed for pairwise comparison of each treatment group with the reference group. If the interaction was significant ($p<0.05$), each treatment group was compared to the appropriate reference group through the simple effect of 'treatment' for each time point. These simple effect pairwise comparisons were obtained from the 'treatment by time' interaction.

Results of all pair-wise comparisons are reported at the 0.05 and 0.01 significance levels. All tests were two-tailed tests.

Results

Serum Creatinine

As shown in FIG. 4, there were mild to moderate elevations creatinine at all intervals, relative to pre-test values. Creatinine tended to maximally increase at 24 hours post-reperfusion, and then gradually decrease over subsequent intervals. Changes in creatinine were consistent with reduced glomerular filtration secondary to procedure-related renal injury (data not shown). In most treatment groups, and at most intervals, administration of the test article tended to attenuate procedure-related elevations in creatinine, showing protective effect of LVL-RecAP.

As illustrated in FIG. 5 there were dose-dependent elevations in alkaline phosphatase (ALP) activity in all treatment groups receiving the test article at 24 hours post-reperfusion, relative to pretest values. ALP activity gradually decreased in treatment groups receiving ≤1.6 mg/kg, but continued to progressively increase in animals receiving 0.32 mg/kg/day.

Example 7

Safety Testing in Human

Material and Methods

Objectives:

To evaluate the safety and tolerability of single and multiple doses of recombinant improved alkaline phosphatase (LVL-recAP) administered by intravenous (i.v.) infusion in healthy subjects.

To determine the pharmacokinetics (PK) of LVL-recAP after i.v. infusion of single and multiple doses of LVL-recAP in healthy subjects.

Design and Treatments

This is a 2-part, single-center study in a planned number of 50 healthy subjects. Part A will be a randomized, double-blinded, placebo-controlled, single ascending dose (SAD) study in up to 4 sequential groups of 8 healthy male and female subjects each (6 on LVL-recAP and 2 on placebo). An attempt will be made to include in each treatment group an equal number of male and female subjects, with a minimal of 2 and a maximum of 4 females per group. A single dose of LVL-recAP or placebo will be administered by a 1-hour i.v. infusion. Part B will be a randomized, double-blinded, placebo controlled, multiple ascending dose (MAD) study in up to 2 groups of 9 healthy male and female subjects each (6 on LVL-recAP and 3 on placebo). An attempt will be made to include in each treatment group an equal number of male and female subjects, with a minimal of 2 and a maximum of 4 females per group. Subjects will receive a 1-hour i.v. infusion of LVL-recAP or placebo on Days 1, 3 and 5. The following treatments will be administered:

Part A

Group 1: 1-hour infusion of 200 U/kg LVL-recAP
Group 2: 1-hour infusion of 500 U/kg LVL-recAP
Group 3: 1-hour infusion of 1000 U/kg LVL-recAP
Group 4: 1-hour infusion of 2000 U/kg LVL-recAP Part B Group 5: 1-hour infusions of 500 U/kg LVL-recAP on Days 1, 2 and 3
Group 6: 1-hour infusions of 1000 U/kg LVL-recAP on Days 1, 2 and 3

After completion of Day 9 of Group 1 and Day 4 of Group 2 of Part A, an interim PK evaluation will be performed. Depending of the results, infusion and PK sampling schedules may be adjusted for the remaining SAD and MAD groups.

In this first-in-human study, the subjects participating in the lowest dose level in Part A (Group 1) will be dosed according to a sentinel dosing design to ensure minimal risk. This means that initially 2 subjects will be dosed. One of these subjects will receive the active medication LVL-recAP and the other subject will receive placebo. If the safety and tolerability results of the first 24 hours following dosing for the initial subjects are acceptable to the Principal Investigator, the other 6 subjects of the lowest dose level will be dosed in a placebo controlled randomized manner (5 active and 1 placebo).

Observation Period

Part A: from Day −1 until 48 hours (Day 3) after drug administration. Short ambulant visits to the clinical research centre on Days 4, 6, 9 and 15

Part B: from Day −1 until 48 hours (Day 7) after last drug administration. Short ambulant visits to the clinical research centre on Days 8, 10, 13 and 19 Subjects will be screened for eligibility within 3 weeks prior to the (first) drug administration of each group of the study.

Follow-up examinations will take place on Day 15 (Part A) and Day 19 (Part B).

Subjects

Part A: 32 healthy male and female subjects
Part B: 18 healthy male and female subjects
Main Criteria for Inclusion
Gender: male or female
Age: 18-55 years, inclusive
Body Mass Index (BMI): 18.0-30.0 kg/m2, inclusive
Study Drug
Active Drug
Active substance: LVL-recAP, an improved recombinant form of endogenous human alkaline phosphatase (AP)
Activity: a hydrolase enzyme responsible for dephosphorylation of monoesters of phosphoric acid
Indication: Acute kidney injury
Strength: 600, 1500, 3000 and 6000 U/mL
Dosage form: i.v. infusion
Manufacturer: pharmacy of PRA
Placebo
Substance: 20 mM citrate, 250 mM sorbitol, 2 mM $MgCl_2$, 50 µM $ZnCl2$, pH 7.0
Activity: none
Indication: not applicable
Strength: not applicable
Dosage form: i.v. infusion
Manufacturer: Nova Laboratories Ltd, Gloucester Crescent, Wigston, Leicester, LE18 4YL, UK
Criteria for Evaluation
Safety: adverse events (AEs), vital signs (including supine systolic and diastolic blood pressure, pulse, body temperature, respiratory rate), 12-lead electrocardiogram (ECG), continuous cardiac monitoring (telemetry), clinical laboratory (including clinical chemistry [AP is considered a PK parameter], hematology and urinalysis) tests, physical examination and anti-drug antibodies (ADA)
Pharmacokinetics: PK parameters based on analysis of serum concentrations of LVL-recAP and AP activity.

Results

The dosing and observation time periods for all dosing groups have been concluded and no serious adverse events were observed in any of the groups.

The analyses of all parameters measured is ongoing.

Example 8

Materials and Methods

Mice

The generation and characterization of the Alpl$^{-/-}$ mice has been reported previously (Narisawa et al., 1997). Alpl$^{-/-}$ mice phenocopy infantile HPP, including global deficiency of TNAP, PP$_i$ accumulation and mineralization defects (Fedde et al., 1999; Narisawa et al., 2001; Anderson et al., 2004; Millan et al., 2008). Dietary supplementation with vitamin B6 briefly suppresses seizures and extends lifespan until postnatal days 18-22 but hypomineralization and accumulation of osteoid continue to worsen with age (Narisawa et al., 1997; Fedde et al., 1999; Narisawa et al., 2001; Millán et al., 2008). Therefore, all animals (breeders, nursing mothers, pups, and weanlings) in this study were given free access to modified laboratory rodent diet 5001 containing increased levels (325 ppm) of pyridoxine. Genotyping was performed by PCR on genomic DNA as previously described (Yadav et al., 2011). The Institutional Animal Care and Use Committee (IACUC) approved all animal studies.

Soluble Chimeric Human Alkaline Phosphatase (LVL-RecAP)

A solution of LVL-RecAP at 10.1 mg/ml in 25% glycerol w/v, 5 mM Tris/HCl 2 mM MgCl$_2$, 50 μM ZnCl$_2$, and at pH 8.0 was used. The enzyme had a purity of >99.99% as determined by high-pressure liquid chromatography.

Dose-Response Study with LVL-RecAP

Alpl$^{-/-}$ mice were divided into 5 cohorts: Vehicle-treated: Alpl$^{-/-}$ mice treated with vehicle (n=14) only; LVL-RecAP1: Alpl$^{-/-}$ mice treated with LVL-RecAP at 1 mg/kg/day (n=14); LVL-RecAP8: Alpl$^{-/-}$ mice treated with LVL-RecAP at 8 mg/kg/day (n=12); and LVL-RecAP16: Alpl$^{-/-}$ mice treated with LVL-RecAP at 16 mg/kg/day (n=10). Wild-type littermates of Alpl$^{-/-}$ mice served as reference animals and did not receive injections (n=14). The vehicle or LVL-RecAP cohorts were injected daily SC into the scapular region. Injections were administered between 8:00 and 11:00 AM. Volumes administered were calculated based on body weight measured prior to injection. All treatments began on postnatal day 1, and were repeated daily for up to 53 days or until the time of necropsy.

Sample Collection

Necropsy was performed on postnatal day 53 (p53), 24 h after the final injection of LVL-RecAP for those animals that completed the experimental protocol, or sooner for those animals that appeared terminally ill. Avertin was administered intraperitoneally prior to euthanasia. Blood was collected into lithium heparin tubes by cardiac puncture. Necropsy consisted of a gross pathology examination and x-rays.

Radiography and Microcomputed Tomography (μCT)

Radiographic images of skeletons were obtained with a Faxitron MX-20 DC4 (Chicago, Ill., USA), using an energy of 20 kV. Hemi-mandibles were scanned at 30 kV. Whole dissected skulls from P21 mice were fixed, then scanned at an 18 μm isotropic voxel resolution using the eXplore Locus SP μCT imaging system (GE Healthcare Pre-Clinical Imaging, London, ON, Canada). Measurements were taken at an operating voltage of 80 kV and 80 mA of current, with an exposure time of 1600 ms using the Parker method scan technique, which rotates the sample 180 degrees plus a fan angle of 20 degrees. Scans were calibrated to a hydroxyapatite phantom and 3D images were reconstructed at an effective voxel size of 18 μm$^3$. A fixed threshold of 1400 Hounsfield Units was used to discriminate mineralized tissue. Regions of interest (ROI's) for parietal and frontal bones were established as 1 mm in length, 1 mm in width, depth equivalent to thickness of bone and position starting at a 0.75 mm distance from sagittal and coronal sutures, as previously described (Liu et al., 2014). Parameters of bone volume, density and structure were measured using Microview version 2.2 software (GE Healthcare Pre-Clinical Imaging, London, ON) and established algorithms (Meganck et al., 2009; Umoh et al., 2009). Student's t-tests comparing quantitative results were performed to establish statistically significant differences between genotypes. μCT bone data were analyzed and are reported in accordance with the recommendations of Bouxsein et al. 2010 (Bouxsein et al., 2010). For dental imaging, dissected hemi-mandibles were scanned on a Scanco Medical μCT 50 (Scanco Medical AG, Bruttisellen, Switzerland) at 10 μm voxel size. Mandible z-stacks were exported as DICOM files and reoriented using ImageJ software (1.48r), with comparable coronal, sagittal, and transverse planes of section chosen for comparison. For quantitative analysis, mandibles were scanned on a Scanco Medical μCT 35 at 6 μm voxel size, 55 KVp, 145 mA, with 0.36 degrees rotation step (180 degrees angular range) and a 400 ms exposure per view. Scanco μCT software (HP, DECwindows Motif 1.6) was used for 3D reconstruction and image viewing. After 3D reconstruction, crown, enamel, roots, and alveolar bone volumes were segmented using global threshold 0.6 g/cc. Total volume (TV), bone (mineralized tissue) volume (BV), and tissue mineral density (TMD) were measured for the whole crown and separately for enamel, root dentin, and alveolar bone in the furcation region. For enamel and root, thickness was also measured.

Histological Analyses

Bone samples were cleaned, fixed in 4% paraformaldehyde/phosphate buffered saline for 3 days at 4° C., and then transferred to 70% ethanol for storage at 4° C. Plastic sections were prepared as described previously (Yadav et al., 2012). Von Kossa and Van Gieson trichrome staining was performed on plastic sections as described previously (Narisawa et al., 1997). Von Kossa or Van Gieson-stained sections were scanned by ScanScopeXT system (Aperio, Vista, Calif., USA), and images were analyzed by using the Bioquant Osteo software (Bioquant Osteoanalysis Co., Nashville, Tenn., USA). Left hemi-mandibles used for histology were fixed in Bouin's solution for 24 h, and then demineralized in AFS solution (acetic acid, formaldehyde, sodium chloride), and embedded in paraffin for serial sectioning, as described previously (Foster, 2012). For picrosirius red staining, deparaffinized tissue sections were stained with 0.2% aqueous solution of phosphomolybdic acid hydrate, 0.4% Direct red 80, and 1.3% 2,4,6-trinitrophenol (Polysciences, Inc., Warrington, Pa.), as described previously (Foster, 2012). Picrosirius red-stained sections were observed under polarized light for photomicrography.

Biomechanical Testing

After removal of muscle tissue, lengths of the femur, tibia, humerus and radius were measured with a caliper. Bones were frozen, wrapped in gauze containing a saline solution to avoid dehydration. Isolated femurs and tibias were assessed with three-point bending test by using the Instron 1101 universal material testing machine as described previously (Huesa et al., 2011). Bones were slowly thawed and held at room temperature prior to testing. The intact femurs and tibias were placed in the testing machine on two supports separated by a distance of 15 mm and load was applied to the middle of the diaphysis, thus creating a three-point bending test at a speed of 2 mm min$^{-1}$.

PP$_i$ Assay

PP$_i$ concentrations in plasma were determined by differential adsorption on activated charcoal of UDP-D-[6-3H]glucose (Amersham Pharmacia) from the reaction product 6-phospho [6-3H]gluconate, as described (Hessle et al., 2002; Yadav et al., 2014).

Statistics

Considering that the different concentrations of LVL-RecAP resulted in different survival rates, it was not possible to compare the three treatment cohorts in an age-matched fashion. For this reason, Student t unpaired, parametric, two-tailed test was performed to compare the treated Alpl$^{-/-}$ mice to the WT cohort. Differences were considered significant when p<0.05. In order to compare the differences in the survival curves among the treatment cohorts, the Gehan-Breslow-Wilcoxon test was performed.

Results

Increased Survival and Body Weight in LVL-RecAP-Treated Alpl$^{-/-}$ Mice

Survival in mice receiving 8 mg/kg/day (LVL-RecAP8) or 16 mg/kg/day (LVL-RecAP16) of LVL-RecAP was significantly improved compared to the vehicle-treated and the 1 mg/kg/day (LVL-RecAP1) cohort (p=0.001) (FIG. 6A). Differences were statistically significant when the survival curves of the treated cohorts were compared against each other (p<0.0001 for all comparisons). Median survival was 44, 22 and 19 days in the LVL-RecAP8, LVL-RecAP1 and vehicle-treated cohorts, respectively. No median survival could be calculated for the LVL-RecAP16 cohort as the animals lived until the termination of the experiment at day 53.

Alpl$^{-/-}$ animals weigh less than their WT littermates, starting around p7. Treatment with 1 mg/kg/day LVL-RecAP led to a statistically significant increase in body weight compared to vehicle-treated mice, and a non-significant difference compared to WT littermates at 18 days of treatment (FIG. 6B). Alpl$^{-/-}$ mice usually die by p18-24 on Vitamin B6 diet, therefore comparison of longer-lived LVL-RecAP8 and LVL-RecAP16 cohorts to vehicle-treated mice was not possible, and these were instead compared to WT mice. Animals in the LVL-RecAP8 cohort weighed significantly less than their WT littermates from p18 (FIG. 6C) while mice in the LVL-RecAP16 cohort showed normalization in body weight, and were undistinguishable from WT mice at p53 (FIG. 6D).

LVL-RecAP Treatment Improves the Skeletal Phenotype of Alpl$^{-/-}$ Mice

Radiographs of untreated Alpl$^{-/-}$ mice (FIG. 7A) demonstrated profound skeletal abnormalities including reduced tissue mineral density and fractured bones, as previously described (Yadav et al., 2011). We found improvement in the skeletal pathology in Alpl$^{-/-}$ mice receiving 1 mg/kg/day LVL-RecAP for 18 days (FIG. 7A), and the benefit was more profound in the LVL-RecAP8 and LVL-RecAP16 cohorts (FIG. 7B). The distal extremities displayed a normalized morphology, regardless of dose, while partial correction was observed in the spine, forelimbs, hindlimbs, and ribcage for all treatment cohorts. LVL-RecAP8 and LVL-RecAP16 mice also presented minor cracks or fractures in femora and tibiae. The articular contour in knees and elbows presented irregularities in LVL-RecAP8 and LVL-RecAP16 at p44 and p53, respectively (FIG. 7B).

To assess the degree of improvement of osteomalacia, we performed a histomorphometric analysis of plastic-embedded undecalcified sections of hindlimbs of LVL-RecAP-treated and WT control mice (FIGS. 8A and 9A). We measured bone and osteoid volumes (FIGS. 8B, 8C) and also analyzed serum PP$_i$ levels (FIGS. 9B, 9C). Consistent with earlier findings (Yadav et al., 2011), von Kossa staining revealed that Alpl$^{-/-}$ mice show severe defects in mineralization, thin cortical bone, reduced trabecular bone and impaired ossification centers (FIG. 8A), whereas both LVL-RecAP8 and LVL-RecAP16-treated animals showed significantly enhanced cortical bone and improved secondary ossification centers. Histomorphometry (FIGS. 8B, 8C) revealed that the BV/TV ratio (FIG. 8B), both in the LVL-RecAP8 and LVL-RecAP16 cohorts, was still significantly lower than in the age-matched WT controls (0.0321 and 0.0302, N=9), whereas the OV/BV percentage (FIG. 8C) was significantly higher for both of the treatment cohorts compared to WT controls (0.0001 and 0.0175, N=9). Differences between LVL-RecAP8 and LVL-RecAP16 treatment cohorts were not statistically significant. Histological trichrome staining (FIG. 9A) on plastic sections of hindlimbs confirmed these findings. Alpl$^{-/-}$ mice have severely reduced mineralized bone mass (green-stained regions), with deficiencies in cortical and trabecular bone marked by osteoid accumulation (red-stained regions). In contrast, 53-day-old WT controls have robust cortical bones, trabecular bone present in the secondary ossifications and little osteoid at bone surfaces. Alpl$^{-/-}$ mice in the LVL-RecAP8 and LVL-RecAP16 cohorts display a significant improvement in cortical bone, especially in the LVL-RecAP16 cohort, where no major differences were noted compared to WT mice. While trabecular bone formation in the secondary ossification centers in Alpl$^{-/-}$ mice is improved by treatment, LVL-RecAP8 and LVL-RecAP16 mice still retained larger than normal regions of osteoid (red). In agreement with the skeletal findings, we found correction of the serum PP$_i$ concentrations in all treatment cohorts. LVL-RecAP1 animals (FIG. 9B) harbor significantly reduced PP$_i$ levels when compared to the vehicle-treated control animals. LVL-RecAP16 treated animals have PP$_i$ levels that are statistically undistinguishable from that of WT littermates.

Absence of Craniofacial Abnormalities in LVL-RecAP-Treated Alpl$^{-/-}$ Mice

Alpl$^{-/-}$ mice feature craniofacial shape abnormalities and coronal suture fusion (Liu et al., 2014). To determine the extent to which the craniofacial skeleton is affected by treatment in Alpl$^{-/-}$ mice, we performed µCT-based analyses of frontal and parietal cranial bones. Results at p21 show that both frontal and parietal bones of vehicle treated Alpl$^{-/-}$ mice were significantly reduced in bone volume fraction, bone mineral content, bone mineral density, tissue mineral content and tissue mineral density when compared to WT or to treated Alpl$^{-/-}$ mice (Table 15). In contrast, neither frontal nor parietal bones of treated Alpl$^{-/-}$ mice were significantly different from those of wild type mice. Adult skulls of LVL-RecAP16-treated Alpl$^{-/-}$ mice did not appear different from WT in terms of size and shape (FIG. 10A-10F).

TABLE 15

μCT analyses of cranial bones. Frontal and parietal bones were analzyed in WT, untreated Alpl$^{-/-}$ (vehicle), and RecAP16-treated Alpl$^{-/-}$ mice at p21. Values are reported as means ± SD.

|  | Bone Volume Fraction | Bone Mineral Content (mg) | Bone Mineral Density (mg/cc) | Tissue Mineral Content (mg) | Tissue Mineral Density (mg/cc) |
|---|---|---|---|---|---|
| FRONTAL |  |  |  |  |  |
| Alpl$^{-/-}$ | 0.41 ± 0.06 * | 0.008 ± 0.001 * | 464 ± 27 * | 0.004 ± 0.001 * | 595 ± 28 * |
| LVL-RecAP16 | 0.72 ± 0.15 | 0.018 ± 0.005 | 615 ± 84 | 0.015 ± 0.006 | 697 ± 57 |
| WT | 0.70 ± 0.12 | 0.019 ± 0.008 | 615 ± 79 | 0.016 ± 0.008 | 709 ± 56 |
| PARIETAL |  |  |  |  |  |
| Alpl$^{-/-}$ | 0.52 ± 0.05 * | 0.018 ± 0.001 * | 494 ± 21 * | 0.005 ± 0.001 * | 597 ± 12 * |
| LVL-RecAP16 | 0.72 ± 0.08 | 0.018 ± 0.007 | 608 ± 74 | 0.015 ± 0.006 | 691 ± 61 |
| WT | 0.76 ± 0.10 | 0.020 ± 0.007 | 645 ± 73 | 0.017 ± 0.007 | 726 ± 51 |

* Indicates statistical significance between genotypes and between treatment cohorts.

LVL-RecAP Treatment Partially Rescues Alpl$^{-/-}$ Dentoalveolar Defects

Ablation of Alpl in mice results in developmental mineralization defects in cementum, dentin, alveolar bone, and enamel (Foster et al., 2014a; Foster et al., 2014b; McKee et al. 2011; Yadav et al., 2012), consistent with case reports on human subjects with HPP. Absence of acellular cementum results in loss of periodontal attachment to the tooth root surface and premature tooth exfoliation, a hallmark of HPP. LVL-RecAP8-treated and vehicle-treated Alpl$^{-/-}$ mice were compared to WT at p25-26, when molar tooth formation is near completion. Radiography and μCT imaging revealed that, compared to controls (FIGS. 11A, 11D), untreated Alpl$^{-/-}$ mouse mandibles featured grossly hypomineralized bone, short molars with thin dentin and wide pulp chambers, and severely defective incisors (FIG. 11B, 11F). By histology, Alpl$^{-/-}$ mouse teeth featured no acellular cementum, and alveolar bone osteoid invaded the periodontal ligament (PDL) space, leading to ankylosis and loss of a functional periodontium (FIG. 11G vs. 11E). Administration of 8 mg/kg/day LVL-RecAP improved radiographic appearance of molar height, dentin thickness, and bone mineralization at p26, though the incisor remained defective (FIG. 11C, 11H). Histologically, though this dose of LVL-RecAP did not restore acellular cementum to the root surface, the molar-associated PDL space and alveolar bone borders were better maintained (FIG. 11I).

The LVL-RecAP16 cohort was compared with WT at p50-53 to determine effects on mature tooth structure and function. Radiography and μCT imaging indicated reduced alveolar and interproximal bone mineralization around molar teeth in Alpl$^{-/-}$ mouse mandibles, compared to controls (FIG. 11J-11M). Molar tooth form and dentin appeared largely normalized in LVL-RecAP16 mice, and this was confirmed by μCT analysis of the first molar (Table 16). Enamel in the LVL-RecAP16 group was not different from WT in BV/TV or TMD. Molar crowns and roots showed mild but significant decreases of 4-10% in BV/TV and TMD compared to WT, indicating dentin mineralization as not fully rescued, and root thickness was decreased by 15%. Alveolar bone mineralization remained more severely defective in the LVL-RecAP16 group, with BV/TV decreased by 27% and TMD decreased by 13%, compared to WT. Incisor teeth in treated Alpl$^{-/-}$ mice also remained severely affected (FIG. 11K, 11M).

By histology, LVL-RecAP16 mice featured a mix of mineralized alveolar bone and osteoid, and a reduced but maintained PDL space (FIG. 11N, 11P). No tooth loss was noted in the LVL-RecAP16 group by p53, though periodontal attachment remained deficient, as evidenced by lack of cementum, PDL disorganization and detachment from the root surface, and down growth of the junctional epithelium. However, small regions of PDL attachment to the tooth were noted in association with organized PDL fibers (FIG. 11O, 11Q), indicating the presence of some compromised attachment that may function to retain molars.

TABLE 16

μCT analyses of dentoalveolar tissues. First mandibular molars and associated alveolar bone were compared at p50-53 in WT (n = 5) and Alpl$^{-/-}$ mice treated with RecAP16 (n = 4). Values are reported as means ± SD.

|  | TV (mm$^3$) | BV (mm$^3$) | BV/TV (%) | TMD (g HA/cm$^3$) | Thickness (μm) |
|---|---|---|---|---|---|
| Enamel |  |  |  |  |  |
| WT | 0.25 ± 0.03 | 0.24 ± 0.02 | 98.77 ± 0.52 | 1.69 ± 0.05 | 70.2 ± 0.5 |
| LVL-RecAP16 | 0.20 ± 0.02 * | 0.20 ± 0.02 * | 98.97 ± 0.27 | 1.68 ± 0.03 | 63.0 ± 0.5 |
| Crown |  |  |  |  |  |
| WT | 0.61 ± 0.04 | 0.56 ± 0.03 | 91.06 ± 0.64 | ND | ND |
| LVL-RecAP16 | 0.53 ± 0.03 * | 0.46 ± 0.03 * | 86.92 ± 0.69 * | ND | ND |
| Root |  |  |  |  |  |
| WT | 0.65 ± 0.05 | 0.56 ± 0.05 | 85.84 ± 0.74 | 1.07 ± 0.01 | 140.4 ± 8.4 |
| LVP-RecAP16 | 0.56 ± 0.06 | 0.44 ± 0.04 * | 77.27 ± 2.37 * | 1.02 ± 0.01 * | 121.5 ± 1.7 * |

TABLE 16-continued

μCT analyses of dentoalveolar tissues. First mandibular molars and
associated alveolar bone were compared at p50-53 in WT (n = 5) and
Alpl$^{-/-}$ mice treated with RecAP16 (n = 4). Values are reported as means ± SD.

| | TV (mm³) | BV (mm³) | BV/TV (%) | TMD (g HA/cm³) | Thickness (μm) |
|---|---|---|---|---|---|
| Alveolar Bone | | | | | |
| WT | 0.44 ± 0.04 | 0.29 ± 0.05 | 65.72 ± 5.08 | 1.01 ± 0.02 | ND |
| LVL-RecAP16 | 0.32 ± 0.05 * | 0.15 ± 0.02 * | 47.91 ± 4.25 * | 0.88 ± 0.02 * | ND |

* p < 0.05 by independent samples t-test
ND = Not determined

LITERATURE REFERENCES TO EXAMPLE 8

Anderson H. C., Sipe J. B., Hessle L., Dhanyamraju R., Atti E., Camacho N. P., Millán J. L. Impaired calcification around matrix vesicles of growth plate and bone in alkaline phosphatase-deficient mice. Am. J. Pathol. 2004; 164(3):841-847.

Bouxsein M L, Boyd S K, Christiansen B A, Guldberg R E, Jepsen K J and Müller R. Guidelines for assessment of bone microstructure in rodents using micro-computed tomography. J Bone Miner Res 2010; 25(7):1468-86.

Fedde K N, Blair L, Silverstein, J, Coburn S P, Ryan L M, Weinstein R S, Waymire K, Narisawa S, Millan, J L, MacGregor G R, Whyte M P, Alkaline phosphatase knockout mice recapitulate the metabolic and skeletal defects of infantile hypophosphatasia. J Bone Miner Res 1999; 14: 2015-2026.

Foster B L, Nagatomo K J, Nociti F H, Fong H, Dunn D, Tran A B, Wang W, Narisawa S, Millán J L, Somerman M J 2012 Central role of pyrophosphate in acellular cementum formation. PLoS One 7(6):e38393.

Foster B. L., Nagatomo K. J., Tso H. W., Tran A. B., Nociti F. H., Jr., Narisawa S., Yadav M. C., McKee M. D., Millan J. I., Somerman M. J. Tooth root dentin mineralization defects in a mouse model of hypophosphatasia. J Bone Miner Res. 2013; 28(2):271-82.

Foster B L, Nociti F H, Jr., Somerman M J (2014a). The rachitic tooth. Endocr Rev 35(1):1-34.

Foster B L, Ramnitz M S, Gafni R I, Burke A B, Boyce A M, Lee J S et al. (2014b).

Rare Bone Diseases and Their Dental, Oral, and Craniofacial Manifestations. J Dent Res 93(7 suppl):7S-19S.

Hessle L., Johnson K. A., Anderson H. C., Narisawa S., Sali A., Goding J. W., Terkeltaub R., Minn J. L. Tissue-nonspecific alkaline phosphatase and plasma cell membrane glycoprotein-1 are central antagonistic regulators of bone mineralization. Proc. Natl. Acad. Sci. U.S.A. 2002; 99(14):9445-9449.

Huesa C., Yadav M. C., Finnilä M. A., Goodyear S. R., Robins S. P., Tanner K. E., Aspden R. M., Millán J. L., Farquharson C. PHOSPHO1 is essential for mechanically competent mineralization and the avoidance of spontaneous fractures. Bone. 2011; 48(5):1066-1074.

Liu J, Nam H K, Campbell C, Gasque K C, Millán J L, Hatch N E. Tissue-nonspecific alkaline phosphatase deficiency causes abnormal craniofacial bone development in the Alpl(-/-) mouse model of infantile hypophosphatasia. Bone 2014; 67:81-94.

McKee M. D., Nakano Y., Masica D. L., Gray J. J., Lemire I., Heft R., Whyte M. P., Crine P., Millán J. L. Enzyme replacement therapy prevents dental defects in a model of hypophosphatasia. J. Dent. Res. 2011; 90(4):470-476.

Meganck J A, Kozloff K M, Thornton M M, Broski S M and Goldstein S A. Beam hardening artifacts in micro-computed tomography scanning can be reduced by X-ray beam filtration and the resulting images can be used to accurately measure BMD. Bone 2009; 45(6):1104-1116.

Millán J L, Narisawa S, Lemire I, Loisel T P, Boileau G, Leonard P, Gramatikova S, Terkeltaub R, Pleshko Camacho N, McKee M D, Crine P and Whyte M P, Enzyme replacement therapy for murine hypophosphatasia. J Bone Miner Res 2008; 23: 777-787.

Narisawa S, Wennberg C. Millán J L, Abnormal vitamin B6 metabolism in alkaline phosphatase knock-out mice causes multiple abnormalities, but not the impaired bone mineralization. J Pathol 2001; 193: 125-133.

Narisawa S, Fröhlander N, Milan J L, Inactivation of two mouse alkaline phosphatase genes and establishment of a model of infantile hypophosphatasia. Dev Dyn 1997; 208: 432-446.

Umoh J U, Sampaio A V, Welch I, Pitelka V, Goldberg H A, Underhill T M et al. In vivo micro-CT analysis of bone remodeling in a rat calvarial defect model. Phys Med Biol 2009; 54(7):2147-61.

Yadav M. C., Lemire I., Leonard P., Boileau G., Blond L., Beliveau M., Cory E., Sah R. L., Whyte M. P., Crine P., Minn J. L. Dose response of bone-targeted enzyme replacement for murine hypophosphatasia. Bone. 2011; 49(2):250-256.

Yadav M. C., de Oliveira R. C., Foster B. L., Fong H., Cory E., Narisawa S., Sah R. L., Somerman M., Whyte M. P., Millán J. L. Enzyme replacement prevents enamel defects in hypophosphatasia mice. J. Bone Miner. Res. 2012; 27(8):1722-1734.

Yadav, M. C., Huesa, C., Narisawa, S., Hoylaerts, M. F., Moreau, A., Farquharson, C. and Millán, J. L. Ablation of osteopontin improves the skeletal phenotype of Phospho 1$^{-/-}$ mice. J. Bone Miner. Res. In Press (2014).

Example 9

Alkaline Phosphatase Protects Against Renal Inflammation

Methods

Cell Culture

Routinely, ciPTEC were cultured at 33° C. (Wilmer, 2010). Cells were transfected with Simian Virus 40 T-antigen and the essential catalytic subunit of human telomerase, allowing them to constantly proliferate. Cells were cultured in DMEM/Ham's F-12, phenolred-free (Gibco, Paisly, United Kingdom), supplemented with ITS (5 μg/ml insulin, 5 µg/ml transferrin, 5 ng/ml selenium; Sigma-Aldrich, Zwijndrecht, The Netherlands), 36 ng/ml hydrocortisone (Sigma-Aldrich), 10 ng/ml epidermal growth factor (Sigma-Aldrich), 40 µg/ml tri-iodothyronine and 10% fetal calf serum (Greiner Bio-One, Kremsmunster, Austria). Preceding an experiment, cells were seeded in a well-plate (48400 cells/cm$^2$), incubated for 1 day at 33° C. followed by a 7-day maturation period at 37° C. On the day of the experiment, cells were pre-incubated for two hrs with LVL-RecAP (1, 5 or 10 U/ml, kind gift from AM-Pharma, Bunnik, The Netherlands) (Kiffer-Moreira, 2014), followed by incubation for 24 hrs with 10 µg/ml LPS (E. coli 0127:B8; Sigma-Aldrich) dissolved in 10 mM HEPES HBSS, pH 7.4 (HEPES: Roche Diagnostics, Mannheim, Germany; HBSS: Gibco). Alternatively, 10 U/ml LVL-RecAP (~17 µg/ml) was administered to LPS-incubated cells simultaneously or after two hrs. Control cells were incubated with culture medium solely. DLPS (E. coli 055:B5; Sigma-Aldrich, 10 µg/ml) and inactive LVL-RecAP (17 µg/ml, kind gift from AM-Pharma) were used as negative controls. In different sets of experiments, LPS was substituted for human TNF-α recombinant protein (Ebioscience, Vienna, Austria), or supernatant of PBMCs, prestimulated for 24 hrs with or without LPS (1 ng/ml). All experiments (n=5) were minimally performed in duplicate.

Isolation of Peripheral Blood Mononuclear Cells

PBMCs were isolated from buffy coats obtained from healthy blood donors (blood bank Nijmegen, n=5) by differential centrifugation over Ficoll-Pague Plus (GE Healthcare, Diegem, Belgium). PBMCs were resuspended in RPMI-1640 medium (Gibco) enriched with 0.5 mg/ml gentamicin (Sigma-Aldrich), 1 mM pyruvate (Gibco) and 2 mM glutamax (Gibco). Cells were seeded in 96-well plates at a density of $0.5 \times 10^6$ cells/well, pre-incubated with or without AP (10 units/ml) for 2 hrs, followed by LPS incubation (1 ng/ml) for 24 hrs. All experiments were performed in duplicate.

ATP Measurement and Cell Viability Assay

Supernatant was collected 30 minutes after LPS administration, with or without LVL-RecAP-pretreatment, followed by direct measurement of ATP production using the ATP Bioluminescence Assay Kit CLS II (Roche Diagnostics) according to manufacturer's protocol. Cell viability was assessed after 24 hrs of LPS incubation by performing the MTT assay. In short, medium was substituted for 100 µl prewarmed MTT-solution (Sigma-Aldrich; 0.5 mg/ml in culture medium), incubated for 3 hrs at 37° C., followed by the addition of 200 µl DMSO to solubilize intracellular precipitated formazan crystals. Dye extinction was measured at 570 nm with wavelength correction of 670 nm.

Animal Model

Animal experiments were performed according to the National Institutes of Health guidelines and protocols were approved by the institutional review board for animal experiments. Male specific-pathogen free Sprague-Dawley rats (RjHan:SD; Janvier, France) were divided into three groups: placebo (n=6), LPS (n=6) or LPS+LVL-RecAP (n=6). A baseline plasma sample (lithium-heparin blood) was collected seven days preceding the experiment through a tail vein puncture using a Multivette (Sarstedt, Etten-Leur, the Netherlands). Three days preceding the experiment, the baseline renal function was assed as FITC-sinistrin $t_{1/2}$ (Schock-Kusch, 2011). At t=0 hrs, placebo (0.9% NaCl, saline) or 0.3 mg/kg BW LPS (E. coli 0127:B8, dissolved in saline) was administered as an IV bolus to induce LPS-induced renal failure. At t=1.5 hrs plasma was obtained as described above. At t=2 hrs, rat received an IV bolus of placebo or LVL-RecAP (1000 U/kg BW, diluted in saline) followed by a second measurement of renal function. At t=5 hrs, all animals received 5 ml saline (s.c.) to prevent dehydration, followed by a 16 hour urine collection period. At t=21.5 hrs the third transcutaneous measurement was performed. At t=24 hrs, rats were anesthetized (i.p., 3 mg/kg BW xylazine and 80 mg/kg BW ketamine 10%), a retrobulbar lithium-heparin blood sample was withdrawn to obtain plasma, and whole body perfusion was started (6 min, saline+50 IU/ml heparin, 210 mbar; 3 min, 4% paraformaldehyde (PFA; 210 mbar). After saline perfusion, the right kidney was carefully removed, snap frozen and stored at −80° C. until processing. The left kidney, removed after PFA perfusion, was stored in 4% PFA at 4° C. until processed for histology and immunohistochemistry. One animal from the LPS+LVL-RecAP group and one urine sample from the placebo group were excluded due to injection and collection difficulties, respectively.

Renal Function Measurements

Renal function was assessed in freely moving awake rats through transcutaneously measured elimination kinetics of FITC-sinistrin (Fresenius Kabi, Linz, Austria), a commercially available marker of GFR, by using a novel measurement device as published before (Schock-Kusch 2011, Schock-Kusch 2009). Briefly, rats were anesthetized by isoflurane inhalation (5% induction, 1.5-2% maintenance; Abbott Laboratories, Illinois, USA) and shaved on the back. The optical part of the device was fixed on this depilated region using a specifically designed double-sided adhesive patch (Lohmann GmbH, Neuwied, Germany), whereas the electronic part of the device was incorporated into a rodent jacket (Lomir Biomedical, Malone, USA). After establishing the baseline signal, FITC-sinistrin (5 mg per 100 g BW, diluted in buffered saline) was injected in the tail vein. Thereafter, the animals were allowed to recover from anesthesia while the measurement continued for approximately 120 minutes post-injection. $T_{1/2}$ was calculated by a one-compartment model applied on the transcutaneously measured FITC-sinistrin elimination kinetics (Schock-Kusch, 2009). In addition, parameters of renal function were determined in plasma and urine samples using the Hitachi 704 automatic analyzer (Boehringer Mannheim, Mannheim, Germany). Fractional urea excretion and endogenous creatinine clearance were calculated with average plasma values of t=1.5 and t=24.

Histology and Immunohistochemistry

After fixation for at least 24 hrs, tissue was processed, embedded in paraplast and sectioned at 3 µM thickness. For routine histology, HE staining was performed on renal tissue. Renal injury was assessed using a scoring system with a scale from 0 to 4 (0=no changes; 4=severe damage e.g. marked tubule cell changes). KIM-1 was detected by primary antibody goat-anti-rat KIM-1 (1:50; AF3689, R&D Systems, Abingdon, UK) and secondary antibody rabbit-anti-goat IgG (1:200; P0449, DAKO, Heverlee, Belgium). Immunostaining was visualized with VECTASTAIN Eline ABC system reagents (Vector Labs, Amsterdam, Netherlands) and 3,3'-Diaminobenzidine (DAB, Sigma-Aldrich), followed by haematoxyline counterstain. All scoring was performed in a blinded fashion.

Cytokines and Renal Injury Markers

Human ELISA kits (R&D Systems) were used to determine TNF-α, IL-6 and IL-8 in supernatant according to manufacturer's instructions. Plasma cytokine levels (IL-1β, IL-6, IL-10, TNF-α, INF-γ) were determined by a simultaneous Luminex assay according to the manufacturer's instructions (Millipore, Cork, Ireland). KIM-1 and NGAL were determined by ELISA (R&D Systems) according to manufacturer's instructions.

Tissue Homogenization

Snap frozen kidneys were homogenized by the TissueLyser LT (Qiagen, Venlo, The Netherlands) according to manufacturer's instructions, in Tissue Protein Extraction Reagent (T-PER; Thermo Scientific, Rockford, USA), supplemented with complete EDTA-free protease inhibitor cocktail tablets (Roche Applied Science, Almere, The Netherlands). Total protein content was determined using the bicinchonicic acid protein assay kit (Thermo Scientific) and samples were stored at −80° C. until assayed.

Real-Time PCR Analyses

RNA was extracted from frozen cell pellet or pulverized kidneys (2000, 30 sec; Mikro-dismembrator U, Sartorius Stedim Biotech, Aubagne Cedex, France) by Trizol reagent. RNA was reverse-transcribed into cDNA using Moloney Murine Leukemia Virus (M-MLV) Reverse Transcriptase (Invitrogen, Breda, The Netherlands). Real-time quantitative PCR (RQ-PCR) was performed using Taqman® (Applied Biosystems, Carlsbad, USA). Genes were amplified and normalized to the expression of GAPDH (ciPTEC: Ct: 18.9±0.1; renal tissue: Ct: 24.8±0.2). The PCR reaction started with a 2 min incubation step at 50° C. followed by initial denaturation for 10 min at 95° C., and 40 cycles of 15 sec at 95° C. and 1 min at 60° C. Differences between groups were calculated by the comparative ΔΔCt method. Primers/probe sets are summarized in Table 17.

Urinary Purine Content

Urinary adenosine, AMP, ADP, ATP and cAMP content was determined by HPLC. In brief, 4 volumes of urine were mixed with 1 volume of chloroacetaldehyde (6× diluted in 1M acetate buffer, pH 4.5; Sigma-Aldrich), followed by derivatization (60 min, 70° C., 500 rpm) and centrifugation (3 min, RT, 13400 rpm), whereafter the supernatant was transferred to a HPLC vial and injected. Purines were separated by HPLC system (Thermo Scientific) using a Polaris C18-A column (150×4.6 mm) with gradient elution using eluent A (0.1M $K_2HPO_4$, 10 mM TBAHS (pH 6.5), and 2% MeOH) and eluent B ($H_2O$: ACN: THF; 50:49:1). Retention times were 7.1 (adenosine), 8.4 (AMP), 12.5 (ADP), 16.2 (ATP) and 14.8 min (cAMP). Quantification was based on peak areas of the samples and reference standards measured with fluorescence (excitation: 280 nm; emission: 420 nm).

Statistical Analysis

Data are expressed as mean±SEM or median [25th percentile, 75th percentile]. Normality of data was assessed by Kolmogorov-Smirnov test. Statistical differences between groups were estimated by ANOVA with post-hoc comparisons using Bonferroni's multiple comparison test or by Kruskal-Wallis test with Dunn's post-test. A two-sided p-value less than 0.05 was considered statistically significant. All tests were performed with Graphpad Prism 5.00 for Windows (Graphpad Software Inc. San Diego, Calif., USA).

LVL-RecAP Attenuates the LPS-Induced Inflammatory Response In Vitro

Pre-treatment of human ciPTEC (Wilmer, 2010) with LVL-RecAP dose-dependently attenuated the LPS-induced cytokine production of TNF-α, IL-6 and IL-8 on the gene and protein level (FIG. 12A-12F). Detoxified LPS (dLPS) was used as a negative control and had no effect. Similar protective results at the protein level were obtained when LVL-RecAP was administered simultaneously with LPS or 2 hrs after LPS exposure (FIG. 12G-12I). A control experiment was performed to verify whether LVL-RecAP dephosphorylates the cytokines excreted in the medium, which was not the case (FIG. 17A-17C). To confirm that the LVL-RecAP-induced reduction in cytokine production was due to the dephosphorylating nature of the enzyme, the effect of inactive LVL-RecAP that lacks hydrolyzing properties was investigated. Inactive LVL-RecAP did not attenuate the LPS-induced inflammatory response in ciPTEC (FIG. 12J-12L).

The In Vitro Effects of LVL-RecAP are Renal Specific and not Restricted to LPS-Induced Inflammation To investigate further the renal protective mechanism of LVL-RecAP, ciPTEC were incubated with the pro-inflammatory cytokine TNF-α, which cannot be dephosphorylated by calf IAP (Chen, 2010). The TNF-α induced cytokine production of IL-6 and IL-8 was also attenuated by LVL-RecAP pretreatment, whereas inactive LVL-RecAP had no effect (FIG. 13A-13B).

In the pathogenesis of sepsis-associated AKI, LPS induces a local inflammatory response through binding to TLR4 expressed on PTEC (ciPTEC Ct: 30.5±3.9; n=5). Another hallmark of the disease is the systemic inflammatory response, which affects both renal epithelial and endothelial cells causing the development of AKI (Peters, 2014). To mimic this endotoxin-induced renal inflammation, ciPTEC were incubated with the supernatant of LPS-stimulated peripheral blood mononuclear cells (PBMCs, 1 ng/ml LPS). This induced the production of IL-6 and IL-8, which was decreased when ciPTEC were pretreated with LVL-RecAP (FIG. 13C-13D, TNF-α was not detectable). Together with the finding that inflammatory responses mediated by TNF-α were attenuated by LVL-RecAP treatment, this suggests the presence of another mediator targeted by LVL-RecAP. In contrast, pretreatment of PBMCs with LVL-RecAP did not affect the LPS-induced inflammatory response in these cells (FIG. 13E-13F), indicating that the effects of LVL-RecAP are kidney specific.

LVL-RecAP May Exert Renal Protective In Vitro Effects Through the ATP/Adenosine Pathway A second potential target of LVL-RecAP is ATP, released during cell stress caused by e.g. inflammation and hypoxia (Eltzschig, 2012). Extracellular ATP has detrimental effects, but can be converted by ectonucleotidases (e.g. AP) into ADP, AMP and eventually into adenosine, exerting anti-inflammatory and tissue-protective effects through binding to one of the adenosine receptors A1, A2A, A2B and A3 (Bauerle, 2011, Di Sole, 2008). Interestingly, while the adenosine receptors A1, A2B and A3 expression in ciPTEC were not affected by LPS incubation (data not shown), the A2A expression was up-regulated upon LPS stimulation (fold increase: 4.1±0.4; p<0.001 compared to placebo). This effect was attenuated by LVL-RecAP co-treatment (fold increase: 2.9±0.2; p<0.001 compared to placebo; p<0.05 compared to LPS), suggesting a role of the adenosine pathway in the protective effect of LVL-RecAP. Furthermore, we observed increased extracellular ATP concentrations following LPS incubation, which was more pronounced with a higher LPS concentration but reversed by LVL-RecAP preincubation (FIG. 14). LPS did not affect cell viability up to 24 hrs (data not shown). This supports the hypothesis that LVL-RecAP may exert its renal protective effect through the ATP/adenosine pathway.

LVL-RecAP Treatment During LPS-Induced AKI in Rats Attenuates Impaired Renal Function To confirm the beneficial effects of LVL-RecAP in vivo, AKI was induced in rats by LPS (0.3 mg/kg BW) and renal function was assessed by the transcutaneous measurement of the fluorescein isothiocyanate (FITC)-labeled sinistrin kinetics as previously reported (Schock-Kusch, 2011). FITC-sinistrin is cleared by the kidneys through filtration solely and its disappearance from the plasma compartment can be measured transcutaneously in real-time (Schock-Kusch, 2011, Schock-Kusch, 2009). This allows investigating the progression of AKI in a more accurate manner as compared to the commonly used creatinine clearance. Preceding LPS injection, a baseline blood sample was drawn to determine clinical parameters and plasma cytokines, and the baseline FITC-sinistrin half-life ($t_{1/2}$) was determined from the measured kinetics to ascertain homogeneity between groups (data not shown). After 1.5 hrs, LPS treatment resulted in increased plasma cytokines levels, abnormalities in several plasma parameters (Table 18), piloerection, diarrhea and reduced spontaneous activity, confirming the presence of systemic inflammation. Two hrs after LPS administration, rats were treated with LVL-RecAP (1000 U/kg BW) or placebo (saline), directly followed by transcutaneous renal function measurements. LPS significantly prolonged FITC-sinistrin $t_{1/2}$, revealing a significant reduction in renal function. This trend was attenuated by LVL-RecAP treatment (FIG. 15A). In all groups, renal function was fully recovered within 24 hrs (FIG. 15B). Still, plasma urea levels were significantly lower in LVL-RecAP treated animals compared to animals that received LPS without LVL-RecAP (Table 19). Also, LVL-RecAP treatment prevented the LPS-induced increase of fractional urea excretion (FIG. 15C) and the LPS-induced decrease of endogenous creatinine clearance (FIG. 15D). LVL-RecAP bio-activity was confirmed in plasma and showed an eightfold increase 22 hrs after injection (Placebo: 293±12 U/ml; LPS: 260±13 U/ml; LPS+AP: 2150±60 U/ml; p<0.0001).

LVL-RecAP Prevents Renal Injury During LPS-Induced AKI In Vivo

The renal protective effect of LVL-RecAP on LPS-induced AKI was investigated further through evaluation of renal histology and specific tubular injury markers. No differences in histology were found between the treatment groups, with changes that ranged from no damage (0) till minimal degenerative changes like foamy appearance and minimal swelling of proximal tubular cells (1) and foamy appearance and moderate swelling as well as a few cases of apoptosis (2) (Placebo: 1 [0.75-2]; LPS: 1.5 [0-2]; LPS+LVL-RecAP: 1 [0-1.0]). LPS treatment resulted in a significant increase in renal IL-6 expression levels, while other cytokines and injury markers (MPO, myeloperoxidase; BAX, Bcl2-associated X protein; iNOS, inducible nitric oxide synthase) were not affected (Table 20). LVL-RecAP could not reduce renal IL-6 expression levels, but did enhance renal expression of the anti-inflammatory cytokine IL-10 (Table 20). Furthermore, LPS administration resulted in a significant increase in the urinary excretion of kidney injury molecule (KIM)-1 and neutrophil gelatinase-associated lipocalin (NGAL), which was accompanied by increased renal gene expression levels. This effect was prevented by LVL-RecAP co-administration (FIG. 16A-16B, Table 20). Similar effects of LVL-RecAP were observed for plasma NGAL levels (FIG. 16C) and for renal protein levels of KIM-1 (FIG. 16D), which was localized primarily to the apical surface of proximal tubule epithelial cells (FIG. 16E).

Reduced Urinary Adenosine Excretion During LPS-Induced AKI In Vivo

In order to elucidate further the renal protective mechanism of LVL-RecAP, we investigated the role of the ATP-adenosine pathway. LPS treatment tended to reduce the gene expression levels in the kidney for all four adenosine receptors, of which only adenosine receptor A3 reached statistical significance (Table 20). Interestingly, LPS treatment significantly decreased the urinary excretion of adenosine (placebo: 68.0±7.8 μg adenosine/10 μg creatinine; LPS: 19.4±6.3 pg adenosine/10 μg creatinine; p<0.001), without altering the excretion of cAMP, ATP, ADP and AMP (data not shown). This may suggest that the kidney utilizes adenosine during LPS-induced AKI. LVL-RecAP treatment had no effect on adenosine receptor gene expression (Table 20), or on urinary adenosine excretion (LPS+LVL-RecAP: 16.7±6.8 pg adenosine/10 μg creatinine: p<0.001 compared to placebo) compared to LPS alone.

TABLES

TABLE 17

Primer/probe specifications

| Gene symbol | Gene name | Assay ID |
|---|---|---|
| ciPTEC | | |
| GAPDH | glyceraldehyde-3-phosphate dehydrogenase | Hs02758991_g1 |
| TNF-α | tumor necrosis factor | Hs01113624_g1 |
| IL-6 | interleukin 6 | Hs00985639_m1 |
| IL-8 | interleukin 8 | Hs00174103_m1 |
| TLR4 | toll-like receptor 4 | Hs00152939_m1 |
| ADORA1 | adenosine A1 receptor | Hs00379752_m1 |
| ADORA2A | adenosine A2a receptor | Hs00169123_m1 |
| ADORA2B | adenosine A2b receptor | Hs00386497_m1 |
| ADORA3 | adenosine A3 receptor | Hs01560269_m1 |
| Rat kidney | | |
| GAPDH | glyceraldehyde-3-phosphate dehydrogenase | Rn01775763_g1 |
| IL-1β | interleukin 1 beta | Rn00580432_m1 |
| IL-6 | interleukin 6 | Rn01410330_m1 |
| IL-10 | interleukin 10 | Rn00563409_m1 |
| TNF-α | tumor necrosis factor | Rn99999017_m1 |
| IFN-γ | interferon gamma | Rn00594078_m1 |
| HAVCR1 | hepatitis A virus cellular receptor 1 | Rn00597703_m1 |
| LCN2 | lipocalin 2 | Rn00590612_m1 |
| MPO | myeloperoxidase | Rn01460204_m1 |
| BAX | Bcl2-associated X protein | Rn02532082_g1 |
| NOS2 | nitric oxide synthase 2, inducible | Rn00561646_m1 |
| ADORA1 | adenosine A1 receptor | Rn00567668_m1 |
| ADORA2A | adenosine A2a receptor | Rn00583935_m1 |
| ADORA2B | adenosine A2b receptor | Rn00567697_m1 |
| ADORA3 | adenosine A3 receptor | Rn00563680_m1 |

TABLE 18

Plasma cytokines and experimental parameters

| | Placebo | LPS | LPS + recAP |
|---|---|---|---|
| Cytokines | | | |
| IL-1β (pg/ml) | 9 ± 9 | 6913 ± 1362[#] | 5764 ± 1259[#] |
| IL-6 (pg/ml) | ND | 74294 ± 11240[#] | 70247 ± 13812[#] |

TABLE 18-continued

Plasma cytokines and experimental parameters

|  | Placebo | LPS | LPS + recAP |
|---|---|---|---|
| IL-10 (pg/ml) | 17 ± 17 | 10054 ± 2017# | 8693 ± 2513# |
| TNF-α (pg/ml) | 1 ± 1 | 21071 ± 3375# | 10514 ± 889#* |
| INF-γ (pg/ml) | ND | ND | ND |
| Plasma parameters | | | |
| Creatinine (mg/dl) | 0.16 ± 0.01 | 0.30 ± 0.05 | 0.25 ± 0.04 |
| Urea (mg/dl) | 28 ± 2 | 39 ± 2# | 48 ± 3#* |
| Lactate (mg/dl) | 24 ± 5 | 34 ± 2 | 33 ± 3 |
| Glucose (mg/dl) | 143 ± 3 | 260 ± 25# | 216 ± 13# |
| Protein (mg/ml) | 58 [56-58] | 58 [48-61] | 56 [56-58] |
| Calcium (mmol/l) | 2.59 ± 0.03 | 2.43 ± 0.03# | 2.41 ± 0.06# |
| Inorganic Phosphorus (mmol/l) | 3.01 ± 0.10 | 2.76 ± 0.09 | 2.81 ± 0.10 |
| Sodium (mmol/l) | 149 ± 2 | 148 ± 2 | 146 ± 3 |
| Potassium (mmol/l) | 5.89 [5.66-6.21] | 4.87 [4.66-5.23] | 5.08 [4.76-5.18] |

Plasma parameters were determined 1.5 hrs after LPS administration. Data is expressed as mean ± SEM, and median [$25^{th}$ percentile, $75^{th}$ percentile], depending on the distribution of each parameter. Differences in distribution of plasma paramaters compared to t = 24 is likely to be related to sample size. Significant differences estimated using one-way ANOVA with Bonferroni post-test, or Kruskal-Wallis test with Dunns post-test.
Placebo, LPS n = 6; LPS + recAP n = 5.
p < 0.05 compared to placebo.
*p < 0.05 compared to LPS.
LPS, Lipopolysaccharide;
recAP, recombinant Alkaline Phosphatase;
ND: not detected.

TABLE 19

Plasma and urinary parameters

|  | Placebo | LPS | LPS + recAP |
|---|---|---|---|
| Plasma parameters | | | |
| Creatinine (mg/dl) | 0.20 ± 0.01 | 0.24 ± 0.02 | 0.20 ± 0.01 |
| Urea (mg/dl) | 28 ± 2 | 48 ± 4# | 36 ± 2* |
| Lactate (mg/dl) | 10 [8-31] | 14 [12-21] | 12.0 [10-14] |
| Glucose (mg/dl) | 144 ± 7 | 132 ± 11 | 161 ± 3 |
| Protein (mg/ml) | 56 [54-57] | 56 [52-57] | 54 [54-58] |
| Calcium (mmol/l) | 2.84 [2.7-3.1] | 2.65 [2.6-2.7] | 2.70 [2.6-2.8] |
| Inorganic Phosphorus (mmol/l) | 2.95 ± 0.09 | 3.06 ± 0.10 | 2.95 ± 0.09 |
| Sodium (mmol/l) | 150 [148-157] | 154 [147-155] | 150 [141-154] |
| Potassium (mmol/l) | 4.24 ± 0.04 | 4.32 ± 0.10 | 4.42 ± 0.24 |
| Urinary parameters | | | |
| Creatinine (mg) | 5.4 ± 0.3 | 6.1 ± 0.3 | 5.7 ± 0.6 |
| Urea (mg) | 267 ± 26 | 482 ± 21# | 440 ± 19# |
| Albumin (μg) | 0 [0-54] | 0 [0-663] | 310 [0-419] |
| Glucose (mg) | 1.59 ± 0.25 | 1.74 ± 0.28 | 0.99 ± 0.27 |
| Protein (μg) | 38 ± 6 | 67 ± 9 | 61 ± 9 |
| Calcium (μmol) | 4.1 ± 0.7 | 7.2 ± 0.9 | 7.4 ± 1.7 |
| Inorganic Phosphorus (mmol) | 0.50 [0.3-0.9] | 0.63 [0.6-1.0] | 0.64 [0.6-0.8] |
| Sodium (mmol) | 1.6 [1.3-2.0] | 1.5 [1.3-1.7] | 1.5 [1.4-2.4] |
| Potassium (mmol) | 1.6 ± 0.3 | 2.3 ± 0.4# | 1.9 ± 0.1# |

Plasma parameters were determined 24 hrs after LPS administration. Urinary parameters were determined between 5 and 21 hrs after LPS administration. Data is expressed as mean ± SEM, and median [$25^{th}$ percentile, $75^{th}$ percentile], depending on the distribution of each parameter. Significant differences estimated using Kruskal-Wallis test with Dunns post-test or one-way ANOVA with Bonferroni post-test.
Placebo, LPS n = 6; LPS + recAP n = 5; urinary parameters: Placebo n = 5.
p < 0.05 compared to placebo.
*p < 0.05 compared to LPS.
LPS, Lipopolysaccharide;
recAP, recombinant Alkaline Phosphatase.

TABLE 20

Renal gene expression levels

|  | Ct values | | | Fold increase (2^ΔΔCt) | | |
| --- | --- | --- | --- | --- | --- | --- |
|  | Placebo | LPS | LPS + recAP | Placebo | LPS | LPS + recAP |
| Cytokines | | | | | | |
| IL-1β | 27.7 ± 0.5 | 26.6 ± 0.2 | 26.9 ± 0.3 | 1.1 ± 0.2 | 1.6 ± 0.5 | 1.7 ± 0.5 |
| IL-6 | 37.4 [36.3-38.0] | 33.5 [33.3-34.8] | 34.7 [34.4-36.4] | 1.2 ± 0.3 | 4.9 ± 0.5[#] | 5.2 ± 1.2[#] |
| IL-10 | 34.8 ± 0.4 | 32.5 ± 0.1 | 32.9 ± 0.3 | 1.1 ± 0.2 | 3.3 ± 0.9 | 5.5 ± 1.2[#] |
| TNF-α | 36.7 ± 0.2 | 35.8 ± 0.4 | 37.2 ± 0.5 | 1.1 ± 0.2 | 1.0 ± 0.1 | 1.0 ± 0.3 |
| INF-γ | 36.3 ± 0.3 | 35.3 ± 0.4 | 35.6 ± 0.2 | 1.1 ± 0.2 | 1.3 ± 0.3 | 1.7 ± 0.2 |
| Injury markers | | | | | | |
| KIM-1 | 31.7 ± 0.4 | 22.9 ± 0.7 | 25.3 ± 0.6 | 0.8 [0.6-1.9] | 430 [195-530][#] | 113 [43-336] |
| NGAL | 29.1 ± 0.2 | 24.1 ± 1.4 | 25.5 ± 1.6 | 1.2 ± 0.3 | 33 ± 9[#] | 28 ± 8 |
| MPO | 32.4 ± 0.3 | 31.4 ± 0.7 | 33.0 ± 1.0 | 1.0 [0.4-2.9] | 1.4 [0.4-3.9] | 0.6 [0.3-3.2] |
| BAX | 25.2 ± 0.2 | 24.8 ± 0.1 | 25.1 ± 0.3 | 0.9 [0.7-1.5] | 0.7 [0.3-2.1] | 1.0 [0.5-1.3] |
| iNOS | 36.2 ± 0.5 | 35.0 ± 0.2 | 34.8 ± 0.8 | 1.1 ± 0.3 | 1.8 ± 0.5 | 2.6 ± 0.8 |
| Adenosine receptors | | | | | | |
| A1 | 28.6 ± 0.3 | 27.9 ± 0.3 | 29.3 ± 0.6 | 1.3 [0.4-2.3] | 0.7 [0.5-1.4] | 0.8 [0.3-1.5] |
| A2A | 27.0 ± 0.1 | 26.4 ± 0.2 | 27.3 ± 0.3 | 1.3 ± 0.4 | 0.8 ± 0.2 | 0.9 ± 0.2 |
| A2B | 29.0 [28.9-29.3] | 28.4 [28.1-29.0] | 29.0 [28.9-30.2] | 1.2 ± 0.3 | 0.8 ± 0.2 | 0.8 ± 0.1 |
| A3 | 34.3 ± 0.3 | 34.2 ± 0.4 | 35.0 ± 0.6 | 1.0 ± 0.1 | 0.5 ± 0.1[#] | 0.7 ± 0.1 |

Data is expressed as mean ± SEM, and median [25th percentile, 75th percentile], depending on the distribution of each parameter. Significant differences of the fold increase was estimated using Kruskal-Wallis test with Dunns post-test or one-way ANOVA with Bonferroni post-test.
Placebo, LPS n = 6; LPS + recAP n = 5.
[#]$p < 0.05$ compared to placebo.
* $p < 0.05$ compared to LPS.
LPS, Lipopolysaccharide;
recAP, recombinant Alkaline Phosphatase;
MPO, myeloperoxidase;
BAX, Bcl2-associated X protein;
iNOS, inducible nitric oxide synthase.

LITERATURE REFERENCES TO EXAMPLE 9

Bauerle, J. D., Grenz, A., Kim, J. H., Lee, H. T., and Eltzschig, H. K. 2011. Adenosine generation and signaling during acute kidney injury. J Am Soc Nephrol 22:14-20.

Chen, K. T., Malo, M. S., Moss, A. K., Zeller, S., Johnson, P., Ebrahimi, F., Mostafa, G., Alam, S. N., Ramasamy, S., Warren, H. S., et al. 2010. Identification of specific targets for the gut mucosal defense factor intestinal alkaline phosphatase. Am J Physiol Gastrointest Liver Physiol 299:G467-475.

Di Sole, F. 2008. Adenosine and renal tubular function. Curr Opin Nephrol Hypertens 17:399-407.

Eltzschig, H. K., Sitkovsky, M. V., and Robson, S. C. 2012. Purinergic signaling during inflammation. N Engl J Med 367:2322-2333.

Kiffer-Moreira, T., Sheen, C. R., Gasque, K. C., Bolean, M., Ciancaglini, P., van Elsas, A., Hoylaerts, M. F., and Milan, J. L. 2014. Catalytic signature of a heat-stable, chimeric human alkaline phosphatase with therapeutic potential. PLoS One 9:e89374.

Peters, E., Heemskerk, S., Masereeuw, R., and Pickkers, P. 2014. Alkaline Phosphatase: A Possible Treatment for Sepsis-Associated Acute Kidney Injury in Critically Ill Patients. Am J Kidney Dis. 63:1038-48

Schock-Kusch, D., Sadick, M., Henninger, N., Kraenzlin, B., Claus, G.,
Kloetzer, H. M., Weiss, C., Pill, J., and Gretz, N. 2009. Transcutaneous measurement of glomerular filtration rate using FITC-sinistrin in rats. Nephrol Dial Transplant 24:2997-3001.

Schock-Kusch, D., Xie, Q., Shulhevich, Y., Hesser, J., Stsepankou, D., Sadick, M., Koenig, S., Hoecklin, F., Pill, J., and Gretz, N. 2011. Transcutaneous assessment of renal function in conscious rats with a device for measuring FITC-sinistrin disappearance curves. Kidney Int 79:1254-1258.

Wilmer, M. J., Saleem, M. A., Masereeuw, R., Ni, L., van der Velden, T. J., Russel, F. G., Mathieson, P. W., Monnens, L. A., van den Heuvel, L. P., and Levtchenko, E. N. 2010. Novel conditionally immortalized human proximal tubule cell line expressing functional influx and efflux transporters. Cell Tissue Res 339:449-457.

Example 10

Comparison LVL-RecAP with RecAP Under Different Temperature Conditions 10.6. Materials
10.6.1 Reference Standards
LVL-RecAP
Batch number NB1963p1
PRA ID 14-049
Protein content 9.9 mg/mL (OD280)
Activity 6537 U/mL (660 U/mg)
Storage condition: nominal at −70° C.
Expiry date 8 Jan. 2015
RecAP
Batch number 2013-052, lot 62
PRA ID 14-311
Protein content 13.3 mg/mL (OD280)
Activity 9871 U/mL (742 U/mg)
Storage condition: at 2-8° C.
Expiry date 6 Jun. 2016
10.6.2 Blank Matrix
The following biological matrix was used for preparation of sample solutions.

Matrix: serum
Species: human
Supplier: Sera Laboratories International, Haywards Heath, UK
Storage condition: At a nominal storage temperature −20° C.
PRA IDs: 14-0624, 14-0647 and 14-0652
Expiry dates: 2 May 2016 (14-0624), 6 May 2016 (14-0647 and 14-0652)

10.7. Methods 10.7.1 Preparation of Solutions 10.7.1.1 2 M Sodium Hydroxide

A 2 molar sodium hydroxide solution was prepared by dissolving 8 g of sodium hydroxide in approximately 90 mL Milli-Q water and after cooling to room temperature the volume was adjusted to 100 mL. The solution was stored at room temperature up to a maximum of one month.

10.7.1.2 1 M Magnesium Chloride

A 1 molar magnesium chloride solution was prepared by dissolving 4.06 g magnesium chloride hexahydrate in approximately 16 mL Milli-Q water. After dissolving the volume was adjusted to 20 mL. The solution was stored at nominal +4° C. up to a maximum of one month.

10.7.1.3 0.1 M Zinc Chloride

A 0.1 molar zinc chloride solution was prepared by dissolving 272.5 mg zinc chloride in approximately 16 mL Milli-Q water. After dissolving, the volume was adjusted to 20 mL.

The solution was stored at nominal +4° C. up to a maximum of one month.

10.7.1.4 0.025M Glycine pH 9.6 Solution for 25° C. Method

A 0.025 molar glycine pH 9.6 solution was prepared by dissolving 3.76 g of glycine in approximately 1800 mL Milli-Q water. The solution was warmed to 25° C. and adjusted to pH 9.6 with 2 M sodium hydroxide (see Section 10.7.1.1). The volume was made up to 2000 mL and the pH was rechecked. The pH should be pH 9.6 at 25° C. The solution was stored at nominal +4° C. up to a maximum of one week.

10.7.1.5 Enzyme Diluent Buffer for 25° C. Method

The enzyme diluent buffer was prepared by mixing 0.5 mL 1 M magnesium chloride (see Section 10.7.1.2) with 0.5 mL 0.1 M zinc chloride (see Section 10.7.1.3) and 500 mL 0.025 M glycine pH 9.6 solution (see Section 10.7.1.4). To this solution, 5.00 g mannitol and 0.25 g bovine serum albumin was added and dissolved under stirring. The pH was checked and if deemed necessary adjusted to pH 9.6 at 25° C. using 2 M sodium hydroxide. The enzyme diluent buffer was prepared freshly every day.

10.7.1.6 0.0103 M p-Nitrophenyl Phosphate pH 9.6 for 25° C. Method

A 0.0103 M p-nitrophenyl phosphate pH 9.6 was prepared by dissolving 1528 mg p-nitrophenyl phosphate in approximately 360 mL 0.025 M glycine pH 9.6 solution (see Section 10.7.1.4). The pH was checked and if deemed necessary adjusted to pH 9.6 at 25° C. using 2 M sodium hydroxide (see Section 10.7.1.1). After checking the pH, the volume was adjusted to 400 mL with 0.025 M glycine pH 9.6 solution. The solution was stored at nominal+4° C. up to a maximum of 5 days.

10.7.1.7 Working Substrate for 25° C. Method

Working substrate was prepared by mixing 120 mL 0.0103 M p-nitrophenyl phosphate pH 9.6 solution (see Section 10.7.1.6) with 1.25 mL 1 M magnesium chloride solution (see Section 10.7.1.2). To this solution approximately 15 mL 0.025 M glycine pH 9.6 solution (see Section 10.7.1.4) was added and the pH was checked and if deemed necessary adjusted to pH 9.6 at 25° C. using 2 M sodium hydroxide (see Section 10.7.1.1). The volume was adjusted to 145 mL with 0.025 M glycine pH 9.6 solution. Working substrate was prepared freshly every day.

10.7.1.8 0.025M Glycine pH 9.6 Solution for 37° C. Method

A 0.025 molar glycine pH 9.6 solution was prepared by dissolving 3.76 g of glycine in approximately 1800 mL Milli-Q water. The solution was warmed to 25° C. and adjusted to pH 9.6 with 2 M sodium hydroxide (see Section 10.7.1.1). The volume was made up to 2000 mL and the pH was rechecked. The pH should be pH 9.6 at 37° C. The solution was stored at nominal+4° C. up to a maximum of one week.

10.7.1.9 Enzyme Diluent Buffer for 37° C. Method

The enzyme diluent buffer was prepared by mixing 0.5 mL 1 M magnesium chloride (see Section 10.7.1.2) with 0.5 mL 0.1 M zinc chloride (see Section 10.7.1.3) and 500 mL 0.025 M glycine pH 9.6 solution (see Section 10.7.1.8). To this solution, 5.00 g mannitol and 0.25 g bovine serum albumin was added and dissolved under stirring. The pH was checked and if deemed necessary adjusted to pH 9.6 at 37° C. using 2 M sodium hydroxide. The enzyme diluent buffer was prepared freshly every day.

10.7.1.10 0.0103 M p-Nitrophenyl Phosphate pH 9.6 for 37° C. Method

A 0.0103 M p-nitrophenyl phosphate pH 9.6 was prepared by dissolving 1528 mg p-nitrophenyl phosphate in approximately 360 mL 0.025 M glycine pH 9.6 solution (see Section 10.7.1.8). The pH was checked and if deemed necessary adjusted to pH 9.6 at 37° C. using 2 M sodium hydroxide (see Section 10.7.1.1). After checking the pH, the volume was adjusted to 400 mL with 0.025 M glycine pH 9.6 solution. The solution was stored at nominal+4° C. up to a maximum of 5 days.

10.7.1.11 Working Substrate for 37° C. Method

Working substrate was prepared by mixing 120 mL 0.0103 M p-nitrophenyl phosphate pH 9.6 solution (see Section 10.7.1.10) with 1.25 mL 1 M magnesium chloride solution (see Section 10.7.1.2). To this solution approximately 15 mL 0.025 M glycine pH 9.6 solution (see Section 10.7.1.4) was added and the pH was checked and if deemed necessary adjusted to pH 9.6 at 37° C. using 2 M sodium hydroxide (see Section 10.7.1.1). The volume was adjusted to 145 mL with 0.025 M glycine pH 9.6 solution. Working substrate was prepared freshly every day.

10.7.2 LVL-RecAP Spike Solution (500 µg/mL)

A recAP spike solution were prepared by diluting 252.5 µL LVL-RecAP (Section 10.6.1) to 5.00 mL with enzyme diluent buffer (Section 10.7.1.5). The final concentration of the spike solution is 500 µg/mL, this solution was used for preparation of the recAP spiked human serum samples (Section 10.7.4).

10.7.3 RecAP Spike Solution (500 µg/mL)

A RecAP spike solution was prepared by diluting 188.0 µL RecAP (Section 10.6.1) to 5.00 mL with enzyme diluent buffer (Section 10.7.1.5). The final concentration of the spike solution is 500 µg/mL, this solution was used for preparation of the RecAP spiked human serum samples (Section 10.7.5).

10.7.4 Preparation of LVL-recAP Spiked Human Serum Samples

Serum samples were prepared by spiking LVL-RecAP to three individual blank serum batches using the following concentration:

| LVL-RecAP serum samples | Concentration (µg/mL) | Calculated activity (U/L) | Spike volume (µL) | Total volume (mL) |
|---|---|---|---|---|
| 1 | 10.0 | 6603 | 100 | 5.00 |
| 2 | 8.00 | 5282 | 80.0 | 5.00 |
| 3 | 6.00 | 3962 | 60.0 | 5.00 |
| 4 | 4.00 | 2641 | 40.0 | 5.00 |
| 5 | 2.00 | 1321 | 20.0 | 5.00 |
| 6 | 1.00 | 660 | 10.0 | 5.00 |
| 7 | endogenous | endogenous | 0 | 5.00 |

The serum samples were stored at nominal −70° C. until analysis.

10.7.5 Preparation of RecAP Spiked Human Serum Samples

Serum samples were prepared by spiking RecAP to three individual blank serum batches using the following concentration:

| RecAP serum samples | Concentration (µg/mL) | Calculated activity (U/L) | Spike volume (µL) | Total volume (mL) |
|---|---|---|---|---|
| 1 | 9.00 | 6680 | 90.0 | 5.00 |
| 2 | 7.20 | 5344 | 72.0 | 5.00 |
| 3 | 5.40 | 4088 | 54.0 | 5.00 |
| 4 | 3.60 | 2672 | 36.0 | 5.00 |
| 5 | 1.80 | 1336 | 18.0 | 5.00 |
| 6 | 0.900 | 668 | 9.00 | 5.00 |
| 7 | endogenous | endogenous | 0 | 5.00 |

The serum samples were stored at nominal −70° C. until analysis.

10.7.6 Preparation of Sample Solutions for LVL-RecAP and RecAP Enzyme Activity

The sample solutions for LVL-RecAP and RecAP enzyme activity were prepared by dilution of the LVL-RecAP product sample or RecAP product sample using enzyme diluent buffer (Section 10.7.1.5 for 25° C. method or Section 10.7.1.9 for 37° C. method).

Sample 1 from LVL-RecAP and/or RecAP sample was diluted by taking 125 µL of the LVL-RecAP and/or RecAP serum sample and diluted to 2.50 mL with enzyme diluent buffer to prepare the final sample solution for LVL-RecAP or RecAP enzyme activity.

Sample 2 from LVL-RecAP and/or RecAP sample was diluted by taking 125 µL of the LVL-RecAP and/or RecAP serum sample and diluted to 2.00 mL with enzyme diluent buffer to prepare the final sample solution for LVL-RecAP or RecAP enzyme activity.

Sample 3 from LVL-RecAP and/or RecAP sample was diluted by taking 167 µL of the LVL-RecAP and/or RecAP serum sample and diluted to 2.00 mL with enzyme diluent buffer to prepare the final sample solution for LVL-RecAP or RecAP enzyme activity.

Sample 4 from LVL-RecAP and/or RecAP sample was diluted by taking 250 µL of the LVL-RecAP and/or RecAP serum sample and diluted to 2.00 mL with enzyme diluent buffer to prepare the final sample solution for LVL-RecAP or RecAP enzyme activity.

Sample 5 from LVL-RecAP and/or RecAP sample was diluted by taking 500 µL of the LVL-RecAP and/or RecAP serum sample and diluted to 2.00 mL with enzyme diluent buffer to prepare the final sample solution for LVL-RecAP and/or RecAP enzyme activity.

Sample 6 from LVL-RecAP and/or RecAP sample was diluted by taking 1000 µL of the LVL-RecAP and/or RecAP serum sample and diluted to 2.00 mL with enzyme diluent buffer to prepare the final sample solution for LVL-RecAP and/or RecAP enzyme activity.

The endogenous (sample 7) from LVL-RecAP and/or RecAP sample was diluted by taking 1000 µL of the LVL-RecAP and/or RecAP serum sample and diluted to 2.00 mL with enzyme diluent buffer to prepare the final sample solution for LVL-RecAP and/or RecAP enzyme activity.

10.8. Execution, Results and Discussion 10.8.1 Equipment and Settings

The following method and settings were used:

Spectrophotometer: Thermo Fisher Evolution 300 UV/VIS with single cell Peltier heater set at 25° C. (AN-18-3) or 37° C. (AN-18-4) with magnetic stirrer Wavelength: 405 nm Measurement: For 3 minutes, each 15 seconds a measurement. The first minute was not taken into account for the calculations.

Cuvette type: Glass

The following solutions were pipetted into a glass cuvette. The temperature of the solutions was 25° C.±0.5° C. for AN-18-3 or 37° C.±0.5° C. for AN-18-4.

| Reagent | Sample solution | Blank |
|---|---|---|
| Working substrate | 1450 µL | 1450 µL |
| Enzyme diluent | | 50.0 µL |
| Sample | 50.0 µL | |
| Total volume | 1500 µL | 1500 µL |

First the working substrate and the enzyme diluent were mixed before the sample was added. The solution was mixed and the cuvette was placed immediately in the spectrophotometer and the increase in absorbance was measured from 1 to 3 minutes in steps of 15 seconds to obtain at least 9 data points. At the 3 minute (last) data point the Optical density was ≤1.5. Furthermore linearity was acceptable; the correlation coefficient (r) for each replicate should be ≥0.990. All sample results with a correlation coefficient (r) ≥0.990 were taken into account for the evaluation, sample results with a correlation coefficient (r)<0.990 were reported for information only. The enzyme activity was performed in duplicate mode, one test of each dilution.

10.8.2 LVL-RecAP and RecAP Enzyme Activity

Although in the Study Plan was described that the difference for the two individual results (enzyme activity) should be ≤5.0% to accept the two individual dilution results, all results with a correlation coefficient (r) for each measurement ≥0.990 were used for evaluation. This because the enzyme activity method was validated for LVL-RecAP drug product samples at 25° C.±0.5° C. and not for other Alkaline Phosphatase origin and/or other conditions.

FIG. 20 shows the activity/µg protein at 25° C. and at 37° C. for RecAP and LVL-RecAP. Values represent mean Δactivity between 25° C. and 37° C. for a given protein concentration.

The invention claimed is:

1. A protein having phosphatase activity, wherein said protein comprises an amino acid sequence of at least 200 consecutive amino acids having at least 90% sequence identity with SEQ ID NO: 5, an amino acid sequence of at least 50 consecutive amino acids having at least 90% sequence identity with SEQ ID NO: 6, and an amino acid sequence of at least 40 consecutive amino acids having at least 90% sequence identity with SEQ ID NO: 7, wherein the full length protein comprises an amino acid sequence having at least 95% sequence identity with the full length amino acid sequence of SEQ ID NO: 1, with the proviso that the amino acid at position 279 is leucine (L), the amino acid at position 328 is valine (V) and the amino acid at position 478 is leucine (L).

2. The protein of claim 1 which comprises an amino acid sequence having at least 98% sequence identity to the amino acid sequence of SEQ ID NO: 1, with the proviso that the amino acid at position 279 is leucine (L), the amino acid at position 328 is valine (V) and the amino acid at position 478 is leucine (L).

3. The protein of claim 1, wherein said protein comprises an amino acid sequence of 300-365 consecutive amino acids having at least 95% sequence identity with SEQ ID NO: 5, an amino acid sequence of 60-65 consecutive amino acids having at least 95% sequence identity with SEQ ID NO: 6, and an amino acid sequence of 50-54 consecutive amino acids having at least 95% sequence identity with SEQ ID NO: 7, wherein the full length protein comprises an amino acid sequence having at least 95% sequence identity with the full length amino acid sequence of SEQ ID NO: 1, with the proviso that the amino acid at position 279 is leucine (L), the amino acid at position 328 is valine (V) and the amino acid at position 478 is leucine (L).

4. The protein of claim 1, wherein said protein comprises an amino acid sequence of 350-365 consecutive amino acids having at least 98% sequence identity with SEQ ID NO: 5, an amino acid sequence of 62-65 consecutive amino acids having at least 98% sequence identity with SEQ ID NO: 6, and an amino acid sequence of 52-54 consecutive amino acids having at least 98% sequence identity with SEQ ID NO: 7, wherein the full length protein comprises an amino acid sequence having at least 98% sequence identity with the full length amino acid sequence of SEQ ID NO: 1, with the proviso that the amino acid at position 279 is leucine (L), the amino acid at position 328 is valine (V) and the amino acid at position 478 is leucine (L).

5. A polynucleotide comprising a nucleic acid sequence encoding the protein according to claim 1.

6. A vector comprising the polynucleotide according to claim 5.

7. The vector of claim 6 which is a cloning or expression vector.

8. A host cell comprising a vector according to claim 6.

9. The host cell according to claim 8, wherein said host cell is a CHO cell.

10. A method for producing the protein of claim 1, comprising culturing the host cell of claim 8 and allowing the host cell to produce said protein.

11. A composition comprising the protein according to claim 1 and a pharmaceutically acceptable carrier, a diluent, or an excipient.

* * * * *

SEQUENCE LISTING

<160> NUMBER OF SEQ ID NOS: 7

Figure 2:
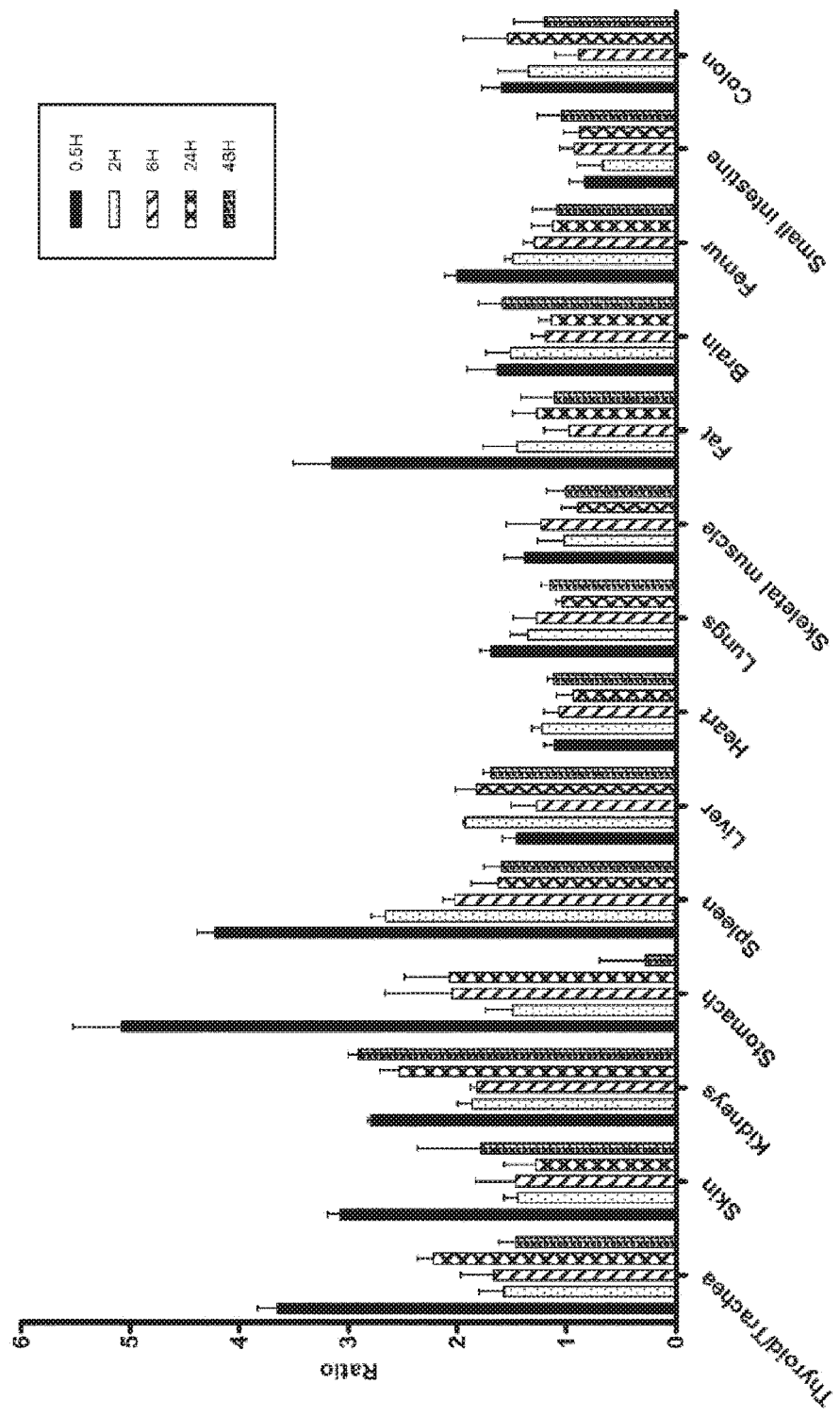
Figure 3:
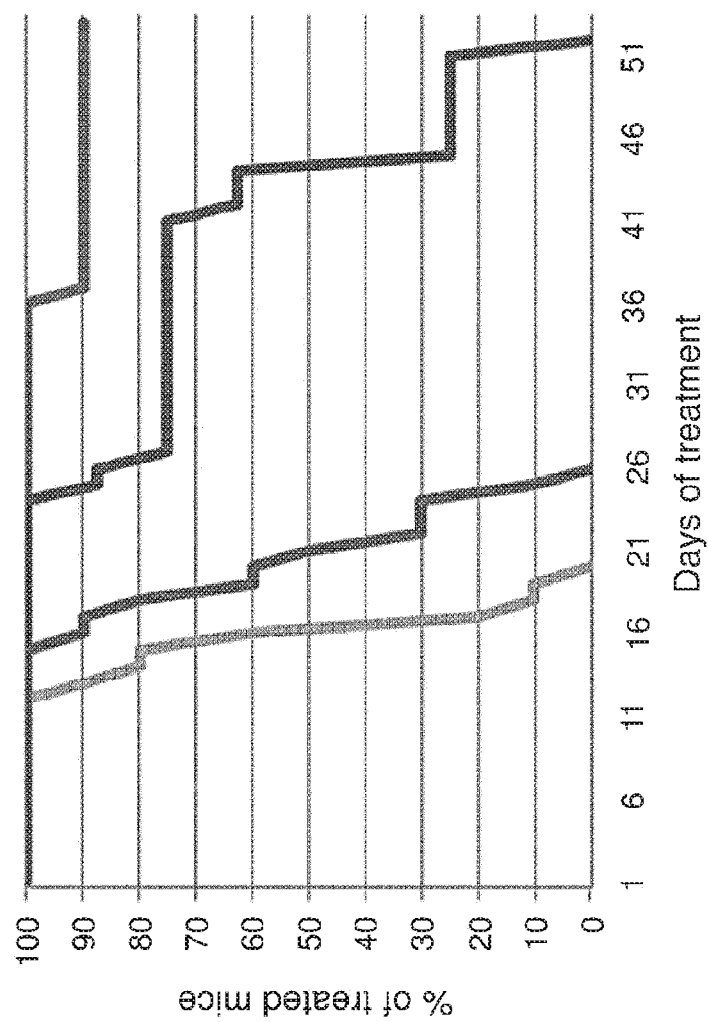
Figure 4:
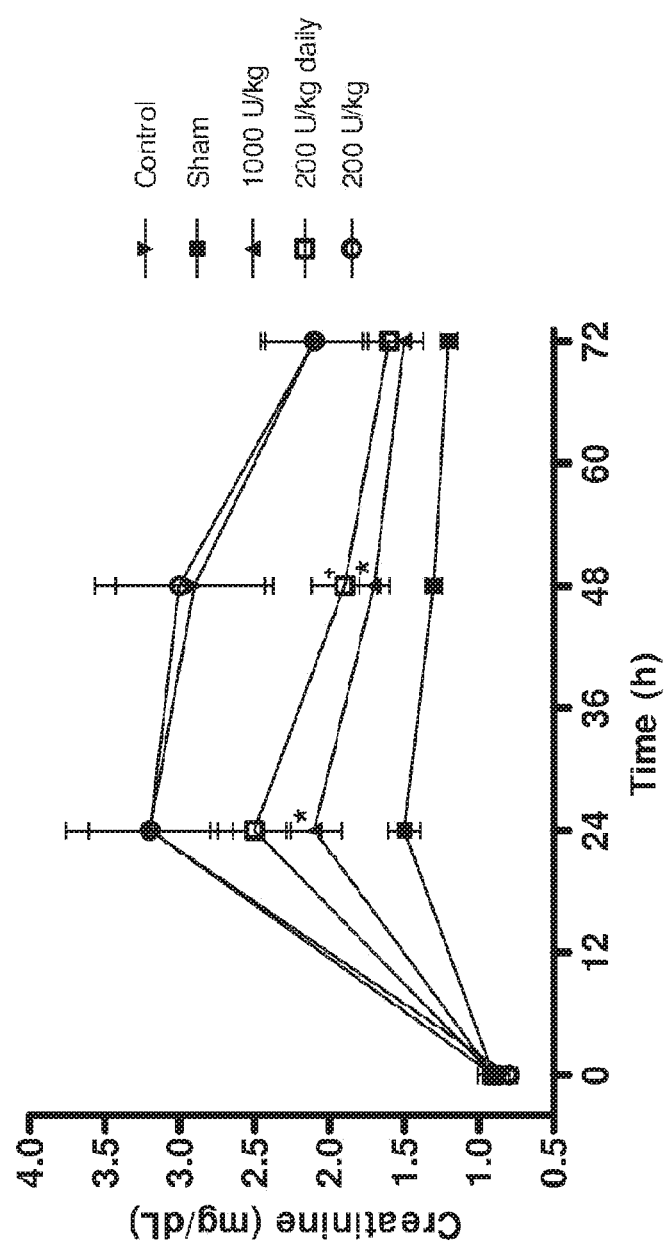
Figure 5:
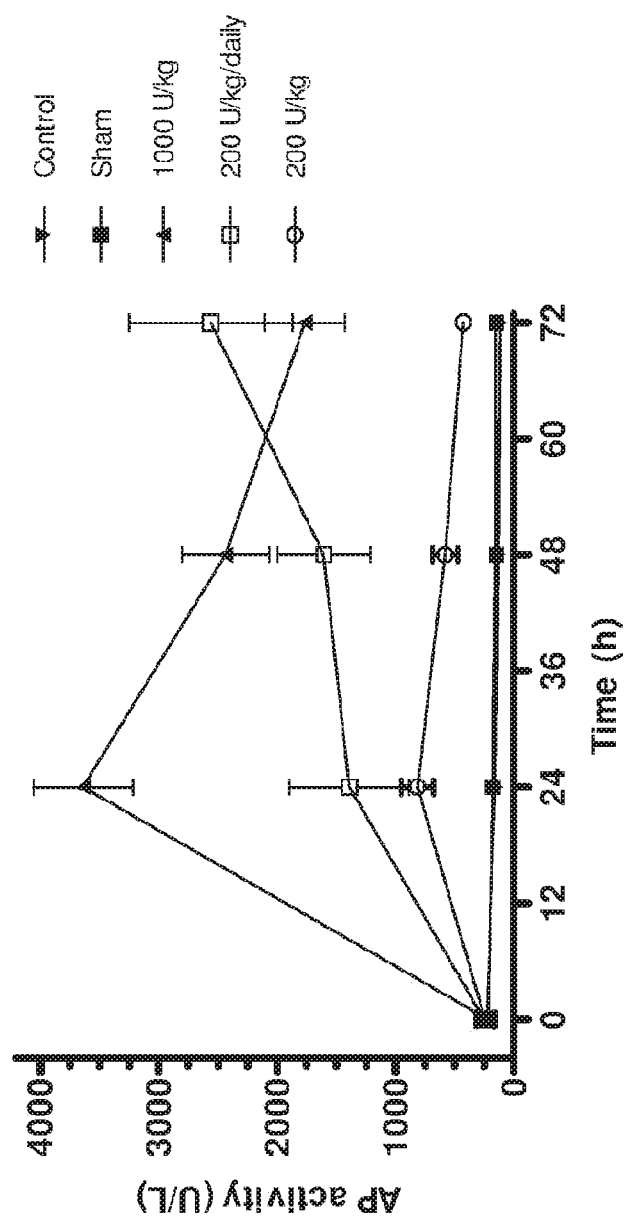
Figure 6A:
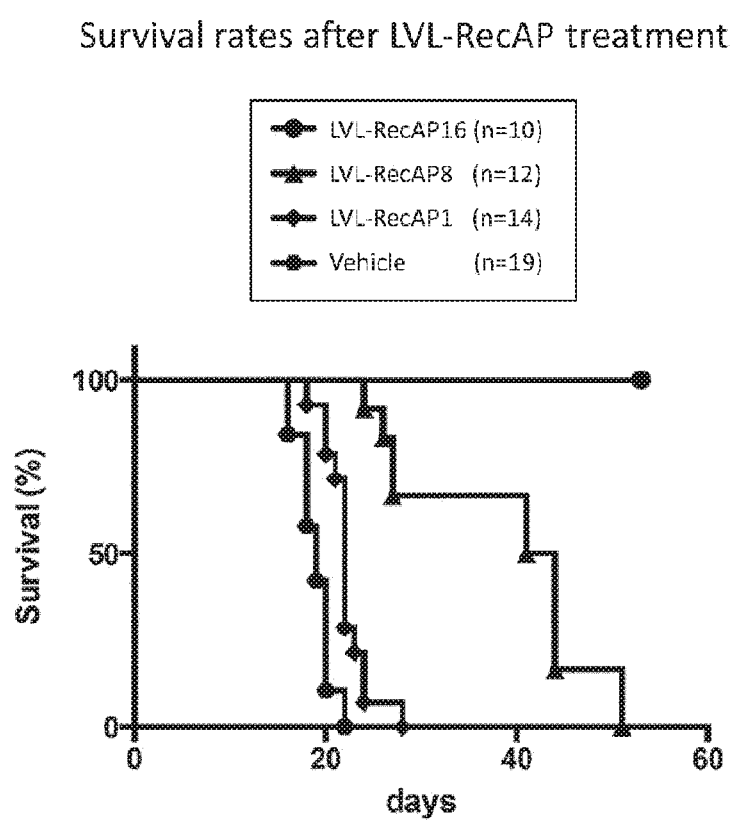
Figure 7A:
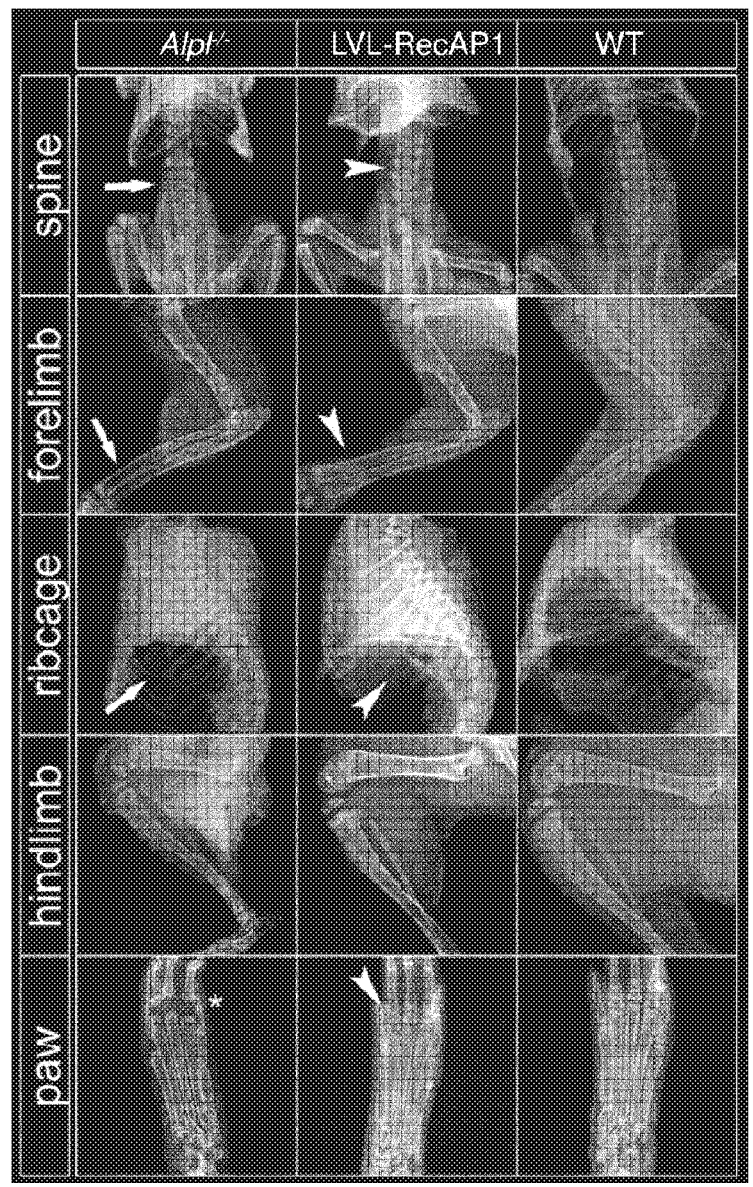
Figure 7B:
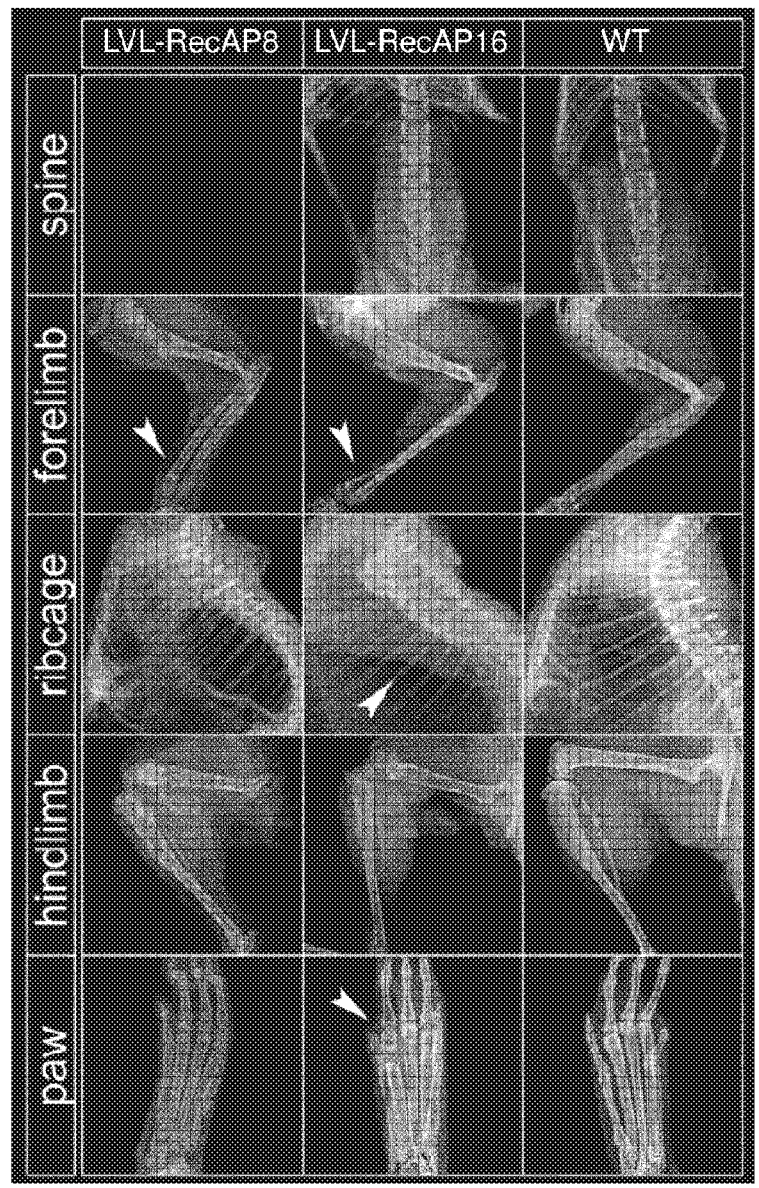
Figure 8A:
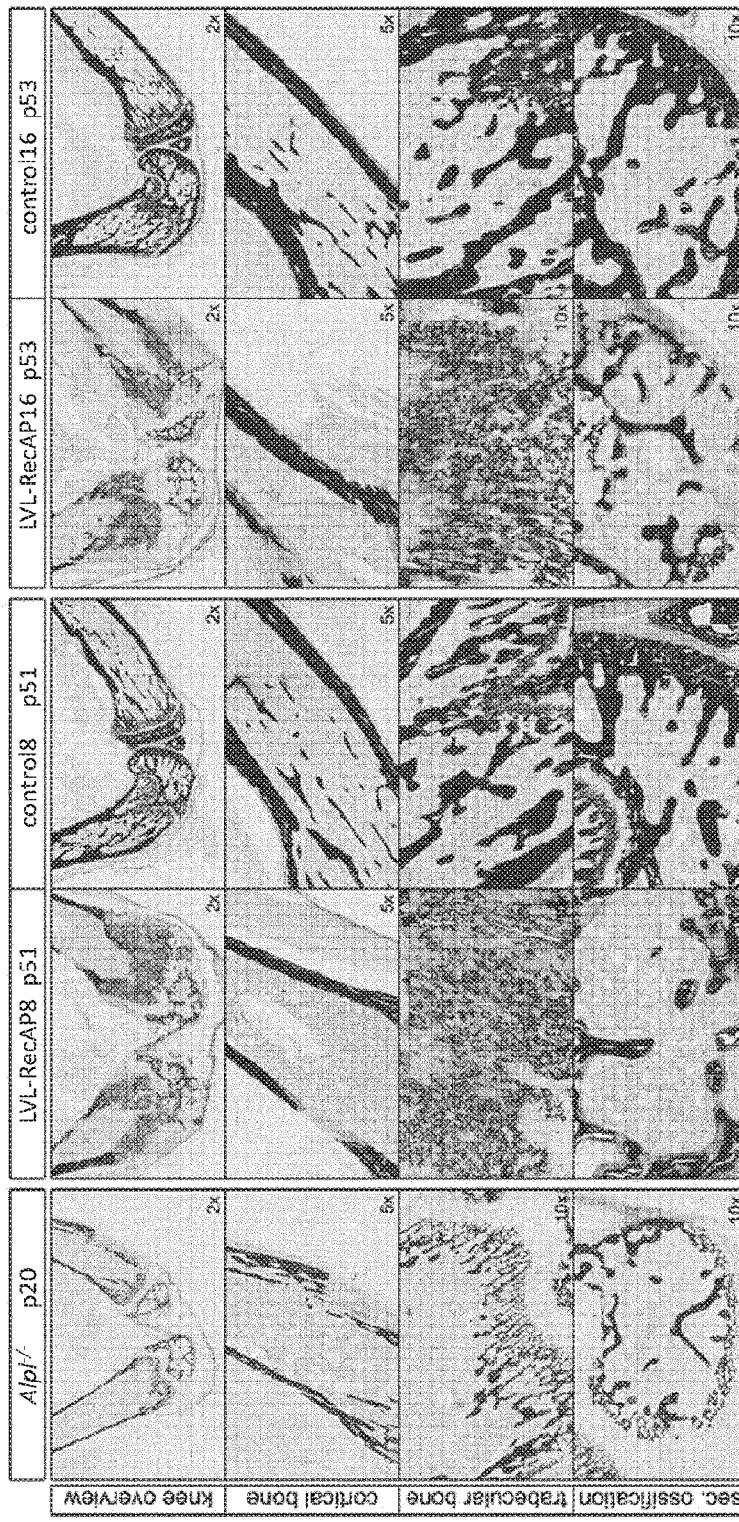
Figure 8B:
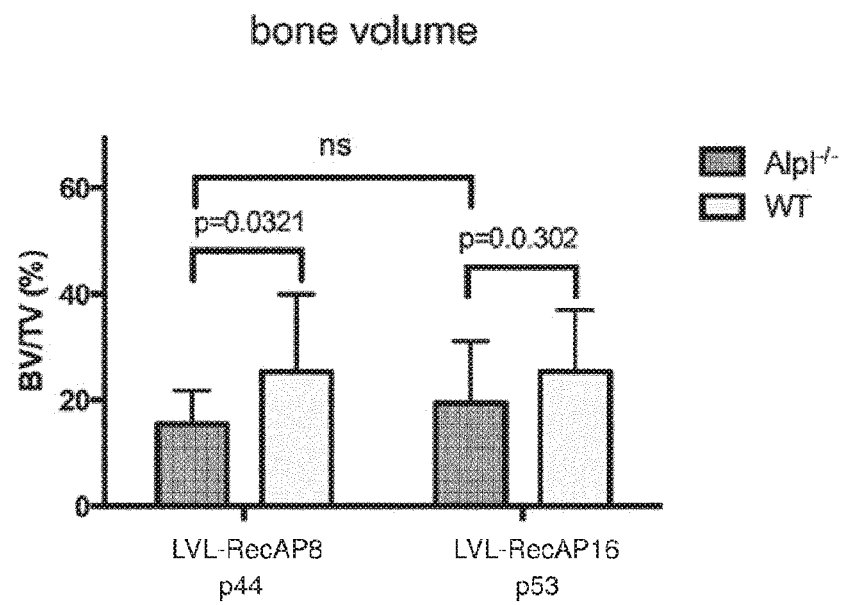
Figure 8C:
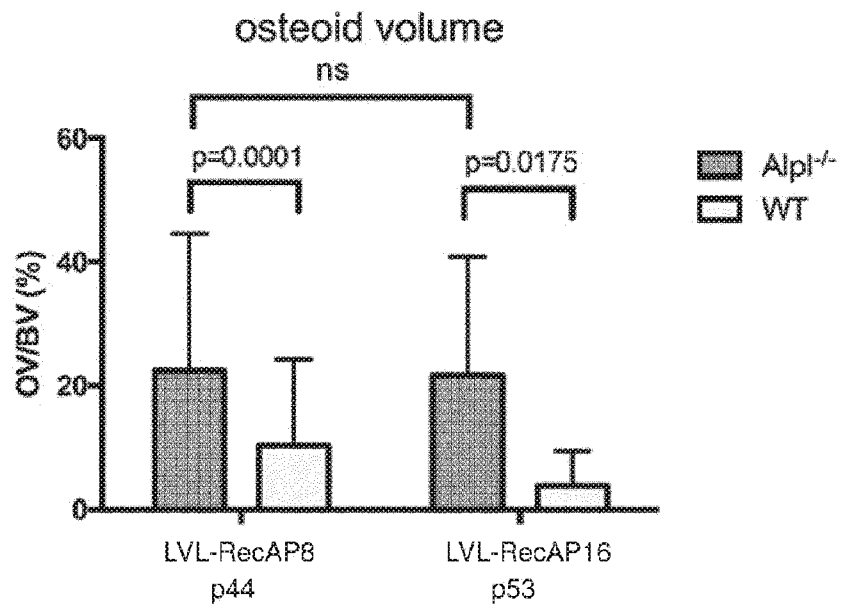
Figure 9A:
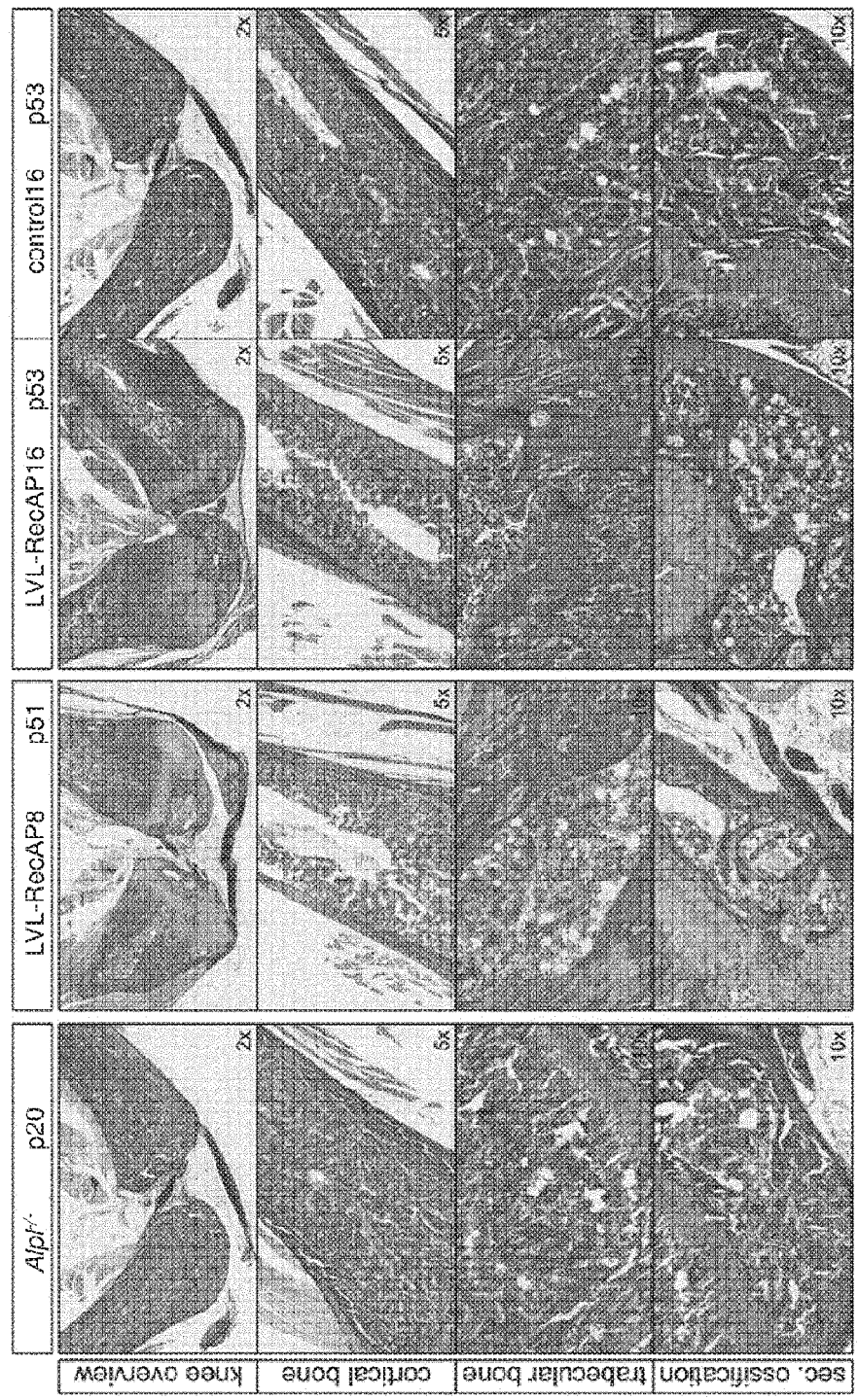
Figure 9B:
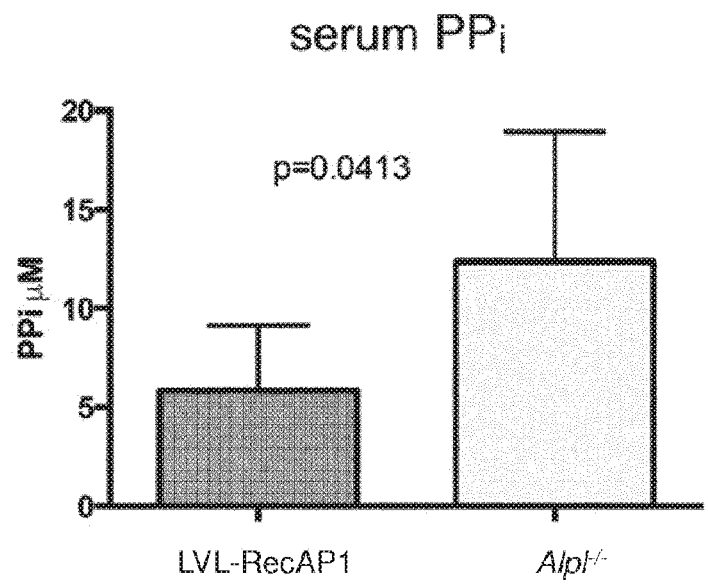
Figure 9C:
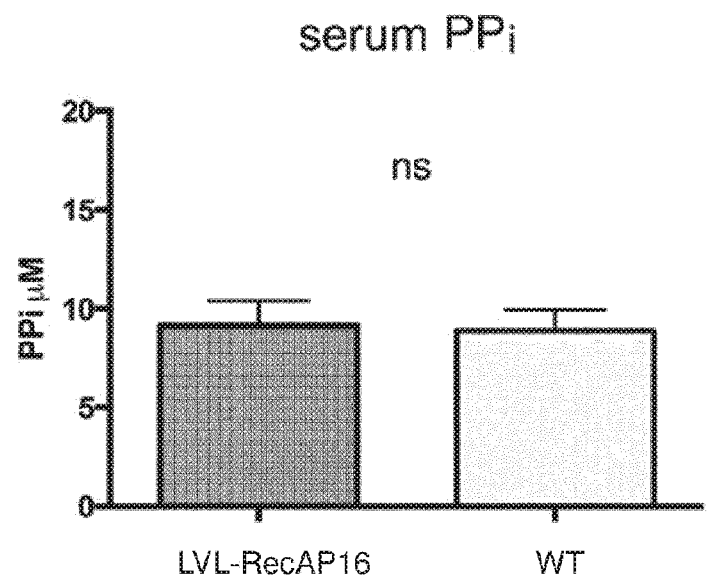
Figures 11J, 11K:
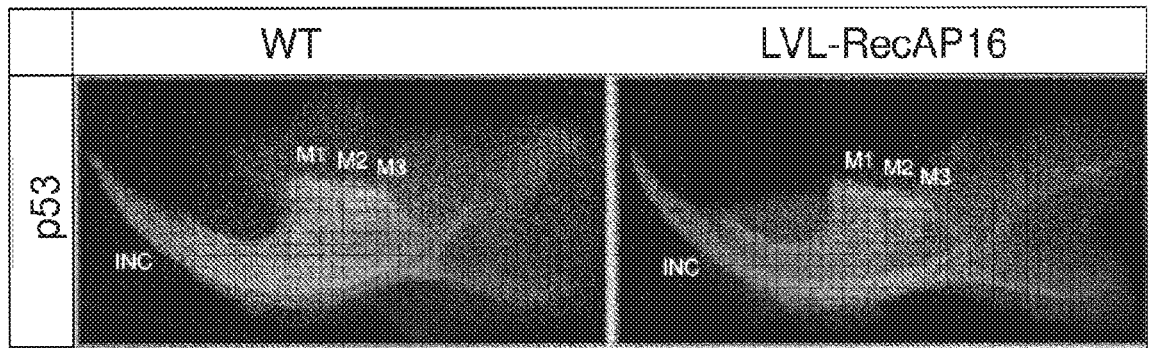
Figures 11L, 11M:
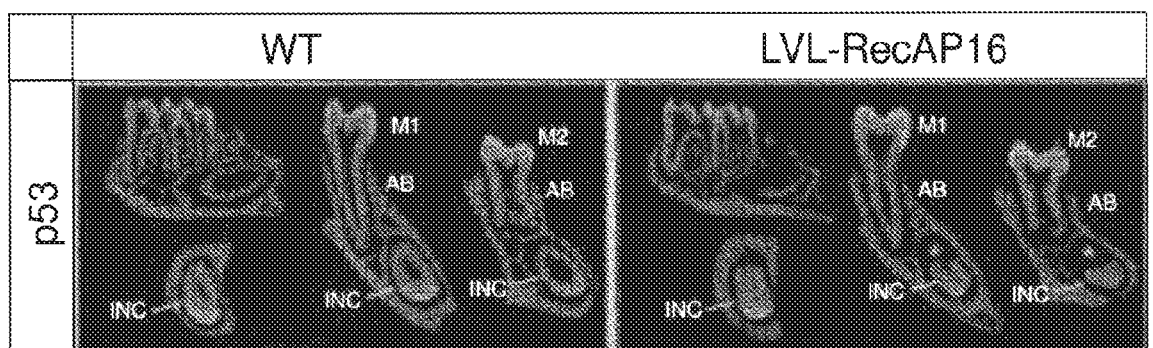
Figures 11N, 11O, 11P, 11Q:
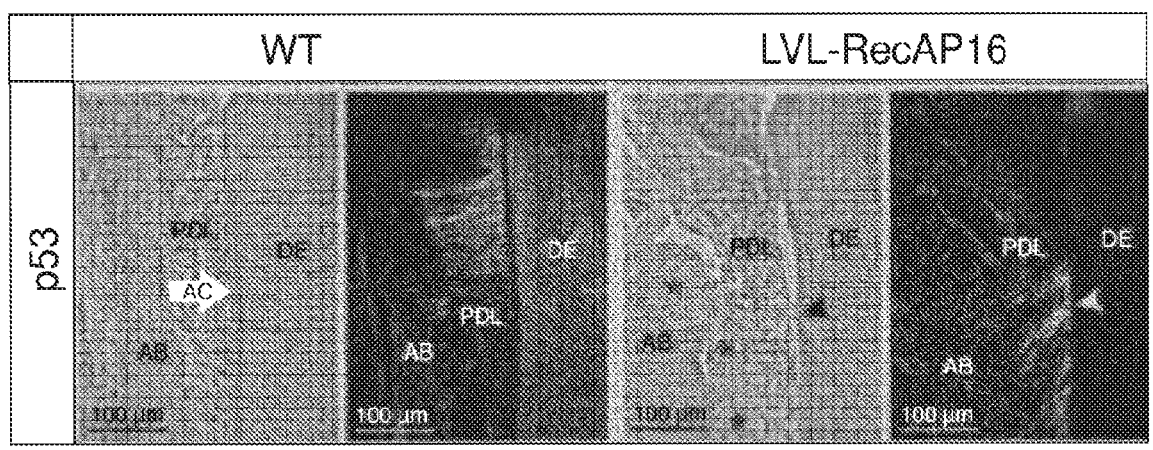
Figure 13A:
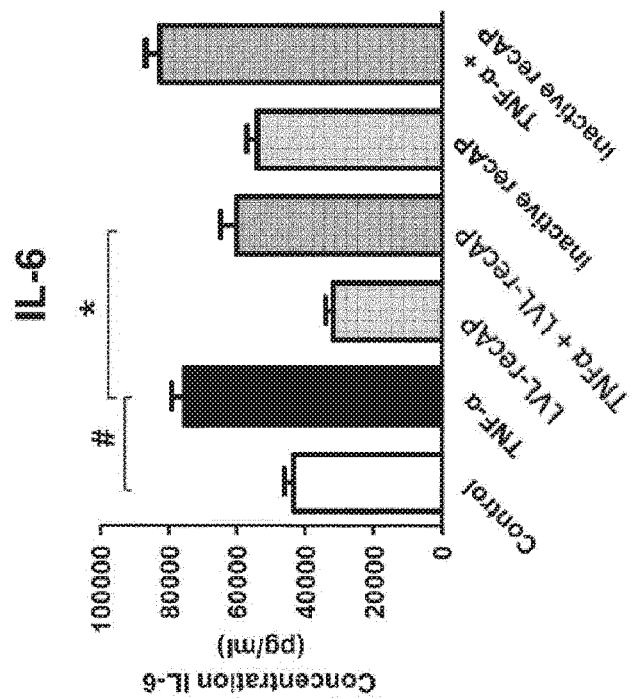
Figure 13B:
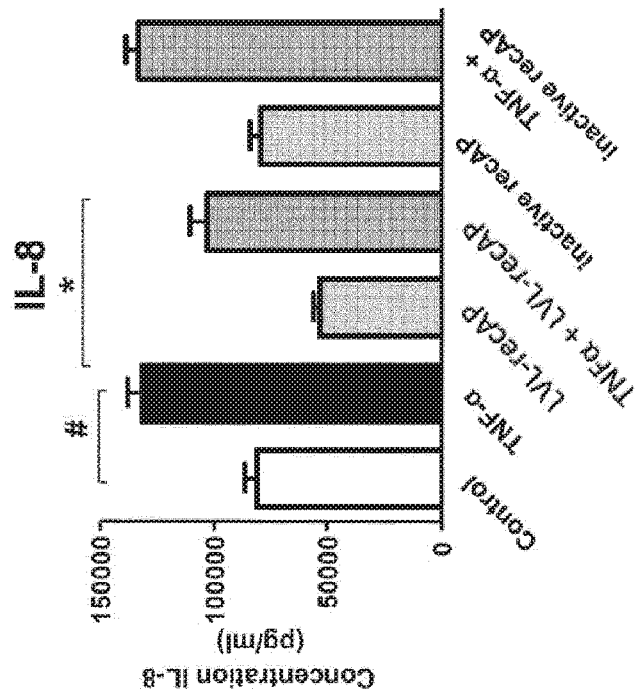
Figures 13C, 13D:
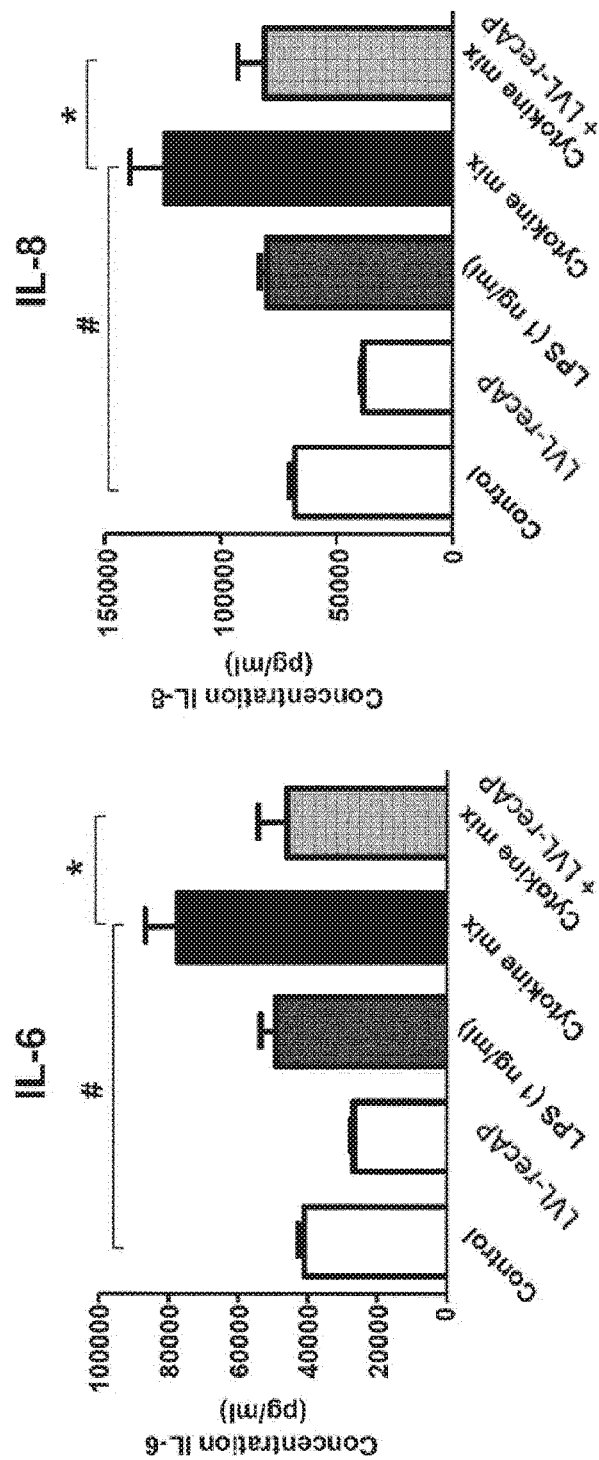
Figure 13F:
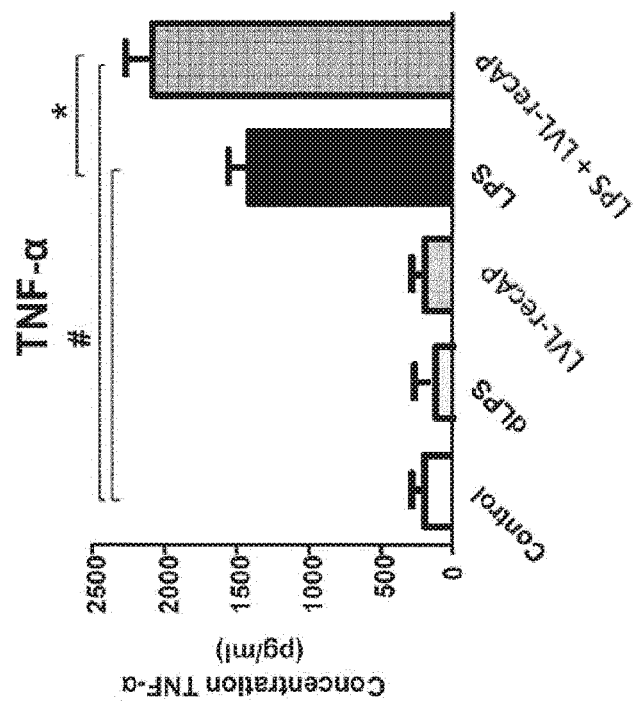
Figure 13E:
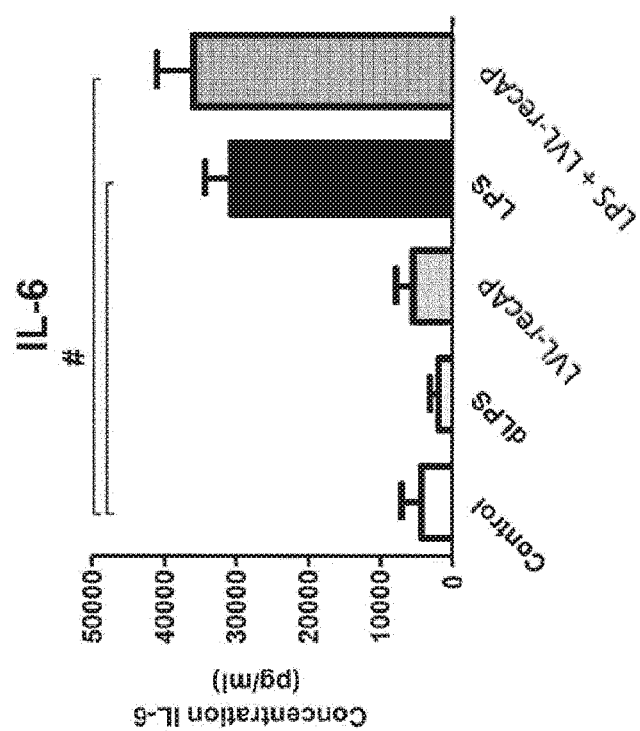
Figure 14:
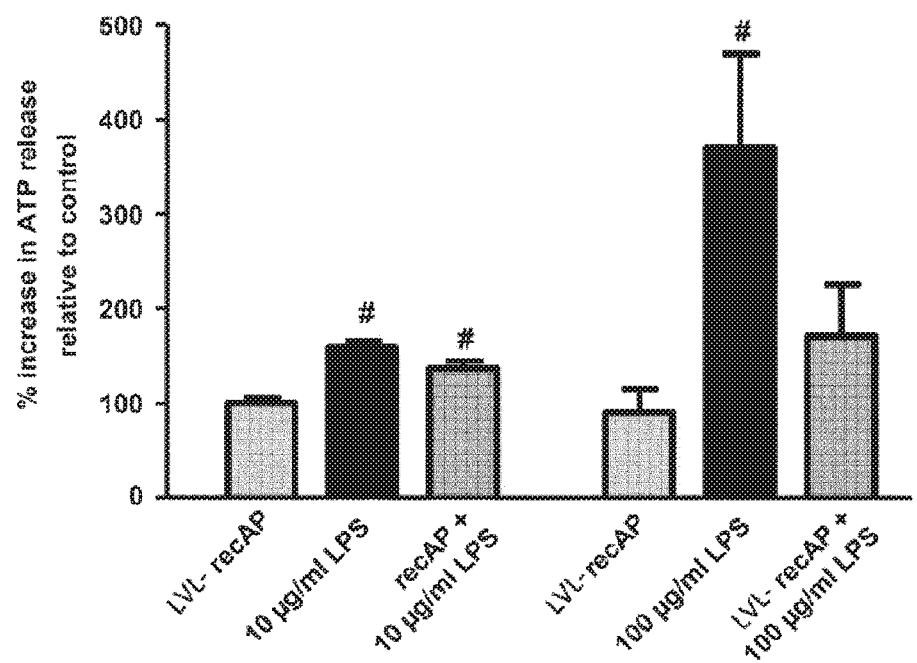
Figure 15A:
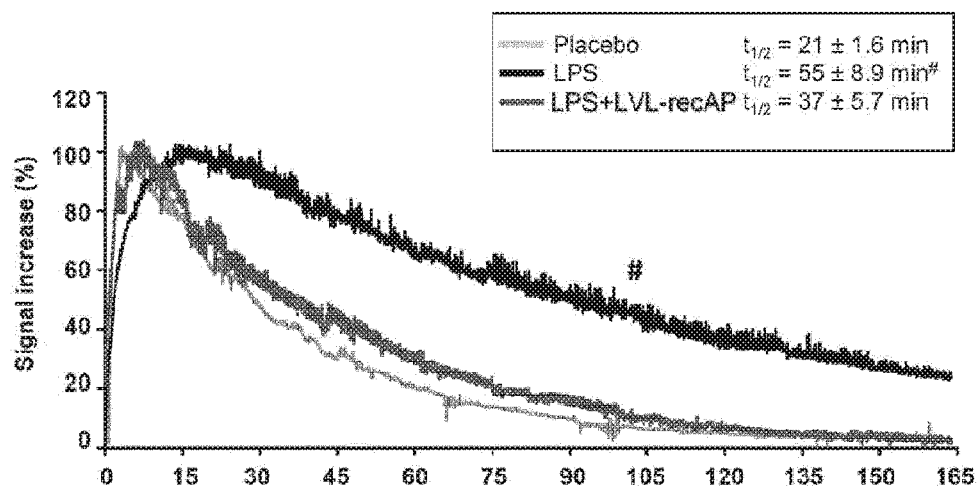
Figure 15B:
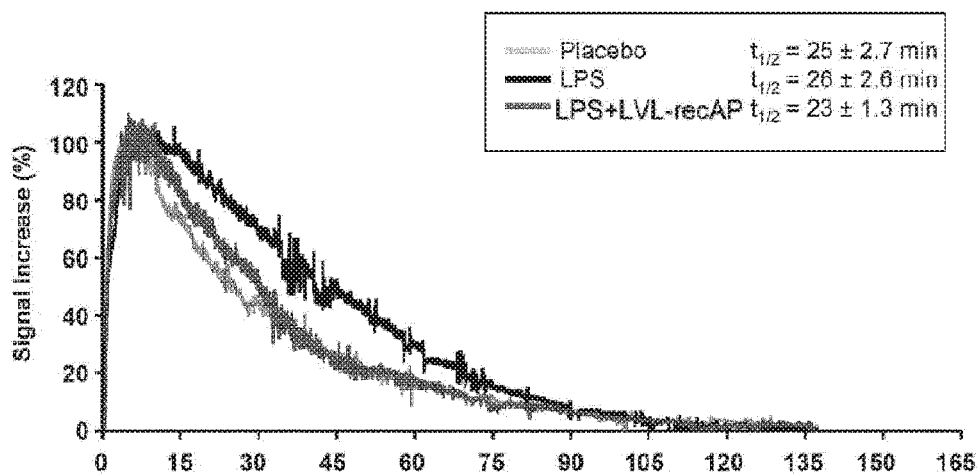
Figure 15C:
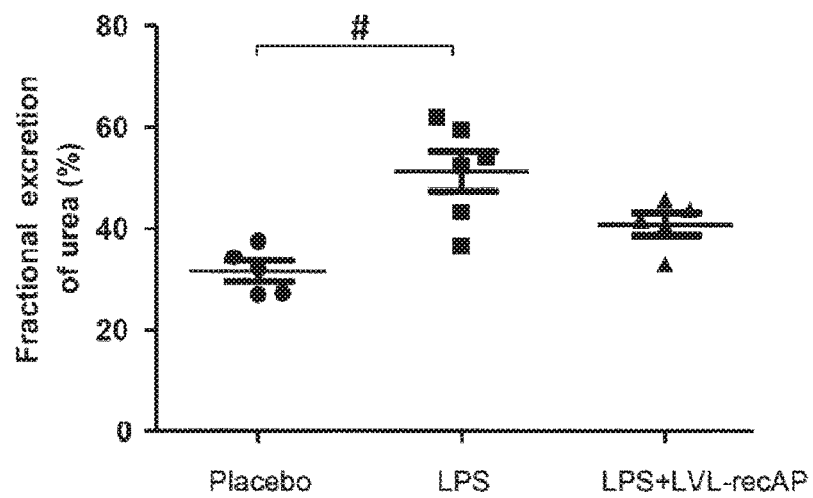
Figure 15D:
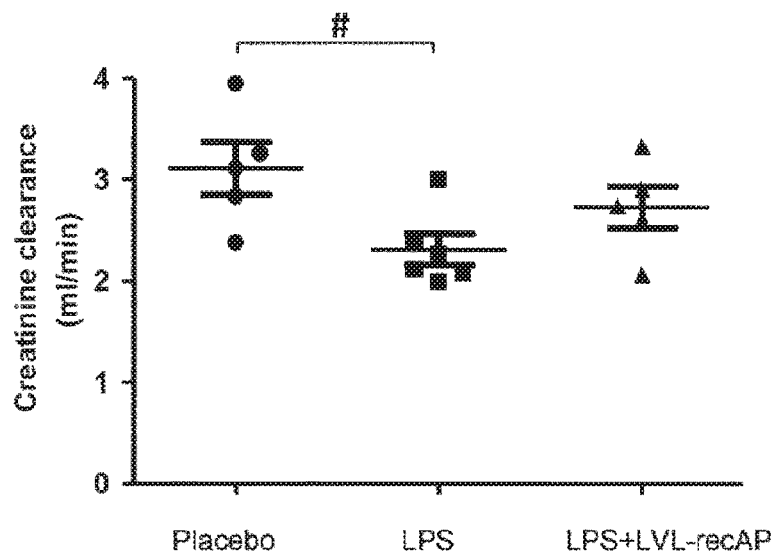
Figure 16A:
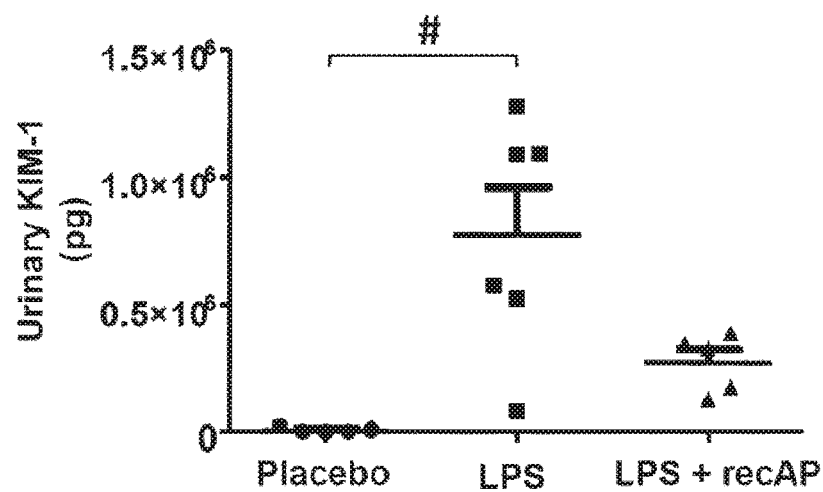
Figure 16B:
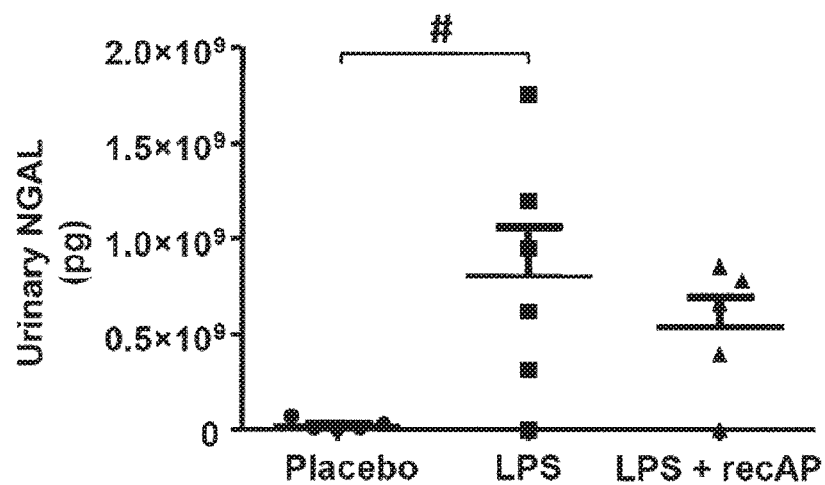
Figure 16C:
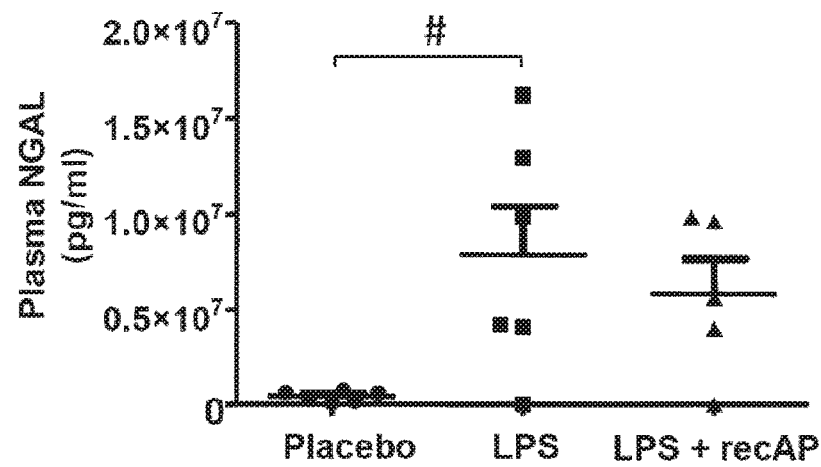
Figure 16D:
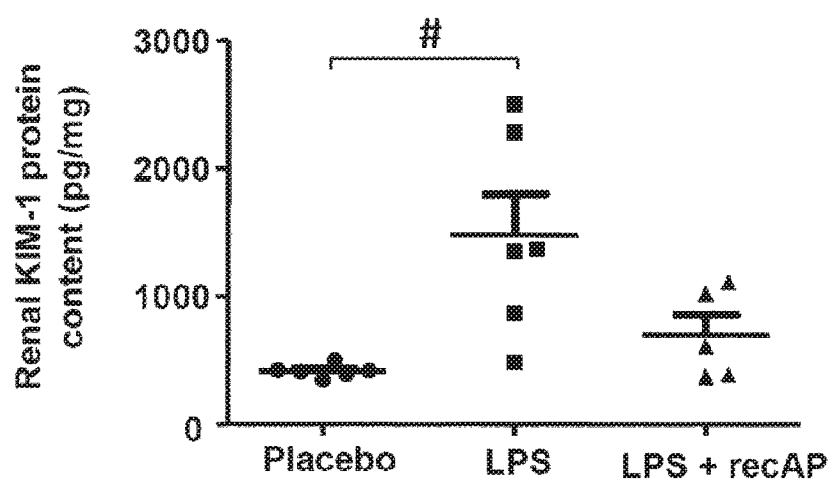
Figure 16E:
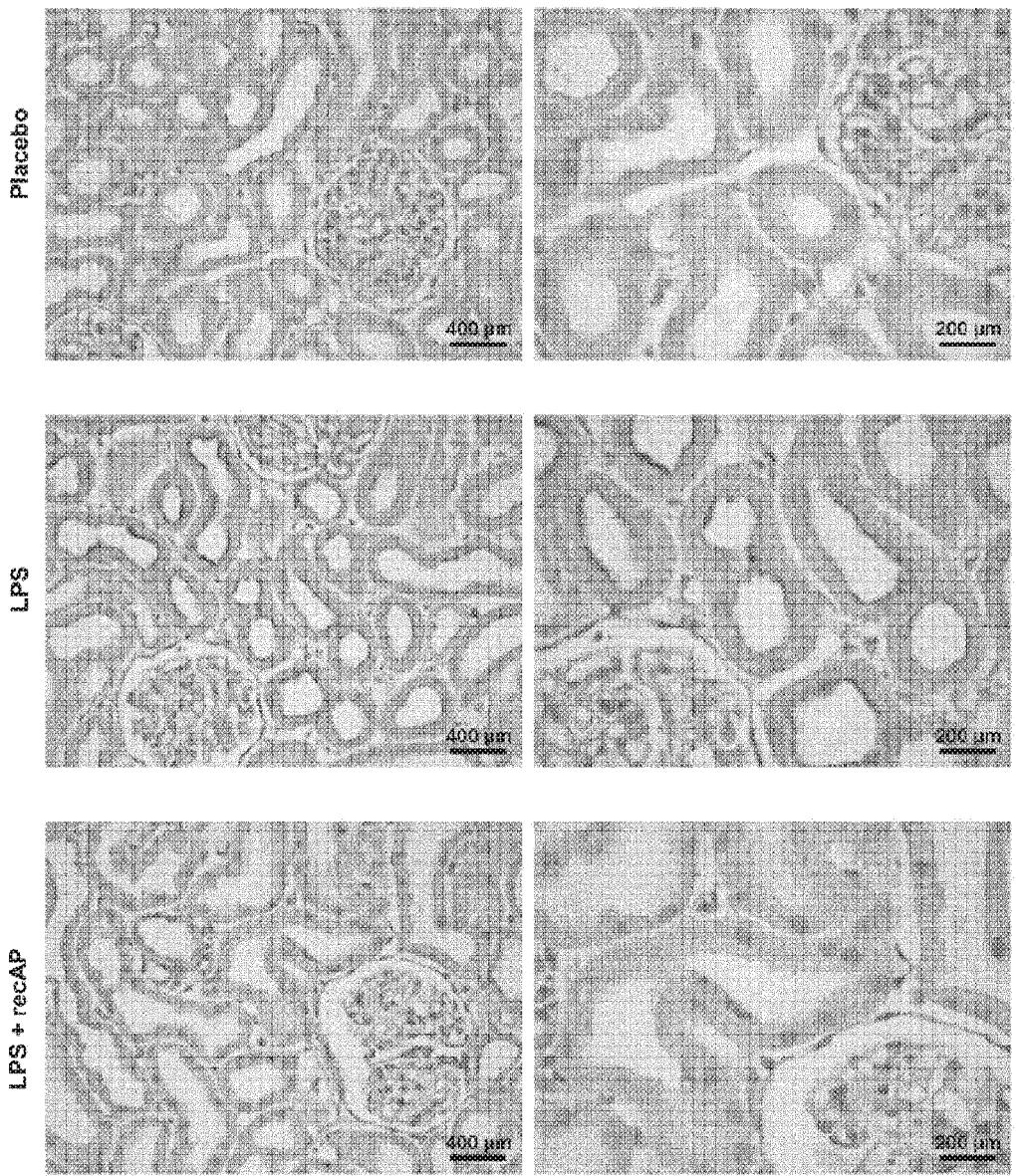
Figure 17A:
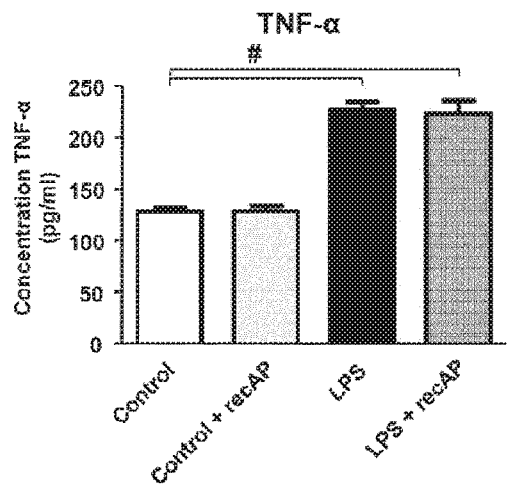
Figure 17B:
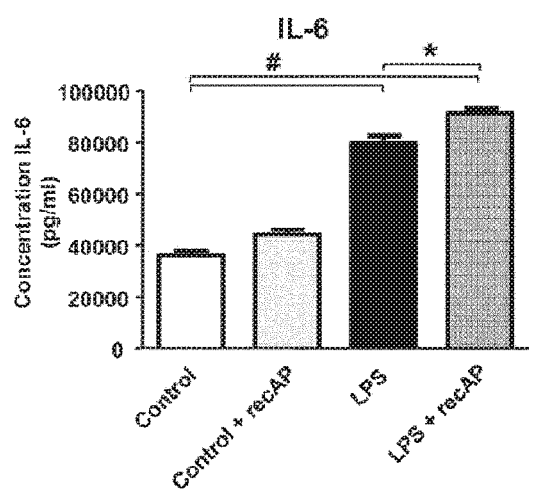
Figure 17C:
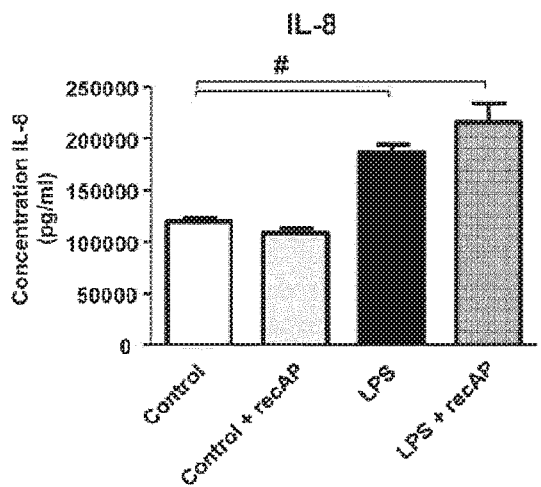
Figure 18:
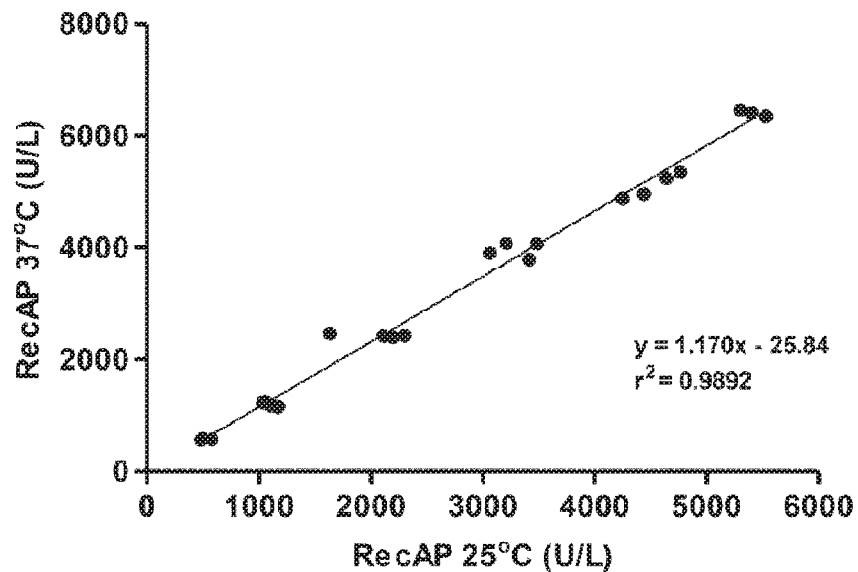
Figure 19:
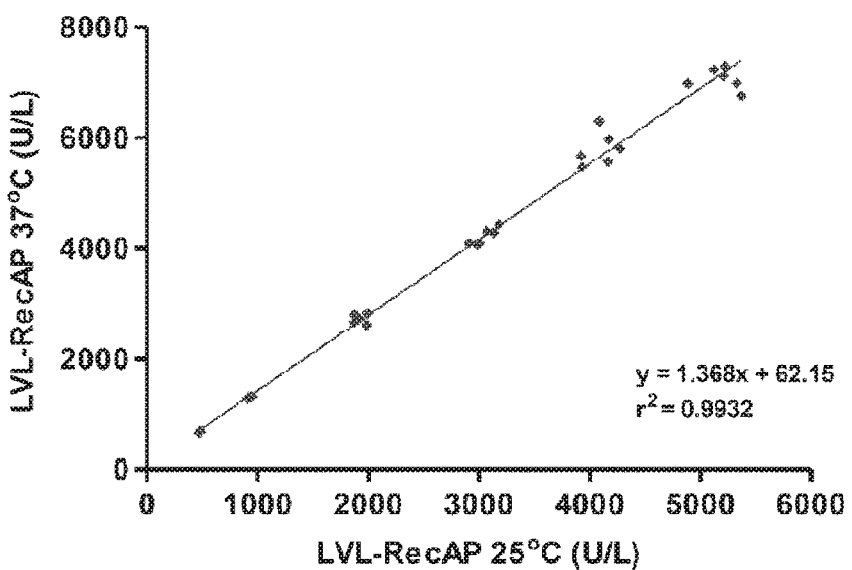
FIG. 19 shows the correlation between enzyme activities of RecAP in human serum at 25° C. and at 37° C.
Figure 20:
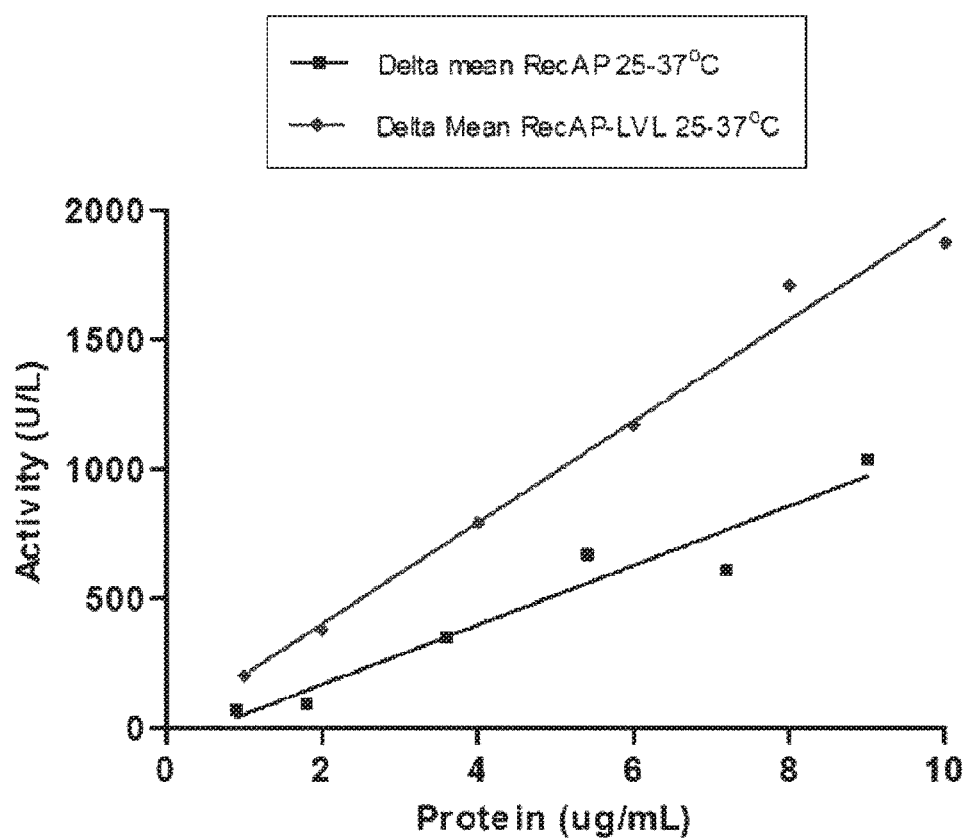
FIG. 20 shows the correlation between enzyme activities of LVL-RecAP in human serum at 25° C. and at 37° C.

<210> SEQ ID NO 1
<211> LENGTH: 484
<212> TYPE: PRT
<213> ORGANISM: Artificial Sequence
<220> FEATURE:
<223> OTHER INFORMATION: Improved RecAP (LVL-RecAP) Sequence

<400> SEQUENCE: 1

```
Val Ile Pro Ala Glu Glu Asn Pro Ala Phe Trp Asn Arg Gln Ala
1               5                   10                  15

Ala Glu Ala Leu Asp Ala Ala Lys Lys Leu Gln Pro Ile Gln Lys Val
                20                  25                  30

Ala Lys Asn Leu Ile Leu Phe Leu Gly Asp Gly Leu Gly Val Pro Thr
            35                  40                  45

Val Thr Ala Thr Arg Ile Leu Lys Gly Gln Lys Asn Gly Lys Leu Gly
        50                  55                  60

Pro Glu Thr Pro Leu Ala Met Asp Arg Phe Pro Tyr Leu Ala Leu Ser
65                  70                  75                  80

Lys Thr Tyr Asn Val Asp Arg Gln Val Pro Asp Ser Ala Ala Thr Ala
                85                  90                  95

Thr Ala Tyr Leu Cys Gly Val Lys Ala Asn Phe Gln Thr Ile Gly Leu
            100                 105                 110

Ser Ala Ala Arg Phe Asn Gln Cys Asn Thr Thr Arg Gly Asn Glu
        115                 120                 125

Val Ile Ser Val Met Asn Arg Ala Lys Gln Ala Gly Lys Ser Val Gly
    130                 135                 140

Val Val Thr Thr Thr Arg Val Gln His Ala Ser Pro Ala Gly Thr Tyr
145                 150                 155                 160

Ala His Thr Val Asn Arg Asn Trp Tyr Ser Asp Ala Asp Met Pro Ala
                165                 170                 175

Ser Ala Arg Gln Glu Gly Cys Gln Asp Ile Ala Thr Gln Leu Ile Ser
            180                 185                 190

Asn Met Asp Ile Asp Val Ile Leu Gly Gly Gly Arg Lys Tyr Met Phe
        195                 200                 205

Pro Met Gly Thr Pro Asp Pro Glu Tyr Pro Ala Asp Ala Ser Gln Asn
    210                 215                 220

Gly Ile Arg Leu Asp Gly Lys Asn Leu Val Gln Glu Trp Leu Ala Lys
225                 230                 235                 240

His Gln Gly Ala Trp Tyr Val Trp Asn Arg Thr Glu Leu Met Gln Ala
                245                 250                 255

Ser Leu Asp Gln Ser Val Thr His Leu Met Gly Leu Phe Glu Pro Gly
            260                 265                 270

Asp Thr Lys Tyr Glu Ile Leu Arg Asp Pro Thr Leu Asp Pro Ser Leu
        275                 280                 285

Met Glu Met Thr Glu Ala Ala Leu Arg Leu Leu Ser Arg Asn Pro Arg
    290                 295                 300

Gly Phe Tyr Leu Phe Val Glu Gly Gly Arg Ile Asp His Gly His His
305                 310                 315                 320

Glu Gly Val Ala Tyr Gln Ala Val Thr Glu Ala Val Met Phe Asp Asp
                325                 330                 335

Ala Ile Glu Arg Ala Gly Gln Leu Thr Ser Glu Glu Asp Thr Leu Thr
            340                 345                 350

Leu Val Thr Ala Asp His Ser His Val Phe Ser Phe Gly Gly Tyr Pro
```

```
                355                 360                 365
Leu Arg Gly Ser Ser Ile Phe Gly Leu Ala Pro Gly Lys Ala Arg Asp
370                 375                 380

Arg Lys Ala Tyr Thr Val Leu Leu Tyr Gly Asn Gly Pro Gly Tyr Val
385                 390                 395                 400

Leu Lys Asp Gly Ala Arg Pro Asp Val Thr Glu Ser Glu Ser Gly Ser
                405                 410                 415

Pro Glu Tyr Arg Gln Gln Ser Ala Val Pro Leu Asp Glu Glu Thr His
                420                 425                 430

Gly Gly Glu Asp Val Ala Val Phe Ala Arg Gly Pro Gln Ala His Leu
            435                 440                 445

Val His Gly Val Gln Glu Gln Ser Phe Val Ala His Val Met Ala Phe
        450                 455                 460

Ala Ala Cys Leu Glu Pro Tyr Thr Ala Cys Asp Leu Ala Leu Pro Ala
465                 470                 475                 480

Cys Thr Thr Asp

<210> SEQ ID NO 2
<211> LENGTH: 484
<212> TYPE: PRT
<213> ORGANISM: Homo sapiens

<400> SEQUENCE: 2

Val Ile Pro Ala Glu Glu Asn Pro Ala Phe Trp Asn Arg Gln Ala
1               5                   10                  15

Ala Glu Ala Leu Asp Ala Ala Lys Lys Leu Gln Pro Ile Gln Lys Val
                20                  25                  30

Ala Lys Asn Leu Ile Leu Phe Leu Gly Asp Gly Leu Gly Val Pro Thr
            35                  40                  45

Val Thr Ala Thr Arg Ile Leu Lys Gly Gln Lys Asn Gly Lys Leu Gly
50                  55                  60

Pro Glu Thr Pro Leu Ala Met Asp Arg Phe Pro Tyr Leu Ala Leu Ser
65                  70                  75                  80

Lys Thr Tyr Asn Val Asp Arg Gln Val Pro Asp Ser Ala Ala Thr Ala
                85                  90                  95

Thr Ala Tyr Leu Cys Gly Val Lys Ala Asn Phe Gln Thr Ile Gly Leu
            100                 105                 110

Ser Ala Ala Ala Arg Phe Asn Gln Cys Asn Thr Thr Arg Gly Asn Glu
        115                 120                 125

Val Ile Ser Val Met Asn Arg Ala Lys Gln Ala Gly Lys Ser Val Gly
130                 135                 140

Val Val Thr Thr Thr Arg Val Gln His Ala Ser Pro Ala Gly Thr Tyr
145                 150                 155                 160

Ala His Thr Val Asn Arg Asn Trp Tyr Ser Asp Ala Asp Met Pro Ala
                165                 170                 175

Ser Ala Arg Gln Glu Gly Cys Gln Asp Ile Ala Thr Gln Leu Ile Ser
            180                 185                 190

Asn Met Asp Ile Asp Val Ile Leu Gly Gly Gly Arg Lys Tyr Met Phe
        195                 200                 205

Pro Met Gly Thr Pro Asp Pro Glu Tyr Pro Ala Asp Ala Ser Gln Asn
210                 215                 220

Gly Ile Arg Leu Asp Gly Lys Asn Leu Val Gln Glu Trp Leu Ala Lys
225                 230                 235                 240

His Gln Gly Ala Trp Tyr Val Trp Asn Arg Thr Glu Leu Met Gln Ala
```

```
            245                 250                 255
Ser Leu Asp Gln Ser Val Thr His Leu Met Gly Leu Phe Glu Pro Gly
        260                 265                 270

Asp Thr Lys Tyr Glu Ile His Arg Asp Pro Thr Leu Asp Pro Ser Leu
    275                 280                 285

Met Glu Met Thr Glu Ala Ala Leu Arg Leu Leu Ser Arg Asn Pro Arg
290                 295                 300

Gly Phe Tyr Leu Phe Val Glu Gly Arg Ile Asp His Gly His His
305                 310                 315                 320

Glu Gly Val Ala Tyr Gln Ala Leu Thr Glu Ala Val Met Phe Asp Asp
                325                 330                 335

Ala Ile Glu Arg Ala Gly Gln Leu Thr Ser Glu Asp Thr Leu Thr
            340                 345                 350

Leu Val Thr Ala Asp His Ser His Val Phe Ser Phe Gly Gly Tyr Thr
        355                 360                 365

Leu Arg Gly Ser Ser Ile Phe Gly Leu Ala Pro Ser Lys Ala Gln Asp
    370                 375                 380

Ser Lys Ala Tyr Thr Ser Ile Leu Tyr Gly Asn Gly Pro Gly Tyr Val
385                 390                 395                 400

Phe Asn Ser Gly Val Arg Pro Asp Val Asn Glu Ser Glu Ser Gly Ser
                405                 410                 415

Pro Asp Tyr Gln Gln Gln Ala Ala Val Pro Leu Ser Ser Glu Thr His
            420                 425                 430

Gly Gly Glu Asp Val Ala Val Phe Ala Arg Gly Pro Gln Ala His Leu
        435                 440                 445

Val His Gly Val Gln Glu Gln Ser Phe Val Ala His Val Met Ala Phe
    450                 455                 460

Ala Ala Cys Leu Glu Pro Tyr Thr Ala Cys Asp Leu Ala Pro Pro Ala
465                 470                 475                 480

Cys Thr Thr Asp

<210> SEQ ID NO 3
<211> LENGTH: 484
<212> TYPE: PRT
<213> ORGANISM: Homo sapiens

<400> SEQUENCE: 3

Ile Ile Pro Val Glu Glu Asn Pro Asp Phe Trp Asn Arg Glu Ala
1               5                   10                  15

Ala Glu Ala Leu Gly Ala Ala Lys Lys Leu Gln Pro Ala Gln Thr Ala
            20                  25                  30

Ala Lys Asn Leu Ile Ile Phe Leu Gly Asp Gly Met Gly Val Ser Thr
        35                  40                  45

Val Thr Ala Ala Arg Ile Leu Lys Gly Gln Lys Lys Asp Lys Leu Gly
    50                  55                  60

Pro Glu Ile Pro Leu Ala Met Asp Arg Phe Pro Tyr Val Ala Leu Ser
65                  70                  75                  80

Lys Thr Tyr Asn Val Asp Lys His Val Pro Asp Ser Gly Ala Thr Ala
                85                  90                  95

Thr Ala Tyr Leu Cys Gly Val Lys Gly Asn Phe Gln Thr Ile Gly Leu
            100                 105                 110

Ser Ala Ala Ala Arg Phe Asn Gln Cys Asn Thr Thr Arg Gly Asn Glu
        115                 120                 125

Val Ile Ser Val Met Asn Arg Ala Lys Lys Ala Gly Lys Ser Val Gly
```

```
            130                 135                 140
Val Val Thr Thr Thr Arg Val Gln His Ala Ser Pro Ala Gly Thr Tyr
145                 150                 155                 160

Ala His Thr Val Asn Arg Asn Trp Tyr Ser Asp Ala Asp Val Pro Ala
                165                 170                 175

Ser Ala Arg Gln Glu Gly Cys Gln Asp Ile Ala Thr Gln Leu Ile Ser
                180                 185                 190

Asn Met Asp Ile Asp Val Ile Leu Gly Gly Gly Arg Lys Tyr Met Phe
            195                 200                 205

Arg Met Gly Thr Pro Asp Pro Glu Tyr Pro Asp Asp Tyr Ser Gln Gly
        210                 215                 220

Gly Thr Arg Leu Asp Gly Lys Asn Leu Val Gln Glu Trp Leu Ala Lys
225                 230                 235                 240

Arg Gln Gly Ala Arg Tyr Val Trp Asn Arg Thr Glu Leu Met Gln Ala
                245                 250                 255

Ser Leu Asp Pro Ser Val Thr His Leu Met Gly Leu Phe Glu Pro Gly
                260                 265                 270

Asp Met Lys Tyr Glu Ile His Arg Asp Ser Thr Leu Asp Pro Ser Leu
            275                 280                 285

Met Glu Met Thr Glu Ala Ala Leu Arg Leu Leu Ser Arg Asn Pro Arg
        290                 295                 300

Gly Phe Phe Leu Phe Val Glu Gly Gly Arg Ile Asp His Gly His His
305                 310                 315                 320

Glu Ser Arg Ala Tyr Arg Ala Leu Thr Glu Thr Ile Met Phe Asp Asp
                325                 330                 335

Ala Ile Glu Arg Ala Gly Gln Leu Thr Ser Glu Glu Asp Thr Leu Ser
            340                 345                 350

Leu Val Thr Ala Asp His Ser His Val Phe Ser Phe Gly Gly Tyr Pro
        355                 360                 365

Leu Arg Gly Ser Ser Ile Phe Gly Leu Ala Pro Gly Lys Ala Arg Asp
370                 375                 380

Arg Lys Ala Tyr Thr Val Leu Leu Tyr Gly Asn Gly Pro Gly Tyr Val
385                 390                 395                 400

Leu Lys Asp Gly Ala Arg Pro Asp Val Thr Glu Ser Glu Ser Gly Ser
                405                 410                 415

Pro Glu Tyr Arg Gln Gln Ser Ala Val Pro Leu Asp Glu Glu Thr His
            420                 425                 430

Ala Gly Glu Asp Val Ala Val Phe Ala Arg Gly Pro Gln Ala His Leu
        435                 440                 445

Val His Gly Val Gln Glu Gln Thr Phe Ile Ala His Val Met Ala Phe
450                 455                 460

Ala Ala Cys Leu Glu Pro Tyr Thr Ala Cys Asp Leu Ala Pro Pro Ala
465                 470                 475                 480

Gly Thr Thr Asp

<210> SEQ ID NO 4
<211> LENGTH: 484
<212> TYPE: PRT
<213> ORGANISM: Artificial Sequence
<220> FEATURE:
<223> OTHER INFORMATION: sALPI-ALPP-CD Sequence

<400> SEQUENCE: 4

Val Ile Pro Ala Glu Glu Glu Asn Pro Ala Phe Trp Asn Arg Gln Ala
1               5                   10                  15
```

```
Ala Glu Ala Leu Asp Ala Ala Lys Lys Leu Gln Pro Ile Gln Lys Val
             20                  25                  30

Ala Lys Asn Leu Ile Leu Phe Leu Gly Asp Gly Leu Gly Val Pro Thr
         35                  40                  45

Val Thr Ala Thr Arg Ile Leu Lys Gly Gln Lys Asn Gly Lys Leu Gly
 50                  55                  60

Pro Glu Thr Pro Leu Ala Met Asp Arg Phe Pro Tyr Leu Ala Leu Ser
 65                  70                  75                  80

Lys Thr Tyr Asn Val Asp Arg Gln Val Pro Asp Ser Ala Ala Thr Ala
                 85                  90                  95

Thr Ala Tyr Leu Cys Gly Val Lys Ala Asn Phe Gln Thr Ile Gly Leu
            100                 105                 110

Ser Ala Ala Arg Phe Asn Gln Cys Asn Thr Thr Arg Gly Asn Glu
            115                 120                 125

Val Ile Ser Val Met Asn Arg Ala Lys Gln Ala Gly Lys Ser Val Gly
130                 135                 140

Val Val Thr Thr Thr Arg Val Gln His Ala Ser Pro Ala Gly Thr Tyr
145                 150                 155                 160

Ala His Thr Val Asn Arg Asn Trp Tyr Ser Asp Ala Asp Met Pro Ala
                165                 170                 175

Ser Ala Arg Gln Glu Gly Cys Gln Asp Ile Ala Thr Gln Leu Ile Ser
            180                 185                 190

Asn Met Asp Ile Asp Val Ile Leu Gly Gly Gly Arg Lys Tyr Met Phe
            195                 200                 205

Pro Met Gly Thr Pro Asp Pro Glu Tyr Pro Ala Asp Ala Ser Gln Asn
            210                 215                 220

Gly Ile Arg Leu Asp Gly Lys Asn Leu Val Gln Glu Trp Leu Ala Lys
225                 230                 235                 240

His Gln Gly Ala Trp Tyr Val Trp Asn Arg Thr Glu Leu Met Gln Ala
                245                 250                 255

Ser Leu Asp Gln Ser Val Thr His Leu Met Gly Leu Phe Glu Pro Gly
            260                 265                 270

Asp Thr Lys Tyr Glu Ile His Arg Asp Pro Thr Leu Asp Pro Ser Leu
            275                 280                 285

Met Glu Met Thr Glu Ala Ala Leu Arg Leu Leu Ser Arg Asn Pro Arg
            290                 295                 300

Gly Phe Tyr Leu Phe Val Glu Gly Gly Arg Ile Asp His Gly His His
305                 310                 315                 320

Glu Gly Val Ala Tyr Gln Ala Leu Thr Glu Ala Val Met Phe Asp Asp
                325                 330                 335

Ala Ile Glu Arg Ala Gly Gln Leu Thr Ser Glu Glu Asp Thr Leu Thr
            340                 345                 350

Leu Val Thr Ala Asp His Ser His Val Phe Ser Phe Gly Gly Tyr Pro
            355                 360                 365

Leu Arg Gly Ser Ser Ile Phe Gly Leu Ala Pro Gly Lys Ala Arg Asp
            370                 375                 380

Arg Lys Ala Tyr Thr Val Leu Leu Tyr Gly Asn Gly Pro Gly Tyr Val
385                 390                 395                 400

Leu Lys Asp Gly Ala Arg Pro Asp Val Thr Glu Ser Glu Ser Gly Ser
                405                 410                 415

Pro Glu Tyr Arg Gln Gln Ser Ala Val Pro Leu Asp Glu Glu Thr His
            420                 425                 430
```

Gly Gly Glu Asp Val Ala Val Phe Ala Arg Gly Pro Gln Ala His Leu
            435                 440                 445

Val His Gly Val Gln Glu Gln Ser Phe Val Ala His Val Met Ala Phe
450                 455                 460

Ala Ala Cys Leu Glu Pro Tyr Thr Ala Cys Asp Leu Ala Pro Pro Ala
465                 470                 475                 480

Cys Thr Thr Asp

<210> SEQ ID NO 5
<211> LENGTH: 365
<212> TYPE: PRT
<213> ORGANISM: Homo sapiens

<400> SEQUENCE: 5

Val Ile Pro Ala Glu Glu Asn Pro Ala Phe Trp Asn Arg Gln Ala
1               5                   10                  15

Ala Glu Ala Leu Asp Ala Ala Lys Lys Leu Gln Pro Ile Gln Lys Val
                20                  25                  30

Ala Lys Asn Leu Ile Leu Phe Leu Gly Asp Gly Leu Gly Val Pro Thr
            35                  40                  45

Val Thr Ala Thr Arg Ile Leu Lys Gly Gln Lys Asn Gly Lys Leu Gly
50                  55                  60

Pro Glu Thr Pro Leu Ala Met Asp Arg Phe Pro Tyr Leu Ala Leu Ser
65                  70                  75                  80

Lys Thr Tyr Asn Val Asp Arg Gln Val Pro Asp Ser Ala Ala Thr Ala
                85                  90                  95

Thr Ala Tyr Leu Cys Gly Val Lys Ala Asn Phe Gln Thr Ile Gly Leu
            100                 105                 110

Ser Ala Ala Ala Arg Phe Asn Gln Cys Asn Thr Thr Arg Gly Asn Glu
            115                 120                 125

Val Ile Ser Val Met Asn Arg Ala Lys Gln Ala Gly Lys Ser Val Gly
130                 135                 140

Val Val Thr Thr Thr Arg Val Gln His Ala Ser Pro Ala Gly Thr Tyr
145                 150                 155                 160

Ala His Thr Val Asn Arg Asn Trp Tyr Ser Asp Ala Asp Met Pro Ala
                165                 170                 175

Ser Ala Arg Gln Glu Gly Cys Gln Asp Ile Ala Thr Gln Leu Ile Ser
            180                 185                 190

Asn Met Asp Ile Asp Val Ile Leu Gly Gly Gly Arg Lys Tyr Met Phe
            195                 200                 205

Pro Met Gly Thr Pro Asp Pro Glu Tyr Pro Ala Asp Ala Ser Gln Asn
        210                 215                 220

Gly Ile Arg Leu Asp Gly Lys Asn Leu Val Gln Glu Trp Leu Ala Lys
225                 230                 235                 240

His Gln Gly Ala Trp Tyr Val Trp Asn Arg Thr Glu Leu Met Gln Ala
                245                 250                 255

Ser Leu Asp Gln Ser Val Thr His Leu Met Gly Leu Phe Glu Pro Gly
            260                 265                 270

Asp Thr Lys Tyr Glu Ile His Arg Asp Pro Thr Leu Asp Pro Ser Leu
        275                 280                 285

Met Glu Met Thr Glu Ala Ala Leu Arg Leu Leu Ser Arg Asn Pro Arg
    290                 295                 300

Gly Phe Tyr Leu Phe Val Glu Gly Gly Arg Ile Asp His Gly His His
305                 310                 315                 320

```
Glu Gly Val Ala Tyr Gln Ala Leu Thr Glu Ala Val Met Phe Asp Asp
                325                 330                 335

Ala Ile Glu Arg Ala Gly Gln Leu Thr Ser Glu Glu Asp Thr Leu Thr
            340                 345                 350

Leu Val Thr Ala Asp His Ser His Val Phe Ser Phe Gly
        355                 360                 365

<210> SEQ ID NO 6
<211> LENGTH: 65
<212> TYPE: PRT
<213> ORGANISM: Artificial Sequence
<220> FEATURE:
<223> OTHER INFORMATION: Crown domain Sequence (366  430) of PLAP

<400> SEQUENCE: 6

Gly Tyr Pro Leu Arg Gly Ser Ser Ile Phe Gly Leu Ala Pro Gly Lys
1               5                   10                  15

Ala Arg Asp Arg Lys Ala Tyr Thr Val Leu Leu Tyr Gly Asn Gly Pro
            20                  25                  30

Gly Tyr Val Leu Lys Asp Gly Ala Arg Pro Asp Val Thr Glu Ser Glu
        35                  40                  45

Ser Gly Ser Pro Glu Tyr Arg Gln Gln Ser Ala Val Pro Leu Asp Glu
    50                  55                  60

Glu
65

<210> SEQ ID NO 7
<211> LENGTH: 54
<212> TYPE: PRT
<213> ORGANISM: Homo sapiens

<400> SEQUENCE: 7

Thr His Gly Gly Glu Asp Val Ala Val Phe Ala Arg Gly Pro Gln Ala
1               5                   10                  15

His Leu Val His Gly Val Gln Glu Gln Ser Phe Val Ala His Val Met
            20                  25                  30

Ala Phe Ala Ala Cys Leu Glu Pro Tyr Thr Ala Cys Asp Leu Ala Pro
        35                  40                  45

Pro Ala Cys Thr Thr Asp
    50
```